US010954545B2

(12) United States Patent
Ustav et al.

(10) Patent No.: US 10,954,545 B2
(45) Date of Patent: Mar. 23, 2021

(54) ASSAY SYSTEM TO IDENTIFY HPV REPLICATION INHIBITORS IN HT-SCREEN

(71) Applicant: Icosagen Cell Factory OÜ, Tartumaa (EE)

(72) Inventors: Mart Ustav, Össu (EE); Ene Ustav, Össu (EE); Andres Männik, Össu (EE); Mart Toots, Össu (EE); Mart Ustav, Jr., Össu (EE); Andres Tover, Össu (EE)

(73) Assignee: Icosagen Cell Factory OÜ, Tartumaa (EE)

( * ) Notice: Subject to any disclaimer, the term of this patent is extended or adjusted under 35 U.S.C. 154(b) by 325 days.

(21) Appl. No.: 15/565,175

(22) PCT Filed: Apr. 11, 2016

(86) PCT No.: PCT/EP2016/057898
§ 371 (c)(1),
(2) Date: Oct. 9, 2017

(87) PCT Pub. No.: WO2016/162555
PCT Pub. Date: Oct. 13, 2016

(65) Prior Publication Data

US 2018/0155756 A1 Jun. 7, 2018

Related U.S. Application Data

(60) Provisional application No. 62/145,243, filed on Apr. 9, 2015.

(51) Int. Cl.

| | |
|---|---|
| ***C12N 15/11*** | (2006.01) |
| ***A61K 38/00*** | (2006.01) |
| ***A61K 48/00*** | (2006.01) |
| ***C07K 14/705*** | (2006.01) |
| ***C12N 15/86*** | (2006.01) |
| ***C12Q 1/18*** | (2006.01) |
| ***C12Q 1/70*** | (2006.01) |
| ***C12N 5/09*** | (2010.01) |

(52) U.S. Cl.
CPC ............. *C12Q 1/18* (2013.01); *C12N 5/0693* (2013.01); *C12N 15/86* (2013.01); *C12Q 1/706* (2013.01); *C12Q 1/708* (2013.01); *C12N 2503/02* (2013.01); *C12N 2510/00* (2013.01); *C12N 2710/16621* (2013.01); *C12N 2710/16622* (2013.01); *C12N 2710/20011* (2013.01); *C12Q 2600/136* (2013.01); *G01N 2333/025* (2013.01); *G01N 2500/10* (2013.01)

(58) Field of Classification Search
CPC ...... A61K 38/00; C07K 14/005; C07K 14/47; C07K 14/705; C12N 15/1131
See application file for complete search history.

(56) References Cited

U.S. PATENT DOCUMENTS

2013/0150262 A1* 6/2013 Ustav .................... C12Q 1/708 506/13

OTHER PUBLICATIONS

Bellanger, S. et al: "Stability of the Human Papillomavirus Type 18 E2 Protein Is Regulated by a Proteasome Degradation Pathway through Its Amino-Terminal Transactivation Domain", Journal of Virology, vol. 75, No. 16, Aug. 15, 2001, pp. 7244-7251, XP55290727, US ISSN: 002-538X, DOI: 10.1128/JVI.75.16.7244-7251.2001-.

Sherman, L. et al: "The E2 protein of human papillomavirus type 16 is translated from a variety of differentially spliced polycistronic mRNAs", Journal of General Virology, vol. 80, No. 1, Jan. 1, 1999, pp. 29-37, XP55290245, GB, ISSN: 0022-1317, DOI: 10.1099/022-1317-80-1-29.

Kurg, R. et al: "Human papillomavirus E2 protein with single activation domain initiates HPV18 genome replication, but is not sufficient for long-term maintenance of virus genome", Virology, Elsevier, Amsterdam, NL, vol. 408, No. 2, Dec. 20, 2010, pp. 159-166, XP027475954, ISSN: 0042-6822, DOI: 10.1016/J.VIROL.2010.09.010 [retrieved on Oct. 12, 2010].

Bemard HU, Burk RD, Chen Z, van Doorslaer K, zur Hausen H, et al. (2010) Classification of papillomaviruses (PVs) based on 189 PV types and proposal of taxonomic amendments. Virology 401: 70-79.

Munoz N, Bosch FX, de Sanjose S, Herrero R, Castellsague X, et al. (2003) Epidemiologic classification of human papillomavirus types associated with cervical cancer. N Engl J Med 348: 518-527.

Munoz N, Castellsague X, de Gonzalez AB, Gissmann L (2006) Chapter 1: HPV in the etiology of human cancer. Vaccine 24 Suppl 3: S3/1-10.

Bouvard V, Baan R, Straif K, Grosse Y, Secretan B, et al. (2009) A review of human carcinogens—Part B: biological agents. Lancet Oncol 10: 321-322.

(Continued)

*Primary Examiner* — Barry A Chestnut

(74) *Attorney, Agent, or Firm* — Berggren LLP

(57) ABSTRACT

A U2OS-based model system using luciferase reporters to monitor the genome replication of alpha and beta HPVs is provided. A modified U2OS cell line is disclosed that expresses Firefly luciferase to measure toxicity of the screened compounds. In addition, provided are HPV18, HPV 16 and HPV5 marker genomes that express *Renilla* luciferase under the control of viral promoters used to measure changes in the viral copy number. This ready-to-use model system is capable of being used in high-throughput screens to identify compounds inhibiting initial amplification and stable maintenance as well as vegetative phase of various HPV subtypes.

9 Claims, 10 Drawing Sheets

Specification includes a Sequence Listing.

(56) References Cited

OTHER PUBLICATIONS

Ferlay J, Shin HR, Bray F, Forman D, Mathers C, et al. (2010) Estimates of worldwide burden of cancer in 2008: GLOBOCAN 2008. Int J Cancer 127: 2893-2917.
Dunne EF, Unger ER, Sternberg M, McQuillan G, Swan DC, et al. (2007) Prevalence of HPV infection among females in the United States. JAMA 297: 813-819.
Roman A, Munger K (2013) The papillomavirus E7 proteins. Virology 445: 138-168.
Vande Pol SB, Klingelhutz AJ (2013) Papillomavirus E6 oncoproteins. Virology 445: 115-137.
Akgul B, Cooke JC, Storey A (2006) HPV-associated skin disease. J Pathol 208: 165-175.
Malik H, Khan FH, Ahsan H (2014) Human papillomavirus: current status and issues of vaccination. Arch Virol 159: 199-205.
Hebner CM, Laimins LA (2006) Human papillomaviruses: basic mechanisms of pathogenesis and oncogenicity. Rev Med Virol 16: 83-97.
Doorbar J, Quint W, Banks L, Bravo IG, Stoler M, et al. (2012) The biology and life-cycle of human papillomaviruses. Vaccine 30 Suppl 5: F55-70.
Androphy EJ, Lowy DR, Schiller JT (1987) Bovine papillomavirus E2 trans-activating gene product binds to specific sites in papillomavirus DNA. Nature 325: 70-73.
Mohr IJ, Clark R, Sun S, Androphy EJ, MacPherson P, et al. (1990) Targeting the E1 replication protein to the papillomavirus origin of replication by complex formation with the E2 transactivator. Science 250: 1694-1699.
Blitz IL, Laimins LA (1991) The 68-kilodalton E1 protein of bovine papillomavirus is a DNA binding phosphoprotein which associates with the E2 transcriptional activator in vitro. J Virol 65: 649-656.
Weitzman MD, Lilley CE, Chaurushiya MS (2010) Genomes in conflict: maintaining genome integrity during virus infection. Annu Rev Microbiol 64: 61-81.
McFadden K, Luftig MA (2013) Interplay between DNA tumor viruses and the host DNA damage response. Curr Top Microbiol Immunol 371: 229-257.
Marechal A, Zou L (2013) DNA damage sensing by the ATM and ATR kinases. Cold Spring Harb Perspect Biol 5.
Reinson T, Toots M, Kadaja M, Pipitch R, Allik M, et al. (2013) Engagement of the ATR-dependent DNA damage response at the human papillomavirus 18 replication centers during the initial amplification. J Virol 87: 951-964.
Sakakibara N, Mitra R, McBride AA (2011) The papillomavirus E1 helicase activates a cellular DNA damage response in viral replication foci. J Virol 85: 8981-8995.
Fradet-Turcotte A, Bergeron-Labrecque F, Moody CA, Lehoux M, Laimins LA, et al. (2011) Nuclear accumulation of the papillomavirus E1 helicase blocks S-phase progression and triggers an ATM-dependent DNA damage response. J Virol 85: 8996-9012.
Moody CA, Laimins LA (2009) Human papillomaviruses activate the ATM DNA damage pathway for viral genome amplification upon differentiation. PLoS Pathog 5: e1000605.
Oray M, Henno L, Isok-Paas H, Geimanen J, Ustav M, et al. (2013) Recombination-dependent oligomerization of human papillomavirus genomes upon transient DNA replication. J Virol 87: 12051-12068.
Gillespie KA, Mehta KP, Laimins LA, Moody CA (2012) Human papillomaviruses recruit cellular DNA repair and homologous recombination factors to viral replication centers. J Virol 86: 9520-9526.
Fradet-Turcotte A, Morin G, Lehoux M, Bullock PA, Archambault J (2010) Development of quantitative and high-throughput assays of polyomavirus and papillomavirus DNA replication. Virology 399: 65-76.
Lembo D, Donalisio M, De Andrea M, Cornaglia M, Scutera S, et al. (2006) A cell-based high-throughput assay for screening inhibitors of human papillomavirus-16 long control region activity. FASEB J 20: 148-150.
Wang Y, Li X, Song S, Wu J (2014) Development of Basal-Like HaCaT Keratinocytes Containing the Genome of Human Papillomavirus (HPV) Type 11 for Screening of Anti-HPV Effects. J Biomol Screen 19: 1154-1163.
Huang HS, Pyeon D, Pearce SM, Lank SM, Griffin LM, et al. (2012) Novel antivirals inhibit early steps in HPV infection. Antiviral Res 93: 280-287.
Geimanen J, Isok-Paas H, Pipitch R, Salk K, Laos T, et al. (2011) Development of a cellular assay system to study the genome replication of high- and low-risk mucosal and cutaneous human papillomaviruses. J Virol 85: 3315-3329.
Sankovski E, Mannik A, Geimanen J, Ustav E, Ustav M (2014) Mapping of betapapillomavirus human papillomavirus 5 transcription and characterization of viral-genome replication function. J Virol 88: 961-973.
Toots M, Mannik A, Kivi G, Ustav M, Jr., Ustav E, et al. (2014) The transcription map of human papillomavirus type 18 during genome replication in U2OS cells. PLoS One 9: e116151.
Wang X, Meyers C, Wang HK, Chow LT, Zheng ZM (2011) Construction of a full transcription map of human papillomavirus type 18 during productive viral infection. J Virol 85: 8080-8092.
Chow LT, Nasseri M, Wolinsky SM, Broker TR (1987) Human papillomavirus types 6 and 11 mRNAs from genital condylomata acuminata. J Virol 61: 2581-2588.
Blais JD, Addison CL, Edge R, Falls T, Zhao H, et al. (2006) Perk-dependent translational regulation promotes tumor cell adaptation and angiogenesis in response to hypoxic stress. Mol Cell Biol 26: 9517-9532.
Johansson C, Somberg M, Li X, Backstrom Winquist E, Fay J, et al. (2012) HPV-16 E2 contributes to induction of HPV-16 late gene expression by inhibiting early polyadenylation. EMBO J 31: 3212-3227.
Kay MA, He CY, Chen ZY (2010) A robust system for production of minicircle DNA vectors. Nat Biotechnol 28: 1287-1289.
Hirt B (1967) Selective extraction of polyoma DNA from infected mouse cell cultures. J Mol Biol 26: 365-369.

* cited by examiner

SEQUENCE LISTING

```
<160> NUMBER OF SEQ ID NOS: 43

<210> SEQ ID NO 1
<211> LENGTH: 12896
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(12896)
```

-continued

<223> OTHER INFORMATION: pMC_HPV5-Rluc-E2

<400> SEQUENCE: 1

```
acattaccct gttatcccta gatgacatta ccctgttatc ccagatgaca ttaccctgtt     60
atccctagat gacattaccc tgttatccct agatgacatt taccctgtta tccctagatg    120
acattaccct gttatcccag atgacattac cctgttatcc ctagatacat taccctgtta    180
tcccagatga cataccctgt tatccctaga tgacattacc ctgttatccc agatgacatt    240
accctgttat ccctagatac attaccctgt tatcccagat gacataccct gttatcccta    300
gatgacatta ccctgttatc ccagatgaca ttaccctgtt atccctagat acattaccct    360
gttatcccag atgacatacc ctgttatccc tagatgacat taccctgtta tcccagatga    420
cattaccctg ttatccctag atacattacc ctgttatccc agatgacata ccctgttatc    480
cctagatgac attaccctgt tatcccagat gacattaccc tgttatccct agatacatta    540
ccctgttatc ccagatgaca taccctgtta tccctagatg acattaccct gttatcccag    600
atgacattac cctgttatcc ctagatacat taccctgtta tcccagatga cataccctgt    660
tatccctaga tgacattacc ctgttatccc agataaactc aatgatgatg atgatgatgg    720
tcgagactca gcggccgcgg tgccagggcg tgcccttggg ctccccgggc gcgactagtg    780
aattcagatc tgatatctct aggtttgaaa ctacaagaaa tggttcatac tatatacaag    840
acacaaaggg atattatgtt gcatatccag agtcacgtaa taatgcagaa atcatttatc    900
ctacacctga tattcctgtg gtcattatac accctcatga caatacaggg gacttttatt    960
tacatcccag tcttcgcagg cgaaaacgta aaagaaaata tttgtgattt gcattgcaga   1020
tggcagtgtg gcactcggct aatggtaaag tatatcttcc accatcgaca ccggtggcca   1080
gagtccaaag caccgatgaa tacattcaaa gaacaaatat ctactatcat gcatttagtg   1140
acagattgtt aactgtaggt catccttatt tcaatgtata caatattaat ggtgacaaac   1200
ttgaggttcc taaggtttca ggaaatcaac acagagtatt tcgcctaaaa ttaccagatc   1260
ccaacagatt tgcattagct gatatgtctg tttacaaccc tgacaaagaa cggttggttt   1320
gggcctgtag aggcttagaa ataggtaggg gccagccatt aggtgtaggg agtactggtc   1380
acccttattt caataaagta aaagatacag aaaacagtaa tgcatacata acattttcta   1440
aggatgacag acagaataca tcttttgatc ctaaacagat ccaaatgttt attgtaggat   1500
gcacaccttg catagggag cattgggata aagctgttcc atgtgcagaa aatgatcaac   1560
aaactggcct ttgtcctcct attgaattaa aaaacacata tatagaagat ggtgatatgg   1620
cagacatagg ttttggaaac atgaatttta aggcacttca agatagtaga tcagatgtca   1680
gtttagacat cgtcaatgaa acttgcaagt atccagattt tttaaagatg caaaacgata   1740
tttatggcga tgcgtgcttt ttttatgctc gtagggagca atgttatgcc agacactttt   1800
ttgttagagg gggtaaaact ggtgatgaca ttccaggtgc acaaattgac aatggtacat   1860
acaaaaatca gttttacatt ccaggggctg atggccaagc tcaaaagact ataggaaatg   1920
ccatgtattt cccaactgtt agtggctcat tagtatccag tgatgctcaa ttgtttaaca   1980
ggcccttctg gctccaaaga gcccaaggtc ataataatgg catcctgtgg gctaatcaaa   2040
tgtttatcac agtggttgac aacacaagaa atactaattt cagtatttct gtatataatc   2100
aggctggggc cctaaaagat gttgcagact ataatgcaga tcaatttaga gaatatcaaa   2160
gacatgtaga agaatatgaa atatctttaa ttttacaact ctgtaaggtt cctttaaagg   2220
cagaggtatt ggcacagatc aatgcaatga actcttcgtt attggaggat tggcagttag   2280
```

```
gatttgttcc cactcctgat aatccaattc aggataccta cagatatatt gactctttgg   2340
ctacacgatg tccagataaa aatcctccga aagaaaagga agacccttat aaaggcttac   2400
atttttggga tgtagattta actgaaagat tgtcattaga tttagatcaa tattccttag   2460
gcagaaaatt tttattccaa gctgggttac aacaaacgac cgttaacggt acaaaagcag   2520
tgtcttataa agggtctaat agaggaacaa aacgcaaacg taaaaattga ggtctgaccg   2580
aaagtggtac atttttataa acttttacac agtattcaaa gaatgtttgt ttactctgac   2640
taagtataag tcttccaagg ataccgaccg cacccggtac actcagtcaa gttgttgcca   2700
atatagaatc agatcagtgc caaacacacc gtcttggact cagaacagac cgtgttcgtt   2760
ataacatgct cggattaggg acgtcgccaa agaagattta atctacaatc gcttttggca   2820
atcgcatttg gcactgctaa acgaccgtta acggtaagtt gcaattttct tgtaccaggt   2880
gcggtattaa gatttcacaa ttgtaatggt tgttgccaac taccataggc atattcaagt   2940
ttttgcctgt atcgttttcg tatcctgtta acaatatcca atatatgtat acataaataa   3000
atatatatat atataagtgt ctgagattgg gttcttctgt aatcaggcaa tggctgaggg   3060
agccgaacac caaccaaaac tgacagaaaa agataaggca gaatttcctt caagtattag   3120
agagttagct gaaaccttag gcatccctct gattgattgt ttaatacctt gcaatttctg   3180
tggcaaattt ctaaattatt tggaagcttg cgaattcgac tacaaaaaac ttagtctaat   3240
ttggaaagat tattgtgtgt ttgcgtgctg tcgcgtatgc tgtggcgcca ctgcaactta   3300
tgaatttaac caattttatg agcagacagt tttaggacga gatattgagt tagcttcagg   3360
actttcgatt tttgatattg atatcaggtg tcaaacttgc ttagcatttc ttgacattat   3420
agaaaagtta gattgctgtg gcagaggcct tccctttcat aaggtgagga acgcctggaa   3480
gggaatctgt aggcagtgta agcattttta tcatgattgg taaagaggtc accgtgcaag   3540
atattattct ggagctcagt gaggtgcagc ccgaagtgct accagttgac ctgttttgtg   3600
aagaggaatt accaaacgag caggaaacgg aggaggagcc tgacaacgaa aggatctctt   3660
acaaagttat agctccgtgc ggttgcagga actgtgaggt caagcttcgc atttttgtcc   3720
acgccacaga atttggtatt agagctttcc aacagctact gaccggagat ctgcagctcc   3780
tgtgccccga ctgtcgcgga aactgcaaac atgacggatc ctaattctaa aggtagtaca   3840
tctaaagaag ggtttggtga ttggtgttta ttggaagctg actgtagtga tgtagaaaat   3900
gatttgggac aattatttga gagagataca gactctgata tatcggattt gttagatgat   3960
actgaactgg agcagggcaa ttctttggaa ctatttcatc aacaggagtg tgagcagagc   4020
gaggagcaat tacaaaaact aaaacgaaag tatcttagtc caaaagctgt cgcacagctt   4080
agtccgcgac ttgagtcaat ttcattgtca cctcagcaga agtctaagcg aaggcttttt   4140
gcagagcagg acagcggact cgagctgact ttaaacaatg aagctgaaga tgttactcct   4200
gaggtggagg taccggctat tgactctcgg ccggatgacg agggaggttc aggggacgta   4260
gatatacatt ttactgcatt gttgcgttct agcaacaaaa aagctacatt aatggctaag   4320
tttaaagagt catttggagt aggttttaat gaattgacac ggcaattcaa aagccacaaa   4380
acctgctgta aagactgggt tgtctctgta tatgcagtgc atgatgattt atttgaaagc   4440
tcaaagcagc tgttgcaaca gcattgtgac tatatctggg tccgtgggat aggtgcaatg   4500
tcattatatc tattgtgttt caaggcggga aaaaatcgcg ggacagttca taagttaatt   4560
acctcaatgt taaatgtgca tgaacagcaa atattgtctg agccgccaaa attgagaaac   4620
```

-continued acagccgctg cattgttctg gtataagggt tgtatgggat cgggggcgtt tagccatgga 4680
ccatatcctg attggattgc ccaacaaact atattaggtc acaaaagtgc tgaggcaagt 4740
acttttgatt tttcagcaat ggtacaatgg gcgtttgata atcatttatt agacgaagca 4800
gatatagcat accagtatgc aaggcttgca cccgaagatg cgaatgcagt agcttggctt 4860
gcacataaca accaggccaa atttgtgaga gaatgtgctt atatggtacg attctataag 4920
aagggacaaa tgagagacat gagcatatct gaatggatat acactaaaat caatgaagta 4980
gaaggggaag ggcactggtc agatatagta aagtttatta gataccaaaa tataaacttt 5040
attgtatttc taactgcatt aaaagaattc ctacactcag tgccaaaaaa aaattgtatt 5100
ttaatttatg gtcctccaaa ttctggaaag tcatcatttg caatgtcttt aataagagtg 5160
ttgaagggta gggtgttgtc atttgtgaac tctaaaagtc agttttggct gcaacccctt 5220
tcagagtgca agatagctct attggatgat gtaacagacc cttgttggat atacatggat 5280
acatatttaa gaaatggctt ggatggacat tatgtttcat tagattgtaa atatagagcc 5340
ccaacgcaaa tgaaatttcc cccattatta ttaacatcta acatcaatgt gcatggggaa 5400
actaattata gatatttaca cagtagaata aaaggatttg aatttccaaa tccttttcct 5460
atgaaagcag ataatacacc tcagtttgaa ctaactgacc aaagctggaa atcttttttt 5520
acaaggcttt ggacacaatt agacctgagt gatcaagaag aggagggcga ggatggagaa 5580
tctcagcgag cgtttcaatg ctctgcaaga tcagctaatg aacatttatg aagccacttc 5640
gaaagtttat gatccagaac aaaggaaacg gatgataact ggtccgcagt ggtgggccag 5700
atgtaaacaa atgaatgttc ttgattcatt tattaattat tatgattcag aaaaacatgc 5760
agaaaatgct gttatttttt tacatggtaa cgcggcctct tcttatttat ggcgacatgt 5820
tgtgccacat attgagccag tagcgcggtg tattatacca gaccttattg gtatgggcaa 5880
atcaggcaaa tctggtaatg gttcttatag gttacttgat cattacaaat atcttactgc 5940
atggtttgaa cttcttaatt taccaaagaa gatcattttt gtcggccatg attggggtgc 6000
ttgtttggca tttcattata gctatgagca tcaagataag atcaaagcaa tagttcacgc 6060
tgaaagtgta gtagatgtga ttgaatcatg ggatgaatgg cctgatattg aagaagatat 6120
tgcgttgatc aaatctgaag aaggagaaaa aatggttttg gagaataact tcttcgtgga 6180
aaccatgttg ccatcaaaaa tcatgagaaa gttagaacca gaagaatttg cagcatatct 6240
tgaaccattc aaagagaaag gtgaagttcg tcgtccaaca ttatcatggc ctcgtgaaat 6300
cccgttagta aaaggtggta aacctgacgt tgtacaaatt gttaggaatt ataatgctta 6360
tctacgtgca agtgatgatt taccaaaaat gtttattgaa tcggacccag gattcttttc 6420
caatgctatt gttgaaggtg ccaagaagtt tcctaatact gaatttgtca aagtaaaagg 6480
tcttcatttt tcgcaagaag atgcacctga tgaaatggga aaatatatca aatcgttcgt 6540
tgagcgagtt ctcaaaaatg aacaagcacc ggtgaaacag actttgaatt ttgaccttct 6600
caagttggcg ggagacgtgg agtccaaccc tgggcccatg gagaatctca gcgagcgttt 6660
caatgctctg caagatcagc taatgaacat ttatgaagct gcagaacaaa cattgcaggc 6720
acaaattaaa cattggcaaa ccttacgaaa agaagctgta ttactctact atgctaggga 6780
gaaaggtgtt acaaggcttg gatatcaacc tgtgcctgta aaggcagtat cagaaacaaa 6840
ggctaaagaa gccatagcaa tggtgctgca gcttgagtca ctacagacgt ctgattttgc 6900
tcatgagcca tggactctag ttgataccag catagaaaca tttagaagcg ctccagaagg 6960
tcacttcaaa aaaggccccg tccctgtaga agttatttat gacaatgatc cagataatgc 7020

```
caatttgtat acaatgtgga cctatgtgta ttatatggat gcggatgata agtggcataa   7080
ggcaagaagt ggggtgaatc acattggcat ttattattta caaggaacgt ttaaaaacta   7140
ttatgtactg tttgctgacg atgcaaaaag atatggtaca actggagaat gggaagtaaa   7200
agttaataag gaaactgtgt ttgctcctgt caccagctcc acgcctccag ggtcgccagg   7260
aggacaagca gacacaaaca ccacctccgc gacccccacc acctccacaa ccgccgttga   7320
ctccacgtcc agacagctca ctacatcaaa acagccacaa caaaccgaaa ccagaggaag   7380
aaggtacgga cggagggcct ccagcaagtc aaggagatcg caaacgcagc aaaggcgatc   7440
aaggtcccga caccggtccc ggtctcggtc ccggtcgcgg tccaagtcca aaacccacac   7500
cactcggtcc accaccaggt cccggtccac gtcgctcacc aagactcggg cccttacaag   7560
cagatcgcga tccagaggaa ggtccccaac cacctgcaga aggggaggtg gaaggtcacc   7620
caggcggcga tcaaggtcac cctccacctc ctcctcctgc accacacaac ggtcacagcg   7680
ggcacgggcc gaaagttcaa caaccagagg ggcccgaggg tcgagagggt cacgaggagg   7740
gagccgtggg gggagagggc ggcgacgagg aaggtcatcc tcctcctcct cccccaccca   7800
caaacggtca cgaggggaat ctgctaagct ccgtggcgtc tctcctggtg aagtgggagg   7860
gtcacttcga tcagttagtt caaagcatac aggtcgactt ggaagattac tggaagaagc   7920
tcgcgacccc ccagtaatca ttgtcaaagg ggcggctaac acactgaaat gcttccgcaa   7980
cagagctaaa attacataca agggactgtt taggtcattt agcactacct ggtcatgggt   8040
ggcaggagat ggcactgagc gtctaggcag gcccagaatg ctcattagct tttcttcata   8100
tactcaaagg agagattttg atgaagcggt acgataccct aaaggagttg ataaggccta   8160
tggcaacctg gacagtcttt aacatttact aatgctgctt ctgctactaa catattaaca   8220
taccctagca ttttatattt ttttttacat tttgtatttg ctatggcgcg tgctagaagg   8280
gtcaagcgag actctgtaac tcatatttac caaacctgca aacaggcagg cacttgcccc   8340
cctgatgtta ttaataaagt ggaacaaaca acagttgctg acaatatttt aaaatatggc   8400
agtgctggtg tatttttttgg tggccttggt attagtacag gccgaggaac tgggggtgct   8460
acagggtacg tgccacttgg ggaaggtcct ggtgtccgtg tcggaggaac ccccacggtt   8520
gtaaggcctt ccttggttcc tgaaacaatc gggcccgttg atattttgcc cattgataca   8580
gttaaccccg tggaacctac agcatcatcc gtggtccctt taactgagtc cacaggcgct   8640
gatttacttc caggtgaagt agaaacaatt gctgaaattc atcctgtacc tgaagggcca   8700
tcagtagata ctcctgtagt taccactagc acaggttcca gtgctgtttt agaggtttcc   8760
ccagagccta ttcctccaac acgggtcaga gtttcacgaa cacaatatca caatccatct   8820
tttcaaataa taactgagtc tactccagca caaggggaat cgtctcttgc agatcacgtt   8880
ttggtgacat cgggttctgg ggggcaacga atagggggtg atataactga cataattgag   8940
ttagaggaaa tccctagtag gtatacattt gaaattgaag aaccaactcc tccacgccgc   9000
agcagtactc cattgtcacg cactcaatct gtaggccgta ggaggggttt gtcgttgact   9060
aatagacgtt tggtacagca ggtacaagtg gacaatccat tgtttctaac tcaaccatct   9120
aagttagttc gttttgcatt tgataatcct gtttttgagg aagaagtgac taatatattt   9180
gaaaatgatc tggatgtctt tgaagaacct ccagacagag attttcttga tgttagaaaa   9240
ttgggacgtc cacaatattc tacaacacca gcgggatatg tcagagtaag caggttgggg   9300
actcgagcca ctattcgcac tcgctctggt gcacaaatag ggtcgcaagt ccatttttac   9360
```

-continued

```
agagatctta gctctattaa tactgaggat cctattgaat tacaattatt aggccaacat   9420
tcaggtgatg ctactatagt ccagggacct gttgaaagca catttataga tatggatatt   9480
tctgaaaatc cattatctga aagcatcgaa gcatattcac atgatttatt attagatgag   9540
gcggtggaag atttcagtgg gtctcagctg gttataggta atcgaaggag cacaaattct   9600
tacactgttc ctagagtcga cccatggggg cccgccccaa ctggggtaac ctttgagttc   9660
tctcagttgg gggtaatcag catcatgatg tggtaccaca tcatgatgct gattataaga   9720
atgcggccgc cacactctag tggatctcga gttaataatt cagaagaact cgtcaagaag   9780
gcgatagaag gcgatgcgct gcgaatcggg agcggcgata ccgtaaagca cgaggaagcg   9840
gtcagcccat tcgccgccaa gctcttcagc aatatcacgg gtagccaacg ctatgtcctg   9900
atagcggtcc gccacaccca gccggccaca gtcgatgaat ccagaaaagc ggccattttc   9960
caccatgata ttcggcaagc aggcatcgcc atgggtcacg acgagatcct cgccgtcggg  10020
catgctcgcc ttgagcctgg cgaacagttc ggctggcgcg agcccctgat gctcttcgtc  10080
cagatcatcc tgatcgacaa gaccggcttc catccgagta cgtgctcgct cgatgcgatg  10140
tttcgcttgg tggtcgaatg ggcaggtagc cggatcaagc gtatgcagcc gccgcattgc  10200
atcagccatg atggatactt tctcggcagg agcaaggtgt agatgacatg gagatcctgc  10260
cccggcactt cgcccaatag cagccagtcc cttcccgctt cagtgacaac gtcgagcaca  10320
gctgcgcaag gaacgcccgt cgtggccagc cacgatagcc gcgctgcctc gtcttgcagt  10380
tcattcaggg caccggacag gtcggtcttg acaaaaagaa ccgggcgccc ctgcgctgac  10440
agccggaaca cggcggcatc agagcagccg attgtctgtt gtgcccagtc atagccgaat  10500
agcctctcca cccaagcggc cggagaacct gcgtgcaatc catcttgttc aatcatgcga  10560
aacgatcctc atcctgtctc ttgatcagag cttgatcccc tgcgccatca gatccttggc  10620
ggcgagaaag ccatccagtt tactttgcag ggcttcccaa ccttaccaga gggcgcccca  10680
gctggcaatt ccggttcgct tgctgtccat aaaaccgccc agtctagcta tcgccatgta  10740
agcccactgc aagctacctg ctttctcttt gcgcttgcgt tttcccttgt ccagatagcc  10800
cagtagctga cattcatccg gggtcagcac cgtttctgcg gactggcttt ctacgtgctc  10860
gagggggccc aaacggtctc cagcttggct gttttggcgg atgagagaag attttcagcc  10920
tgatacagat taaatcagaa cgcagaagcg gtctgataaa acagaatttg cctggcggca  10980
gtagcgcggt ggtcccacct gaccccatgc cgaactcaga agtgaaacgc cgtagcgccg  11040
atggtagtgt ggggtctccc catgcgagag tagggaactg ccaggcatca aataaaacga  11100
aaggctcagt cgaaagactg ggcctttcgt tttatctgtt gtttgtcggt gaacgctctc  11160
ctgagtagga caaatccgcc gggagcggat ttgaacgttg cgaagcaacg gcccggaggg  11220
tggcgggcag gacgcccgcc ataaactgcc aggcatcaaa ttaagcagaa ggccatcctg  11280
acggatggcc tttttgcgtt tctacaaact cttttgttta tttttctaaa tacattcaaa  11340
tatgtatccg ctcatgacca aaatccctta acgtgagttt tcgttccact gagcgtcaga  11400
ccccgtagaa aagatcaaag gatcttcttg agatcctttt tttctgcgcg taatctgctg  11460
cttgcaaaca aaaaaaccac cgctaccagc ggtggtttgt ttgccggatc aagagctacc  11520
aactcttttt ccgaaggtaa ctggcttcag cagagcgcag ataccaaata ctgtccttct  11580
agtgtagccg tagttaggcc accacttcaa gaactctgta gcaccgccta catacctcgc  11640
tctgctaatc ctgttaccag tggctgctgc cagtggcgat aagtcgtgtc ttaccgggtt  11700
ggactcaaga cgatagttac cggataaggc gcagcggtcg ggctgaacgg ggggttcgtg  11760
```

```
cacacagccc agcttggagc gaacgaccta caccgaactg agatacctac agcgtgagct  11820

atgagaaagc gccacgcttc ccgaagggag aaaggcggac aggtatccgg taagcggcag  11880

ggtcggaaca ggagagcgca cgagggagct tccaggggga aacgcctggt atctttatag  11940

tcctgtcggg tttcgccacc tctgacttga gcgtcgattt ttgtgatgct cgtcaggggg  12000

gcggagccta tggaaaaacg ccagcaacgc ggccttttta cggttcctgg ccttttgctg  12060

gccttttgct cacatgttct ttcctgcgtt atcccctgat tctgtggata accgtattac  12120

cgcctttgag tgagctgata ccgctcgccg cagccgaacg accgagcgca gcgagtcagt  12180

gagcgaggaa gcggaagagc gcctgatgcg gtattttctc cttacgcatc tgtgcggtat  12240

ttcacaccgc atatggtgca ctctcagtac aatctgctct gatgccgcat agttaagcca  12300

gtatacactc cgctatcgct acgtgactgg gtcatggctg cgccccgaca cccgccaaca  12360

cccgctgacg cgccctgacg ggcttgtctg ctcccggcat ccgcttacag acaagctgtg  12420

accgtctccg ggagctgcat gtgtcagagg ttttcaccgt catcaccgaa acgcgcgagg  12480

cagcagatca attcgcgcgc gaaggcgaag cggcatgcat aatgtgcctg tcaaatggac  12540

gaagcaggga ttctgcaaac cctatgctac tccgtcaagc cgtcaattgt ctgattcgtt  12600

accaattatg acaacttgac ggctacatca ttcacttttt cttcacaacc ggcacggaac  12660

tcgctcgggc tggccccggt gcatttttta aatacccgcg agaaatagag ttgatcgtca  12720

aaaccaacat tgcgaccgac ggtggcgata ggcatccggg tggtgctcaa aagcagcttc  12780

gcctggctga tacgttggtc ctcgcgccag cttaagacgc taatccctaa ctgctggcgg  12840

aaaagatgtg acagacgcga cggcgacaag caaacatgct gtgcgacgct ggcgat      12896
```

```
<210> SEQ ID NO 2
<211> LENGTH: 8812
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(8812)
<223> OTHER INFORMATION: HPV5-Rluc-E2 marker genome

<400> SEQUENCE: 2
```

```
ctaggtttga aactacaaga aatggttcat actatataca agacacaaag ggatattatg     60

ttgcatatcc agagtcacgt aataatgcag aaatcattta tcctacacct gatattcctg    120

tggtcattat acaccctcat gacaatacag gggactttta tttacatccc agtcttcgca    180

ggcgaaaacg taaaagaaaa tatttgtgat ttgcattgca gatggcagtg tggcactcgg    240

ctaatggtaa agtatatctt ccaccatcga caccggtggc cagagtccaa agcaccgatg    300

aatacattca aagaacaaat atctactatc atgcatttag tgacagattg ttaactgtag    360

gtcatcctta tttcaatgta tacaatatta atggtgacaa acttgaggtt cctaaggttt    420

caggaaatca acacagagta tttcgcctaa aattaccaga tcccaacaga tttgcattag    480

ctgatatgtc tgtttacaac cctgacaaag aacggttggt ttgggcctgt agaggcttag    540

aaataggtag gggccagcca ttaggtgtag ggagtactgg tcacccttat ttcaataaag    600

taaaagatac agaaaacagt aatgcataca taacattttc taaggatgac agacagaata    660

catcttttga tcctaaacag atccaaatgt ttattgtagg atgcacacct tgcatagggg    720

agcattggga taaagctgtt ccatgtgcag aaaatgatca acaaactggc ctttgtcctc    780
```

-continued

```
ctattgaatt aaaaaacaca tatatagaag atggtgatat ggcagacata ggttttggaa    840
acatgaattt taaggcactt caagatagta gatcagatgt cagtttagac atcgtcaatg    900
aaacttgcaa gtatccagat tttttaaaga tgcaaaacga tatttatggc gatgcgtgct    960
ttttttatgc tcgtagggag caatgttatg ccagacactt ttttgttaga gggggtaaaa   1020
ctggtgatga cattccaggt gcacaaattg acaatggtac atacaaaaat cagttttaca   1080
ttccaggggc tgatggccaa gctcaaaaga ctataggaaa tgccatgtat ttcccaactg   1140
ttagtggctc attagtatcc agtgatgctc aattgtttaa caggcccttc tggctccaaa   1200
gagcccaagg tcataataat ggcatcctgt gggctaatca aatgtttatc acagtggttg   1260
acaacacaag aaatactaat ttcagtattt ctgtatataa tcaggctggg gccctaaaag   1320
atgttgcaga ctataatgca gatcaattta gagaatatca aagacatgta gaagaatatg   1380
aaatatcttt aattttacaa ctctgtaagg ttcctttaaa ggcagaggta ttggcacaga   1440
tcaatgcaat gaactcttcg ttattggagg attggcagtt aggatttgtt cccactcctg   1500
ataatccaat tcaggatacc tacagatata ttgactcttt ggctacacga tgtccagata   1560
aaaatcctcc gaaagaaaag gaagaccctt ataaaggctt acatttttgg gatgtagatt   1620
taactgaaag attgtcatta gatttagatc aatattcctt aggcagaaaa tttttattcc   1680
aagctgggtt acaacaaacg accgttaacg gtacaaaagc agtgtcttat aaagggtcta   1740
atagaggaac aaaacgcaaa cgtaaaaatt gaggtctgac cgaaagtggt acatttttat   1800
aaacttttac acagtattca aagaatgttt gtttactctg actaagtata agtcttccaa   1860
ggataccgac cgcacccggt acactcagtc aagttgttgc caatatagaa tcagatcagt   1920
gccaaacaca ccgtcttgga ctcagaacag accgtgttcg ttataacatg ctcggattag   1980
ggacgtcgcc aaagaagatt taatctacaa tcgcttttgg caatcgcatt tggcactgct   2040
aaacgaccgt taacggtaag ttgcaatttt cttgtaccag gtgcggtatt aagatttcac   2100
aattgtaatg gttgttgcca actaccatag gcatattcaa gtttttgcct gtatcgtttt   2160
cgtatcctgt taacaatatc caatatatgt atacataaat aaatatatat atatataagt   2220
gtctgagatt gggttcttct gtaatcaggc aatggctgag ggagccgaac accaaccaaa   2280
actgacagaa aaagataagg cagaatttcc ttcaagtatt agagagttag ctgaaacctt   2340
aggcatccct ctgattgatt gtttaatacc ttgcaatttc tgtggcaaat ttctaaatta   2400
tttggaagct tgcgaattcg actacaaaaa acttagtcta atttggaaag attattgtgt   2460
gtttgcgtgc tgtcgcgtat gctgtggcgc cactgcaact tatgaattta accaatttta   2520
tgagcagaca gttttaggac gagatattga gttagcttca ggactttcga tttttgatat   2580
tgatatcagg tgtcaaactt gcttagcatt tcttgacatt atagaaaagt tagattgctg   2640
tggcagaggc cttccctttc ataaggtgag gaacgcctgg aagggaatct gtaggcagtg   2700
taagcatttt tatcatgatt ggtaaagagg tcaccgtgca agatattatt ctggagctca   2760
gtgaggtgca gcccgaagtg ctaccagttg acctgttttg tgaagaggaa ttaccaaacg   2820
agcaggaaac ggaggaggag cctgacaacg aaaggatctc ttacaaagtt atagctccgt   2880
gcggttgcag gaactgtgag gtcaagcttc gcatttttgt ccacgccaca gaatttggta   2940
ttagagcttt ccaacagcta ctgaccggag atctgcagct cctgtgcccc gactgtcgcg   3000
gaaactgcaa acatgacgga tcctaattct aaaggtagta catctaaaga agggtttggt   3060
gattggtgtt tattggaagc tgactgtagt gatgtagaaa atgatttggg acaattattt   3120
gagagagata cagactctga tatatcggat ttgttagatg atactgaact ggagcagggc   3180
```

-continued aattctttgg aactatttca tcaacaggag tgtgagcaga gcgaggagca attacaaaaa 3240
ctaaaacgaa agtatcttag tccaaaagct gtcgcacagc ttagtccgcg acttgagtca 3300
atttcattgt cacctcagca gaagtctaag cgaaggcttt ttgcagagca ggacagcgga 3360
ctcgagctga ctttaaacaa tgaagctgaa gatgttactc ctgaggtgga ggtaccggct 3420
attgactctc ggccggatga cgagggaggt tcaggggacg tagatataca ttttactgca 3480
ttgttgcgtt ctagcaacaa aaaagctaca ttaatggcta agtttaaaga gtcatttgga 3540
gtaggtttta atgaattgac acggcaattc aaaagccaca aaacctgctg taaagactgg 3600
gttgtctctg tatatgcagt gcatgatgat ttatttgaaa gctcaaagca gctgttgcaa 3660
cagcattgtg actatatctg ggtccgtggg ataggtgcaa tgtcattata tctattgtgt 3720
ttcaaggcgg gaaaaaatcg cgggacagtt cataagttaa ttacctcaat gttaaatgtg 3780
catgaacagc aaatattgtc tgagccgcca aaattgagaa acacagccgc tgcattgttc 3840
tggtataagg gttgtatggg atcgggggcg tttagccatg gaccatatcc tgattggatt 3900
gcccaacaaa ctatattagg tcacaaaagt gctgaggcaa gtacttttga tttttcagca 3960
atggtacaat gggcgtttga taatcattta ttagacgaag cagatatagc ataccagtat 4020
gcaaggcttg cacccgaaga tgcgaatgca gtagcttggc ttgcacataa caaccaggcc 4080
aaatttgtga gagaatgtgc ttatatggta cgattctata agaagggaca aatgagagac 4140
atgagcatat ctgaatggat atacactaaa atcaatgaag tagaagggga agggcactgg 4200
tcagatatag taaagtttat tagataccaa aatataaact ttattgtatt tctaactgca 4260
ttaaaagaat tcctacactc agtgccaaaa aaaaattgta ttttaattta tggtcctcca 4320
aattctggaa agtcatcatt tgcaatgtct ttaataagag tgttgaaggg tagggtgttg 4380
tcatttgtga actctaaaag tcagttttgg ctgcaacccc tttcagagtg caagatagct 4440
ctattggatg atgtaacaga cccttgttgg atatacatgg atacatattt aagaaatggc 4500
ttggatggac attatgtttc attagattgt aaatatagag ccccaacgca aatgaaattt 4560
cccccattat tattaacatc taacatcaat gtgcatgggg aaactaatta tagatattta 4620
cacagtagaa taaaaggatt tgaatttcca aatccttttc ctatgaaagc agataataca 4680
cctcagtttg aactaactga ccaaagctgg aaatcttttt ttacaaggct ttggacacaa 4740
ttagacctga gtgatcaaga agaggagggc gaggatggag aatctcagcg agcgtttcaa 4800
tgctctgcaa gatcagctaa tgaacattta tgaagccact tcgaaagttt atgatccaga 4860
acaaaggaaa cggatgataa ctggtccgca gtggtgggcc agatgtaaac aaatgaatgt 4920
tcttgattca tttattaatt attatgattc agaaaaacat gcagaaaatg ctgttatttt 4980
tttacatggt aacgcggcct cttcttattt atggcgacat gttgtgccac atattgagcc 5040
agtagcgcgg tgtattatac cagaccttat tggtatgggc aaatcaggca aatctggtaa 5100
tggttcttat aggttacttg atcattacaa atatcttact gcatggtttg aacttcttaa 5160
tttaccaaag aagatcattt ttgtcggcca tgattggggt gcttgtttgg catttcatta 5220
tagctatgag catcaagata agatcaaagc aatagttcac gctgaaagtg tagtagatgt 5280
gattgaatca tgggatgaat ggcctgatat tgaagaagat attgcgttga tcaaatctga 5340
agaaggagaa aaaatggttt tggagaataa cttcttcgtg gaaaccatgt tgccatcaaa 5400
aatcatgaga aagttagaac cagaagaatt tgcagcatat cttgaaccat tcaaagagaa 5460
aggtgaagtt cgtcgtccaa cattatcatg gcctcgtgaa atcccgttag taaaaggtgg 5520

```
taaacctgac gttgtacaaa ttgttaggaa ttataatgct tatctacgtg caagtgatga   5580
tttaccaaaa atgtttattg aatcggaccc aggattcttt tccaatgcta ttgttgaagg   5640
tgccaagaag tttcctaata ctgaatttgt caaagtaaaa ggtcttcatt tttcgcaaga   5700
agatgcacct gatgaaatgg gaaaatatat caaatcgttc gttgagcgag ttctcaaaaa   5760
tgaacaagca ccggtgaaac agactttgaa ttttgacctt ctcaagttgg cgggagacgt   5820
ggagtccaac cctgggccca tggagaatct cagcgagcgt ttcaatgctc tgcaagatca   5880
gctaatgaac atttatgaag ctgcagaaca aacattgcag gcacaaatta aacattggca   5940
aaccttacga aaagaagctg tattactcta ctatgctagg gagaaaggtg ttacaaggct   6000
tggatatcaa cctgtgcctg taaaggcagt atcagaaaca aaggctaaag aagccatagc   6060
aatggtgctg cagcttgagt cactacagac gtctgatttt gctcatgagc catggactct   6120
agttgatacc agcatagaaa catttagaag cgctccagaa ggtcacttca aaaaaggccc   6180
cgtccctgta gaagttattt atgacaatga tccagataat gccaatttgt atacaatgtg   6240
gacctatgtg tattatatgg atgcggatga taagtggcat aaggcaagaa gtggggtgaa   6300
tcacattggc atttattatt tacaaggaac gtttaaaaac tattatgtac tgtttgctga   6360
cgatgcaaaa agatatggta caactggaga atgggaagta aaagttaata aggaaactgt   6420
gtttgctcct gtcaccagct ccacgcctcc agggtcgcca ggaggacaag cagacacaaa   6480
caccacctcc gcgaccccca ccacctccac aaccgccgtt gactccacgt ccagacagct   6540
cactacatca aaacagccac aacaaaccga aaccagagga agaaggtacg gacggagggc   6600
ctccagcaag tcaaggagat cgcaaacgca gcaaaggcga tcaaggtccc gacaccggtc   6660
ccggtctcgg tcccggtcgc ggtccaagtc caaaacccac accactcggt ccaccaccag   6720
gtcccggtcc acgtcgctca ccaagactcg ggcccttaca agcagatcgc gatccagagg   6780
aaggtcccca accacctgca gaaggggagg tggaaggtca cccaggcggc gatcaaggtc   6840
accctccacc tcctcctcct gcaccacaca acggtcacag cgggcacggg ccgaaagttc   6900
aacaaccaga ggggcccgag ggtcgagagg gtcacgagga gggagccgtg gggggagagg   6960
gcggcgacga ggaaggtcat cctcctcctc ctcccccacc cacaaacggt cacgagggga   7020
atctgctaag ctccgtggcg tctctcctgg tgaagtggga gggtcacttc gatcagttag   7080
ttcaaagcat acaggtcgac ttggaagatt actggaagaa gctcgcgacc ccccagtaat   7140
cattgtcaaa ggggcggcta acacactgaa atgcttccgc aacagagcta aaattacata   7200
caagggactg tttaggtcat ttagcactac ctggtcatgg gtggcaggag atggcactga   7260
gcgtctaggc aggcccagaa tgctcattag cttttcttca tatactcaaa ggagagattt   7320
tgatgaagcg gtacgatacc ctaaaggagt tgataaggcc tatggcaacc tggacagtct   7380
ttaacattta ctaatgctgc ttctgctact aacatattaa cataccctag cattttatat   7440
tttttttac attttgtatt tgctatggcg cgtgctagaa gggtcaagcg agactctgta   7500
actcatattt accaaacctg caaacaggca ggcacttgcc cccctgatgt tattaataaa   7560
gtggaacaaa caacagttgc tgacaatatt ttaaaatatg gcagtgctgg tgtatttttt   7620
ggtggccttg gtattagtac aggccgagga actgggggtg ctacagggta cgtgccactt   7680
ggggaaggtc ctggtgtccg tgtcggagga acccccacgg ttgtaaggcc ttccttggtt   7740
cctgaaacaa tcgggcccgt tgatattttg cccattgata cagttaaccc cgtggaacct   7800
acagcatcat ccgtggtccc tttaactgag tccacaggcg ctgatttact tccaggtgaa   7860
gtagaaacaa ttgctgaaat tcatcctgta cctgaagggc catcagtaga tactcctgta   7920
```

-continued gttaccacta gcacaggttc cagtgctgtt ttagaggttt ccccagagcc tattcctcca 7980
acacgggtca gagtttcacg aacacaatat cacaatccat cttttcaaat aataactgag 8040
tctactccag cacaagggga atcgtctctt gcagatcacg ttttggtgac atcgggttct 8100
ggggggcaac gaataggggg tgatataact gacataattg agttagagga aatccctagt 8160
aggtatacat ttgaaattga agaaccaact cctccacgcc gcagcagtac tccattgtca 8220
cgcactcaat ctgtaggccg taggaggggt ttgtcgttga ctaatagacg tttggtacag 8280
caggtacaag tggacaatcc attgtttcta actcaaccat ctaagttagt tcgttttgca 8340
tttgataatc ctgtttttga ggaagaagtg actaatatat ttgaaaatga tctggatgtc 8400
tttgaagaac ctccagacag agattttctt gatgttagaa aattgggacg tccacaatat 8460
tctacaacac cagcgggata tgtcagagta agcaggttgg ggactcgagc cactattcgc 8520
actcgctctg gtgcacaaat agggtcgcaa gtccattttt acagagatct tagctctatt 8580
aatactgagg atcctattga attacaatta ttaggccaac attcaggtga tgctactata 8640
gtccagggac ctgttgaaag cacatttata gatatggata tttctgaaaa tccattatct 8700
gaaagcatcg aagcatattc acatgattta ttattagatg aggcggtgga agatttcagt 8760
gggtctcagc tggttatagg taatcgaagg agcacaaatt cttacactgt tc 8812

<210> SEQ ID NO 3
<211> LENGTH: 13024
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(13024)
<223> OTHER INFORMATION: pMC_HPV18-Rluc-E2

<400> SEQUENCE: 3
attaatactt ttaacaattg tagtatataa aaaagggagt aaccgaaaac ggtcgggacc 60
gaaaacggtg tatataaaag atgtgagaaa cacaccacaa tactatggcg cgctttgagg 120
atccaacacg gcgaccctac aagctacctg atctgtgcac ggaactgaac acttcactgc 180
aagacataga aataacctgt gtatattgca agacagtatt ggaacttaca gaggtatttg 240
aatttgcatt taaagattta tttgtggtgt atagagacag tataccgcat gctgcatgcc 300
ataaatgtat agatttttat tctagaatta gagaattaag acattattca gactctgtgt 360
atggagacac attggaaaaa ctaactaaca ctgggttata caatttatta ataaggtgcc 420
tgcggtgcca gaaaccgttg aatccagcag aaaaacttag acaccttaat gaaaaacgac 480
gatttcacaa catagctggg cactatagag gccagtgcca ttcgtgctgc aaccgagcac 540
gacaggaacg actccaacga cgcagagaaa cacaagtata atattaagta tgcatggacc 600
taaggcaaca ttgcaagaca ttgtattgca tttagagccc caaaatgaaa ttccggttga 660
ccttctatgt cacgagcaat taagcgactc agaggaagaa aacgatgaaa tagatggagt 720
taatcatcaa catttaccag cccgacgagc cgaaccacaa cgtcacacaa tgttgtgtat 780
gtgttgtaag tgtgaagcca gaattgagct agtagtagaa agctcagcag acgaccttcg 840
agcattccag cagctgtttc tgaacaccct gtcctttgtg tgtccgtggt gtgcatccca 900
gcagtaagca acaatggctg atccagaagg tacagacggg gagggcacgg gttgtaacgg 960
ctggttttat gtacaagcta ttgtagacaa aaaaacagga gatgtaatat cagatgacga 1020

```
ggacgaaaat gcaacagaca cagggtcgga tatggtagat tttattgata cacaaggaac   1080
attttgtgaa caggcagagc tagagacagc acaggcattg ttccatgcgc aggaggtcca   1140
caatgatgca caagtgttgc atgttttaaa acgaaagttt gcaggaggca gcacagaaaa   1200
cagtccatta ggggagcggc tggaggtgga tacagagtta agtccacggt tacaagaaat   1260
atctttaaat agtgggcaga aaaaggcaaa aaggcggctg tttacaatat cagatagtgg   1320
ctatggctgt tctgaagtgg aagcaacaca gattcaggta actacaaatg gcgaacatgg   1380
cggcaatgta tgtagtggcg gcagtacgga ggctatagac aacgggggca cagagggcaa   1440
caacagcagt gtagacggta caagtgacaa tagcaatata gaaaatgtaa atccacaatg   1500
taccatagca caattaaaag acttgttaaa agtaaacaat aaacaaggag ctatgttagc   1560
agtatttaaa gacacatatg ggctatcatt tacagattta gttagaaatt ttaaaagtga   1620
taaaaccacg tgtacagatt gggttacagc tatatttgga gtaaacccaa caatagcaga   1680
aggatttaaa acactaatac agccatttat attatatgcc catattcaat gtctagactg   1740
taaatgggga gtattaatat tagccctgtt gcgttacaaa tgtggtaaga gtagactaac   1800
agttgctaaa ggtttaagta cgttgttaca cgtacctgaa acttgtatgt taattcaacc   1860
accaaaattg cgaagtagtg ttgcagcact atattggtat agaacaggaa tatcaaatat   1920
tagtgaagta atgggagaca cacctgagtg gatacaaaga cttactatta tacaacatgg   1980
aatagatgat agcaattttg atttgtcaga aatggtacaa tgggcatttg ataatgagct   2040
gacagatgaa agcgatatgg catttgaata tgccttatta gcagacagca acagcaatgc   2100
agctgccttt ttaaaaagca attgccaagc taaatattta aaagattgtg ccacaatgtg   2160
caaacattat aggcgagccc aaaaacgaca aatgaatatg tcacagtgga tacgatttag   2220
atgttcaaaa atagatgaag gggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagttgcgt gcaggacaaa atcatagacc   2880
actatgaagc cacttcgaaa gtttatgatc cagaacaaag gaaacggatg ataactggtc   2940
cgcagtggtg ggccagatgt aaacaaatga atgttcttga ttcatttatt aattattatg   3000
attcagaaaa acatgcagaa aatgctgtta ttttttttaca tggtaacgcg gcctcttctt   3060
atttatggcg acatgttgtg ccacatattg agccagtagc gcggtgtatt ataccagacc   3120
ttattggtat gggcaaatca ggcaaatctg gtaatggttc ttataggtta cttgatcatt   3180
acaaatatct tactgcatgg tttgaacttc ttaatttacc aaagaagatc atttttgtcg   3240
gccatgattg ggtgcttgt ttggcatttc attatagcta tgagcatcaa gataagatca   3300
aagcaatagt tcacgctgaa agtgtagtag atgtgattga atcatgggat gaatggcctg   3360
atattgaaga agatattgcg ttgatcaaat ctgaagaagg agaaaaaatg gttttggaga   3420
```

-continued ataacttctt cgtggaaacc atgttgccat caaaaatcat gagaaagtta gaaccagaag 3480
aatttgcagc atatcttgaa ccattcaaag agaaaggtga agttcgtcgt ccaacattat 3540
catggcctcg tgaaatcccg ttagtaaaag gtggtaaacc tgacgttgta caaattgtta 3600
ggaattataa tgcttatcta cgtgcaagtg atgatttacc aaaaatgttt attgaatcgg 3660
acccaggatt cttttccaat gctattgttg aaggtgccaa gaagtttcct aatactgaat 3720
ttgtcaaagt aaaaggtctt catttttcgc aagaagatgc acctgatgaa atgggaaaat 3780
atatcaaatc gttcgttgag cgagttctca aaaatgaaca agcaccggtg aaacagactt 3840
tgaattttga ccttctcaag ttggcgggag acgtggagtc caaccctggg cccatgcaga 3900
caccgaagga aaccctttcg gaacgtttaa gtgcgttgca ggacaaaatc atagaccact 3960
atgaaaatga cagtaaagac atagacagcc aaatacagta ttggcaacta atacgttggg 4020
aaaatgcaat attctttgca gcaagggaac atggcataca gacattaaac caccaggtgg 4080
tgccagccta taacatttca aaaagtaaag cacataaagc tattgaactg caaatggccc 4140
tacaaggcct tgcacaaagt gcatacaaaa ccgaggattg gacactgcaa gacacatgcg 4200
aggaactatg gaatacagaa cctactcact gctttaaaaa aggtggccaa acagtacaag 4260
tatattttga tggcaacaaa gacaattgta tgacctatgt agcatgggac agtgtgtatt 4320
atatgactga tgcaggaaca tgggacaaaa cggctacctg tgtaagtcac aggggattgt 4380
attatgtaaa ggaagggtac aacacgtttt atatagaatt taaaagtgaa tgtgaaaaat 4440
atgggaacac aggtacgtgg gaagtacatt ttgggaataa tgtaattgat tgtaatgact 4500
ctatgtgcag taccagtgac gacacggtat ccgctactca gcttgttaaa cagctacagc 4560 acacccccctc accgtattcc agcaccgtgt ccgtgggcac cgcaaagacc tacggccaga 4620
cgtcggctgc tacacgacct ggacactgtg gactcgcgga gaagcagcat tgtggacctg 4680
tcaacccact tctcggtgca gctacaccta caggcaacaa caaaagacgg aaactctgta 4740
gtggtaacac tacgcctata atacatttaa aaggtgacag aaacagttta aaatgtttac 4800
ggtacagatt gcgaaaacat agcgaccact atagagatat atcatccacc tggcattgga 4860
caggtgcagg caatgaaaaa acaggaatac tgactgtaac ataccatagt gaaacacaaa 4920
gaacaaaatt tttaaatact gttgcaattc cagatagtgt acaaatattg gtgggataca 4980
tgacaatgta atacatatgc tgtagtacca atatgttatc acttattttt ttattttgct 5040
tttgtgtatg catgtatgtg tgctgccatg tcccgctttt gccatctgtc tgtatgtgtg 5100
cgtatgcatg ggtattggta tttgtgtata ttgtggtaat aacgtcccct gccacagcat 5160
tcacagtata tgtattttgt tttttattgc ccatgttact attgcatata catgctatat 5220
tgtctttaca gtaattgtat aggttgtttt atacagtgta ttgtacattg tatattttgt 5280
tttatacctt ttatgctttt tgtatttttg taataaaagt atggtatccc accgtgccgc 5340
acgacgcaaa cgggcttcgg taactgactt atataaaaca tgtaaacaat ctggtacatg 5400
tccacctgat gttgttccta aggtggaggg caccacgtta gcagataaaa tattgcaatg 5460
gtcaagcctt ggtatatttt tgggtggact tggcataggt actggcagtg gtacaggggg 5520
tcgtacaggg tacattccat tgggtgggcg ttccaataca gtggtggatg ttggtcctac 5580
acgtccccca gtggttattg aacctgtggg ccccacagac ccatctattg ttacattaat 5640
agaggactcc agtgtggtta catcaggtgc acctaggcct acgtttactg gcacgtctgg 5700
gtttgatata acatctgcgg gtacaactac acctgcggtt ttggatatca caccttcgtc 5760

-continued

```
tacctctgtg tctatttcca caaccaattt taccaatcct gcattttctg atccgtccat   5820
tattgaagtt ccacaaactg gggaggtggc aggtaatgta tttgttggta cccctacatc   5880
tggaacacat gggtatgagg aaataccttt acaaacattt gcttcttctg gtacgggggga  5940
ggaacccatt agtagtaccc cattgcctac tgtgcggcgt gtagcaggtc cccgccttta   6000
cagtagggcc taccaacaag tgtcagtggc taaccctgag tttcttacac gtccatcctc   6060
tttaattaca tatgacaacc cggcctttga gcctgtggac actacattaa catttgatcc   6120
tcgtagtgat gttcctgatt cagattttat ggatattatc cgtctacata ggcctgcttt   6180
aacatccagg cgtgggactg ttcgctttag tagattaggt caacgggcaa ctatgtttac   6240
ccgcagcggt acacaaatag gtgctagggt tcacttttat catgatataa gtcctattgc   6300
accttcccca gaatatattg aactgcagcc tttagtatct gccacggagg acaatgactt   6360
gtttgatata tatgcagatg acatggaccc tgcagtgcct gtaccatcgc gttctactac   6420
ctcctttgca ttttttaaat attcgcccac tatatcttct gcctcttcct atagtaatgt   6480
aacggtccct ttaacctcct cttgggatgt gcctgtatac acgggtcctg atattacatt   6540
accatctact acctctgtat ggcccattgt atcacccacg gcccctgcct ctacacagta   6600
tattggtata catggtacac attattattt gtggccatta tattatttta ttcctaagaa   6660
acgtaaacgt gttccctatt tttttgcaga tggctttgtg gcggcctagt gacaataccg   6720
tatatcttcc acctccttct gtggcaagag ttgtaaatac cgatgattat gtgactcgca   6780
caagcatatt ttatcatgct ggcagctcta gattattaac tgttggtaat ccatatttta   6840
gggttcctgc aggtggtggc aataagcagg atattcctaa ggtttctgca taccaatata   6900
gagtatttag ggtgcagtta cctgacccaa ataaatttgg tttacctgat actagtattt   6960
ataatcctga aacacaacgt ttagtgtggg cctgtgctgg agtggaaatt ggccgtggtc   7020
agcctttagg tgttggcctt agtgggcatc cattttataa taaattagat gacactgaaa   7080
gttcccatgc cgccacgtct aatgtttctg aggacgttag ggacaatgtg tctgtagatt   7140
ataagcagac acagttatgt attttgggct gtgcccctgc tattggggaa cactgggcta   7200
aaggcactgc ttgtaaatcg cgtcctttat cacagggcga ttgcccccct ttagaactta   7260
aaaacacagt tttggaagat ggtgatatgg tagatactgg atatggtgcc atggacttta   7320
gtacattgca agatactaaa tgtgaggtac cattggatat ttgtcagtct atttgtaaat   7380
atcctgatta tttacaaatg tctgcagatc cttatgggga ttccatgttt ttttgcttac   7440
ggcgtgagca gctttttgct aggcattttt ggaatagagc aggtactatg ggtgacactg   7500
tgcctcaatc cttatatatt aaaggcacag gtatgcgtgc ttcacctggc agctgtgtgt   7560
attctccctc tccaagtggc tctattgtta cctctgactc ccagttgttt aataaaccat   7620
attggttaca taaggcacag ggtcataaca atggtgtttg ctggcataat caattatttg   7680
ttactgtggt agataccact cgcagtacca atttaacaat atgtgcttct acacagtctc   7740
ctgtacctgg gcaatatgat gctaccaaat ttaagcagta tagcagacat gttgaggaat   7800
atgatttgca gtttattttt cagttgtgta ctattacttt aactgcagat gttatgtcct   7860
atattcatag tatgaatagc agtattttag aggattggaa ctttggtgtt ccccccccgc   7920
caactactag tttggtggat acatatcgtt ttgtacaatc tgttgctatt acctgtcaaa   7980
aggatgctgc accggctgaa aataaggatc cctatgataa gttaaagttt tggaatgtgg   8040
atttaaagga aaagttttct ttagacttag atcaatatcc ccttggacgt aaatttttgg   8100
ttcaggctgg attgcgtcgc aagcccacca taggccctcg caaacgttct gctccatctg   8160
```

ccactacgtc ttctaaacct gccaagcgtg tgcgtgtacg tgccaggaag taatatgtgt 8220
gtgtgtatat atatatacat ctattgttgt gtttgtatgt cctgtgtttg tgtttgttgt 8280
atgattgcat tgtatggtat gtatggttgt tgttgtatgt tgtatgttac tatatttgtt 8340
ggtatgtggc attaaataaa atatgttttg tggttctgtg tgttatgtgg ttgcgcccta 8400
gtgagtaaca actgtatttg tgtttgtggt atgggtgttg cttgttgggc tatatattgt 8460
cctgtatttc aagttataaa actgcacacc ttacagcatc cattttatcc tacaatcctc 8520
cattttgctg tgcaaccgat ttcggttgcc agatctgata tctctagagt cgacccatgg 8580
gggcccgccc caactggggt aacctttgag ttctctcagt tgggggtaat cagcatcatg 8640
atgtggtacc acatcatgat gctgattata agaatgcggc cgccacactc tagtggatct 8700
cgagttaata attcagaaga actcgtcaag aaggcgatag aaggcgatgc gctgcgaatc 8760
gggagcggcg ataccgtaaa gcacgaggaa gcggtcagcc cattcgccgc caagctcttc 8820
agcaatatca cgggtagcca acgctatgtc ctgatagcgg tccgccacac ccagccggcc 8880
acagtcgatg aatccagaaa agcggccatt ttccaccatg atattcggca agcaggcatc 8940
gccatgggtc acgacgagat cctcgccgtc gggcatgctc gccttgagcc tggcgaacag 9000
ttcggctggc gcgagcccct gatgctcttc gtccagatca tcctgatcga caagaccggc 9060
ttccatccga gtacgtgctc gctcgatgcg atgtttcgct tggtggtcga atgggcaggt 9120
agccggatca agcgtatgca gccgccgcat tgcatcagcc atgatggata ctttctcggc 9180
aggagcaagg tgtagatgac atggagatcc tgccccggca cttcgcccaa tagcagccag 9240
tcccttcccg cttcagtgac aacgtcgagc acagctgcgc aaggaacgcc cgtcgtggcc 9300
agccacgata gccgcgctgc ctcgtcttgc agttcattca gggcaccgga caggtcggtc 9360
ttgacaaaaa gaaccgggcg cccctgcgct gacagccgga acacggcggc atcagagcag 9420
ccgattgtct gttgtgccca gtcatagccg aatagcctct ccacccaagc ggccggagaa 9480
cctgcgtgca atccatcttg ttcaatcatg cgaaacgatc ctcatcctgt ctcttgatca 9540
gagcttgatc ccctgcgcca tcagatcctt ggcggcgaga aagccatcca gtttactttg 9600
cagggcttcc caaccttacc agagggcgcc ccagctggca attccggttc gcttgctgtc 9660
cataaaaccg cccagtctag ctatcgccat gtaagcccac tgcaagctac ctgctttctc 9720
tttgcgcttg cgttttccct tgtccagata gcccagtagc tgacattcat ccggggtcag 9780
caccgtttct gcggactggc tttctacgtg ctcgaggggg gccaaacggt ctccagcttg 9840
gctgttttgg cggatgagag aagattttca gcctgataca gattaaatca gaacgcagaa 9900
gcggtctgat aaaacagaat ttgcctggcg gcagtagcgc ggtggtccca cctgacccca 9960
tgccgaactc agaagtgaaa cgccgtagcg ccgatggtag tgtggggtct ccccatgcga 10020
gagtagggaa ctgccaggca tcaaataaaa cgaaaggctc agtcgaaaga ctgggccttt 10080
cgttttatct gttgtttgtc ggtgaacgct ctcctgagta ggacaaatcc gccgggagcg 10140
gatttgaacg ttgcgaagca acggcccgga gggtggcggg caggacgccc gccataaact 10200
gccaggcatc aaattaagca gaaggccatc ctgacggatg gcctttttgc gtttctacaa 10260
actcttttgt ttatttttct aaatacattc aaatatgtat ccgctcatga ccaaaatccc 10320
ttaacgtgag ttttcgttcc actgagcgtc agaccccgta gaaaagatca aaggatcttc 10380
ttgagatcct ttttttctgc gcgtaatctg ctgcttgcaa acaaaaaaac caccgctacc 10440
agcggtggtt tgtttgccgg atcaagagct accaactctt tttccgaagg taactggctt 10500

-continued

```
cagcagagcg cagataccaa atactgtcct tctagtgtag ccgtagttag gccaccactt  10560
caagaactct gtagcaccgc ctacatacct cgctctgcta atcctgttac cagtggctgc  10620
tgccagtggc gataagtcgt gtcttaccgg gttggactca agacgatagt taccggataa  10680
ggcgcagcgg tcgggctgaa cggggggttc gtgcacacag cccagcttgg agcgaacgac  10740
ctacaccgaa ctgagatacc tacagcgtga gctatgagaa agcgccacgc ttcccgaagg  10800
gagaaaggcg gacaggtatc cggtaagcgg cagggtcgga acaggagagc gcacgaggga  10860
gcttccaggg ggaaacgcct ggtatcttta tagtcctgtc gggtttcgcc acctctgact  10920
tgagcgtcga tttttgtgat gctcgtcagg ggggcggagc ctatggaaaa acgccagcaa  10980
cgcggccttt ttacggttcc tggccttttg ctggcctttt gctcacatgt tctttcctgc  11040
gttatcccct gattctgtgg ataaccgtat taccgccttt gagtgagctg ataccgctcg  11100
ccgcagccga acgaccgagc gcagcgagtc agtgagcgag gaagcggaag agcgcctgat  11160
gcggtatttt ctccttacgc atctgtgcgg tatttcacac cgcatatggt gcactctcag  11220
tacaatctgc tctgatgccg catagttaag ccagtataca ctccgctatc gctacgtgac  11280
tgggtcatgg ctgcgccccg acacccgcca acacccgctg acgcgccctg acgggcttgt  11340
ctgctcccgg catccgctta cagacaagct gtgaccgtct ccgggagctg catgtgtcag  11400
aggttttcac cgtcatcacc gaaacgcgcg aggcagcaga tcaattcgcg cgcgaaggcg  11460
aagcggcatg cataatgtgc ctgtcaaatg gacgaagcag ggattctgca aaccctatgc  11520
tactccgtca agccgtcaat tgtctgattc gttaccaatt atgacaactt gacggctaca  11580
tcattcactt tttcttcaca accggcacgg aactcgctcg ggctggcccc ggtgcatttt  11640
ttaaataccc gcgagaaata gagttgatcg tcaaaaccaa cattgcgacc gacggtggcg  11700
ataggcatcc gggtggtgct caaaagcagc ttcgcctggc tgatacgttg gtcctcgcgc  11760
cagcttaaga cgctaatccc taactgctgg cggaaaagat gtgacagacg cgacggcgac  11820
aagcaaacat gctgtgcgac gctggcgata cattaccctg ttatccctag atgacattac  11880
cctgttatcc cagatgacat taccctgtta tccctagatg acattaccct gttatcccta  11940
gatgacattt accctgttat ccctagatga cattaccctg ttatcccaga tgacattacc  12000
ctgttatccc tagatacatt accctgttat cccagatgac ataccctgtt atccctagat  12060
gacattaccc tgttatccca gatgacatta ccctgttatc cctagataca ttaccctgtt  12120
atcccagatg acataccctg ttatccctag atgacattac cctgttatcc cagatgacat  12180
taccctgtta tccctagata cattaccctg ttatcccaga tgacataccc tgttatccct  12240
agatgacatt accctgttat cccagatgac attaccctgt tatccctaga tacattaccc  12300
tgttatccca gatgacatac cctgttatcc ctagatgaca ttaccctgtt atcccagatg  12360
acattaccct gttatcccta gatacattac cctgttatcc cagatgacat accctgttat  12420
ccctagatga cattaccctg ttatcccaga tgacattacc ctgttatccc tagatacatt  12480
accctgttat cccagatgac ataccctgtt atccctagat gacattaccc tgttatccca  12540
gataaactca atgatgatga tgatgatggt cgagactcag cggccgcggt gccagggcgt  12600
gcccttgggc tccccgggcg cgactagtga attcagatct tttggcttat gtctgtggtt  12660
ttctgcacaa tacagtacgc tggcactatt gcaaacttta atcttttggg cactgctcct  12720
acatattttg aacaattggc gcgcctcttt ggcgcatata aggcgcacct ggtattagtc  12780
attttcctgt ccaggtgcgc tacaacaatt gcttgcataa ctatatccac tccctaagta  12840
ataaaactgc ttttaggcac atattttagt ttgtttttac ttaagctaat tgcatacttg  12900
```

gcttgtacaa ctactttcat gtccaacatt ctgtctaccc ttaacatgaa ctataatatg 12960
actaagctgt gcatacatag tttatgcaac cgaaataggt tgggcagcac atactatact 13020
tttc 13024

<210> SEQ ID NO 4
<211> LENGTH: 9025
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(9025)
<223> OTHER INFORMATION: HPV18-Rluc-E2 marker genome

<400> SEQUENCE: 4
attaatactt ttaacaattg tagtatataa aaaagggagt aaccgaaaac ggtcgggacc 60
gaaaacggtg tatataaaag atgtgagaaa cacaccacaa tactatggcg cgctttgagg 120
atccaacacg gcgaccctac aagctacctg atctgtgcac ggaactgaac acttcactgc 180
aagacataga aataacctgt gtatattgca agacagtatt ggaacttaca gaggtatttg 240
aatttgcatt taaagattta tttgtggtgt atagagacag tataccgcat gctgcatgcc 300
ataaatgtat agatttttat tctagaatta gagaattaag acattattca gactctgtgt 360
atggagacac attggaaaaa ctaactaaca ctgggttata caatttatta ataaggtgcc 420
tgcggtgcca gaaaccgttg aatccagcag aaaaacttag acaccttaat gaaaaacgac 480
gatttcacaa catagctggg cactatagag gccagtgcca ttcgtgctgc aaccgagcac 540
gacaggaacg actccaacga cgcagagaaa cacaagtata atattaagta tgcatggacc 600
taaggcaaca ttgcaagaca ttgtattgca tttagagccc caaaatgaaa ttccggttga 660
ccttctatgt cacgagcaat taagcgactc agaggaagaa aacgatgaaa tagatggagt 720
taatcatcaa catttaccag cccgacgagc cgaaccacaa cgtcacacaa tgttgtgtat 780
gtgttgtaag tgtgaagcca gaattgagct agtagtagaa agctcagcag acgaccttcg 840
agcattccag cagctgtttc tgaacaccct gtcctttgtg tgtccgtggt gtgcatccca 900
gcagtaagca acaatggctg atccagaagg tacagacggg gagggcacgg gttgtaacgg 960
ctggttttat gtacaagcta ttgtagacaa aaaaacagga gatgtaatat cagatgacga 1020
ggacgaaaat gcaacagaca cagggtcgga tatggtagat tttattgata cacaaggaac 1080
attttgtgaa caggcagagc tagagacagc acaggcattg ttccatgcgc aggaggtcca 1140
caatgatgca caagtgttgc atgttttaaa acgaaagttt gcaggaggca gcacagaaaa 1200
cagtccatta ggggagcggc tggaggtgga tacagagtta agtccacggt tacaagaaat 1260
atctttaaat agtgggcaga aaaaggcaaa aaggcggctg tttacaatat cagatagtgg 1320
ctatggctgt tctgaagtgg aagcaacaca gattcaggta actacaaatg gcgaacatgg 1380
cggcaatgta tgtagtggcg gcagtacgga ggctatagac aacgggggca cagagggcaa 1440
caacagcagt gtagacggta caagtgacaa tagcaatata gaaaatgtaa atccacaatg 1500
taccatagca caattaaaag acttgttaaa agtaaacaat aaacaaggag ctatgttagc 1560
agtatttaaa gacacatatg ggctatcatt tacagattta gttagaaatt ttaaaagtga 1620
taaaaccacg tgtacagatt gggttacagc tatatttgga gtaaacccaa caatagcaga 1680
aggatttaaa acactaatac agccatttat attatatgcc catattcaat gtctagactg 1740

-continued

```
taaatgggga gtattaatat tagccctgtt gcgttacaaa tgtggtaaga gtagactaac   1800
agttgctaaa ggtttaagta cgttgttaca cgtacctgaa acttgtatgt taattcaacc   1860
accaaaattg cgaagtagtg ttgcagcact atattggtat agaacaggaa tatcaaatat   1920
tagtgaagta atgggagaca cacctgagtg gatacaaaga cttactatta tacaacatgg   1980
aatagatgat agcaatttg atttgtcaga aatggtacaa tgggcatttg ataatgagct   2040
gacagatgaa agcgatatgg catttgaata tgccttatta gcagacagca acagcaatgc   2100
agctgccttt ttaaaaagca attgccaagc taaatattta aaagattgtg ccacaatgtg   2160
caaacattat aggcgagccc aaaaacgaca aatgaatatg tcacagtgga tacgatttag   2220
atgttcaaaa atagatgaag gggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagttgcgt gcaggacaaa atcatagacc   2880
actatgaagc cacttcgaaa gtttatgatc cagaacaaag gaaacggatg ataactggtc   2940
cgcagtggtg ggccagatgt aaacaaatga atgttcttga ttcatttatt aattattatg   3000
attcagaaaa acatgcagaa aatgctgtta tttttttaca tggtaacgcg gcctcttctt   3060
atttatggcg acatgttgtg ccacatattg agccagtagc gcggtgtatt ataccagacc   3120
ttattggtat gggcaaatca ggcaaatctg gtaatggttc ttataggtta cttgatcatt   3180
acaaatatct tactgcatgg tttgaacttc ttaatttacc aaagaagatc atttttgtcg   3240
gccatgattg gggtgcttgt ttggcatttc attatagcta tgagcatcaa gataagatca   3300
aagcaatagt tcacgctgaa agtgtagtag atgtgattga atcatgggat gaatggcctg   3360
atattgaaga agatattgcg ttgatcaaat ctgaagaagg agaaaaaatg gttttggaga   3420
ataacttctt cgtggaaacc atgttgccat caaaaatcat gagaaagtta gaaccagaag   3480
aatttgcagc atatcttgaa ccattcaaag agaaaggtga agttcgtcgt ccaacattat   3540
catggcctcg tgaaatcccg ttagtaaaag gtggtaaacc tgacgttgta caaattgtta   3600
ggaattataa tgcttatcta cgtgcaagtg atgatttacc aaaaatgttt attgaatcgg   3660
acccaggatt cttttccaat gctattgttg aaggtgccaa gaagtttcct aatactgaat   3720
ttgtcaaagt aaaaggtctt cattttttcgc aagaagatgc acctgatgaa atgggaaaat   3780
atatcaaatc gttcgttgag cgagttctca aaaatgaaca agcaccggtg aaacagactt   3840
tgaattttga ccttctcaag ttggcgggag acgtggagtc caaccctggg cccatgcaga   3900
caccgaagga aaccctttcg gaacgtttaa gtgcgttgca ggacaaaatc atagaccact   3960
atgaaaatga cagtaaagac atagacagcc aaatacagta ttggcaacta atacgttggg   4020
aaaatgcaat attctttgca gcaagggaac atggcataca gacattaaac caccaggtgg   4080
tgccagccta taacatttca aaaagtaaag cacataaagc tattgaactg caaatggccc   4140
```

tacaaggcct tgcacaaagt gcatacaaaa ccgaggattg gacactgcaa gacacatgcg 4200
aggaactatg gaatacagaa cctactcact gctttaaaaa aggtggccaa acagtacaag 4260
tatattttga tggcaacaaa gacaattgta tgacctatgt agcatgggac agtgtgtatt 4320
atatgactga tgcaggaaca tgggacaaaa cggctacctg tgtaagtcac aggggattgt 4380
attatgtaaa ggaagggtac aacacgtttt atatagaatt taaaagtgaa tgtgaaaaat 4440
atgggaacac aggtacgtgg gaagtacatt ttgggaataa tgtaattgat tgtaatgact 4500
ctatgtgcag taccagtgac gacacggtat ccgctactca gcttgttaaa cagctacagc 4560
acaccccctc accgtattcc agcaccgtgt ccgtgggcac cgcaaagacc tacggccaga 4620
cgtcggctgc tacacgacct ggacactgtg gactcgcgga gaagcagcat tgtggacctg 4680
tcaacccact tctcggtgca gctacaccta caggcaacaa caaaagacgg aaactctgta 4740
gtggtaacac tacgcctata atacatttaa aaggtgacag aaacagttta aaatgtttac 4800
ggtacagatt gcgaaaacat agcgaccact atagagatat atcatccacc tggcattgga 4860
caggtgcagg caatgaaaaa acaggaatac tgactgtaac ataccatagt gaaacacaaa 4920
gaacaaaatt tttaaatact gttgcaattc cagatagtgt acaaatattg gtgggataca 4980
tgacaatgta atacatatgc tgtagtacca atatgttatc acttattttt ttattttgct 5040
tttgtgtatg catgtatgtg tgctgccatg tcccgctttt gccatctgtc tgtatgtgtg 5100
cgtatgcatg ggtattggta tttgtgtata ttgtggtaat aacgtcccct gccacagcat 5160
tcacagtata tgtattttgt tttttattgc ccatgttact attgcatata catgctatat 5220
tgtctttaca gtaattgtat aggttgtttt atacagtgta ttgtacattg tatattttgt 5280
tttatacctt ttatgctttt tgtatttttg taataaaagt atggtatccc accgtgccgc 5340
acgacgcaaa cgggcttcgg taactgactt atataaaaca tgtaaacaat ctggtacatg 5400
tccacctgat gttgttccta aggtggaggg caccacgtta gcagataaaa tattgcaatg 5460
gtcaagcctt ggtatatttt tgggtggact tggcataggt actggcagtg gtacaggggg 5520
tcgtacaggg tacattccat tgggtgggcg ttccaataca gtggtggatg ttggtcctac 5580
acgtccccca gtggttattg aacctgtggg ccccacagac ccatctattg ttacattaat 5640
agaggactcc agtgtggtta catcaggtgc acctaggcct acgtttactg gcacgtctgg 5700
gtttgatata acatctgcgg gtacaactac acctgcggtt ttggatatca caccttcgtc 5760
tacctctgtg tctatttcca caaccaattt taccaatcct gcattttctg atccgtccat 5820
tattgaagtt ccacaaactg gggaggtggc aggtaatgta tttgttggta cccctacatc 5880
tggaacacat gggtatgagg aaatacettt acaaacattt gcttcttctg gtacggggga 5940
ggaacccatt agtagtaccc cattgcctac tgtgcggcgt gtagcaggtc cccgccttta 6000
cagtagggcc taccaacaag tgtcagtggc taaccctgag tttcttacac gtccatcctc 6060
tttaattaca tatgacaacc cggcctttga gcctgtggac actacattaa catttgatcc 6120
tcgtagtgat gttcctgatt cagattttat ggatattatc cgtctacata ggcctgcttt 6180
aacatccagg cgtgggactg ttcgctttag tagattaggt caacgggcaa ctatgtttac 6240
ccgcagcggt acacaaatag gtgctagggt tcacttttat catgatataa gtcctattgc 6300
accttcccca gaatatattg aactgcagcc tttagtatct gccacggagg acaatgactt 6360
gtttgatata tatgcagatg acatggaccc tgcagtgcct gtaccatcgc gttctactac 6420
ctcctttgca ttttttaaat attcgcccac tatatcttct gcctcttcct atagtaatgt 6480

-continued aacggtccct ttaacctcct cttgggatgt gcctgtatac acgggtcctg atattacatt 6540
accatctact acctctgtat ggcccattgt atcacccacg gcccctgcct ctacacagta 6600
tattggtata catggtacac attattattt gtggccatta tattatttta ttcctaagaa 6660
acgtaaacgt gttccctatt tttttgcaga tggctttgtg gcggcctagt gacaataccg 6720
tatatcttcc acctccttct gtggcaagag ttgtaaatac cgatgattat gtgactcgca 6780
caagcatatt ttatcatgct ggcagctcta gattattaac tgttggtaat ccatatttta 6840
gggttcctgc aggtggtggc aataagcagg atattcctaa ggtttctgca taccaatata 6900
gagtatttag ggtgcagtta cctgacccaa ataaatttgg tttacctgat actagtattt 6960
ataatcctga aacacaacgt ttagtgtggg cctgtgctgg agtggaaatt ggccgtggtc 7020
agcctttagg tgttggcctt agtgggcatc cattttataa taaattagat gacactgaaa 7080
gttcccatgc cgccacgtct aatgtttctg aggacgttag ggacaatgtg tctgtagatt 7140
ataagcagac acagttatgt attttgggct gtgcccctgc tattggggaa cactgggcta 7200
aaggcactgc ttgtaaatcg cgtcctttat cacagggcga ttgcccccct ttagaactta 7260
aaaacacagt tttggaagat ggtgatatgg tagatactgg atatggtgcc atggacttta 7320
gtacattgca agatactaaa tgtgaggtac cattggatat ttgtcagtct atttgtaaat 7380
atcctgatta tttacaaatg tctgcagatc cttatgggga ttccatgttt ttttgcttac 7440
ggcgtgagca gctttttgct aggcattttt ggaatagagc aggtactatg ggtgacactg 7500
tgcctcaatc cttatatatt aaaggcacag gtatgcgtgc ttcacctggc agctgtgtgt 7560
attctccctc tccaagtggc tctattgtta cctctgactc ccagttgttt aataaaccat 7620
attggttaca taaggcacag ggtcataaca atggtgtttg ctggcataat caattatttg 7680
ttactgtggt agataccact cgcagtacca atttaacaat atgtgcttct acacagtctc 7740
ctgtacctgg gcaatatgat gctaccaaat ttaagcagta tagcagacat gttgaggaat 7800
atgatttgca gtttattttt cagttgtgta ctattacttt aactgcagat gttatgtcct 7860
atattcatag tatgaatagc agtattttag aggattggaa ctttggtgtt cccccccccgc 7920 caactactag tttggtggat acatatcgtt ttgtacaatc tgttgctatt acctgtcaaa 7980
aggatgctgc accggctgaa aataaggatc cctatgataa gttaaagttt tggaatgtgg 8040
atttaaagga aaagttttct ttagacttag atcaatatcc ccttggacgt aaattttttgg 8100 ttcaggctgg attgcgtcgc aagcccacca taggccctcg caaacgttct gctccatctg 8160
ccactacgtc ttctaaacct gccaagcgtg tgcgtgtacg tgccaggaag taatatgtgt 8220
gtgtgtatat atatatacat ctattgttgt gtttgtatgt cctgtgtttg tgtttgttgt 8280
atgattgcat tgtatggtat gtatggttgt tgttgtatgt tgtatgttac tatatttgtt 8340
ggtatgtggc attaaataaa atatgttttg tggttctgtg tgttatgtgg ttgcgcccta 8400
gtgagtaaca actgtatttg tgtttgtggt atgggtgttg cttgttgggc tatatattgt 8460
cctgtatttc aagttataaa actgcacacc ttacagcatc cattttatcc tacaatcctc 8520
cattttgctg tgcaaccgat ttcggttgcc agatctgata tctctagagt cgacccatgg 8580
gggcccgccc caactggggt aacctttggg ctccccgggc gcgactagtg aattcagatc 8640
ttttggctta tgtctgtggt tttctgcaca atacagtacg ctggcactat tgcaaacttt 8700
aatcttttgg gcactgctcc tacatatttt gaacaattgg cgcgcctctt tggcgcatat 8760
aaggcgcacc tggtattagt cattttcctg tccaggtgcg ctacaacaat tgcttgcata 8820
actatatcca ctccctaagt aataaaactg cttttaggca catattttag tttgttttta 8880
cttaagctaa ttgcatactt ggcttgtaca actactttca tgtccaacat tctgtctacc 8940
cttaacatga actataatat gactaagctg tgcatacata gtttatgcaa ccgaaatagg 9000
ttgggcagca catactatac ttttc 9025

<210> SEQ ID NO 5
<211> LENGTH: 11404
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11404)
<223> OTHER INFORMATION: pMC_HPV18-RSV-dRFP

<400> SEQUENCE: 5
acattaccct gttatcccta gatgacatta ccctgttatc ccagatgaca ttaccctgtt 60
atccctagat gacattaccc tgttatccct agatgacatt taccctgtta tccctagatg 120
acattaccct gttatcccag atgacattac cctgttatcc ctagatacat taccctgtta 180
tcccagatga cataccctgt tatccctaga tgacattacc ctgttatccc agatgacatt 240
accctgttat ccctagatac attaccctgt tatcccagat gacataccct gttatcccta 300
gatgacatta ccctgttatc ccagatgaca ttaccctgtt atccctagat acattaccct 360
gttatcccag atgacatacc ctgttatccc tagatgacat taccctgtta tcccagatga 420
cattaccctg ttatccctag atacattacc ctgttatccc agatgacata ccctgttatc 480
cctagatgac attaccctgt tatcccagat gacattaccc tgttatccct agatacatta 540
ccctgttatc ccagatgaca taccctgtta tccctagatg acattaccct gttatcccag 600
atgacattac cctgttatcc ctagatacat taccctgtta tcccagatga cataccctgt 660
tatccctaga tgacattacc ctgttatccc agataaactc aatgatgatg atgatgatgg 720
tcgagactca gcggccgcgg tgccagggcg tgcccttggg ctccccgggc gcgactagtg 780
aattcagatc tgatagctta gatctcggct agcgtatacc ctcgacctgc aggtcgatcg 840
actctagtat ggtgcactct cagtacaatc tgctctgatg ccgcatagtt aagccagtat 900
ctgctccctg cttgtgtgtt ggaggtcgct gagtagtgcg cgagcaaaat ttaagctaca 960
acaaggcaag gcttgaccga caattgcatg aagaatctgc ttagggttag gcgttttgcg 1020
ctgcttcgcg atgtacgggc cagatatacg cgtatctgag gggactaggg tgtgtttagg 1080
cgaaaagcgg ggcttcggtt gtacgcggtt aggagtcccc tcaggatata gtagtttcgc 1140
ttttgcatag ggagggggaa atgtagtctt atgcaatact cttgtagtct tgcaacatgg 1200
taacgatgag ttagcaacat gccttacaag gagagaaaaa gcaccgtgca tgccgattgg 1260
tggaagtaag gtggtacgat cgtgccttat taggaaggca acagacgggt ctgacatgga 1320
ttggacgaac cactgaattc cgcattgcag agatattgta tttaagtgcc tagctcgata 1380
caataaacgc catttgacca ttcaccacat tggtgtgcac ctccaagctg gtagaggatc 1440
ggtcgatcga ctctagcgta tacggatcga tcctgcaggt cgactctaga caggtaagtg 1500
gcgtttctcg ggagccagc tgcgtccgct gtcgtgctgt cggtgtagta ctagcaagcg 1560
ttaagtcccc atctggctgc ggcctaccga agagtggtct tcacgtcaca cgctgtccca 1620
cgcacgtggt tggtttggtc gcttctggtt actgactact aagcagcctt ttcttttttc 1680
ctttcaggtt ctagacgcca ccatgagcga gctgatcaaa gaaaacatgc acatgaagct 1740

-continued gtacatggaa ggcaccgtga acaaccacca cttcaagtgc accagcgagg gcgagggcaa 1800
gccctacgag ggcacccaga ccatgaagat caaggtggtg gaaggcggcc cactgccctt 1860
cgccttcgac atcctggcca ccagctttat gtacggcagc aaggccttca tcaaccacac 1920
ccagggcatc cccgatttct tcaagcagag cttccccgag ggcttcacct gggagcggat 1980
caccacctac gaggacggcg gcgtgctgac cgccacccag gacaccagct tccagaacgg 2040
ctgcatcatc tacaacgtga agatcaacgg cgtgaacttc cccagcaacg gccccgtgat 2100
gcagaagaaa acccggggct gggaggccaa caccgagatg ctgtaccccg ccgatggcgg 2160
cctgagaggc cactctcaga tggccctgaa gctcgtgggc ggaggctacc tgcactgcag 2220
cttcaagacc acctacagaa gcaagaagcc cgccaagaac ctgaagatgc ccggcttcca 2280
cttcgtggac caccggctgg aacggatcaa agaggccgac aaagaaacct acgtcgagca 2340
gcacgagatg gccgtggcca agtactgcga cctgcctagc aagctgggcc acagagatga 2400
gagcggcctg cggagccgga tcagccacgg atttccacca gccgtggccg cccaggacga 2460
cggcacactg cctatgagct gcgcccagga atccggcatg gacagacacc ctgccgcctg 2520
tgccagcgcc aggatcaatg tctgagcggc cgcctcgagc tcgctgatca gcctcgactg 2580
tgccttctag ttgccagcca tctgttgttt gcccctcccc cgtgccttcc ttgaccctgg 2640
aaggtgccac tcccactgtc ctttcctaat aaaatgagga aattgcatcg cattgtctga 2700
gtaggtgtca ttctattctg gggggtgggg tggggcagga cagcaagggg gaggattggg 2760
aagacaatag caggcatgct taattaacct aaggcactac gtcttctaaa cctgccaagc 2820
gtgtgcgtgt acgtgccagg aagtaatatg tgtgtgtgta tatatatata catctattgt 2880
tgtgtttgta tgtcctgtgt ttgtgtttgt tgtatgattg cattgtatgg tatgtatggt 2940
tgttgttgta tgttgtatgt tactatattt gttggtatgt ggcattaaat aaaatatgtt 3000
ttgtggttct gtgtgttatg tggttgcgcc ctagtgagta acaactgtat ttgtgtttgt 3060
ggtatgggtg ttgcttgttg ggctatatat tgtcctgtat ttcaagttat aaaactgcac 3120
accttacagc atccatttta tcctacaatc ctccattttg ctgtgcaacc gatttcggtt 3180
gcctttggct tatgtctgtg gttttctgca caatacagta cgctggcact attgcaaact 3240
ttaatctttt gggcactgct cctacatatt ttgaacaatt ggcgcgcctc tttggcgcat 3300
ataaggcgca cctggtatta gtcattttcc tgtccaggtg cgctacaaca attgcttgca 3360
taactatatc cactccctaa gtaataaaac tgcttttagg cacatatttt agtttgtttt 3420
tacttaagct aattgcatac ttggcttgta caactacttt catgtccaac attctgtcta 3480
cccttaacat gaactataat atgactaagc tgtgcataca tagtttatgc aaccgaaata 3540
ggttgggcag cacatactat acttttcatt aatactttta acaattgtag tatataaaaa 3600
agggagtaac cgaaaacggt cgggaccgaa aacggtgtat ataaaagatg tgagaaacac 3660
accacaatac tatggcgcgc tttgaggatc caacacggcg accctacaag ctacctgatc 3720
tgtgcacgga actgaacact tcactgcaag acatagaaat aacctgtgta tattgcaaga 3780
cagtattgga acttacagag gtatttgaat ttgcatttaa agatttattt gtggtgtata 3840
gagacagtat accccatgct gcatgccata aatgtataga tttttattct agaattagag 3900
aattaagaca ttattcagac tctgtgtatg gagacacatt ggaaaaacta actaacactg 3960
ggttatacaa tttattaata aggtgcctgc ggtgccagaa accgttgaat ccagcagaaa 4020
aacttagaca ccttaatgaa aaacgacgat ttcacaacat agctgggcac tatagaggcc 4080
agtgccattc gtgctgcaac cgagcacgac aggaacgact ccaacgacgc agagaaacac 4140

```
aagtataata ttaagtatgc atggacctaa ggcaacattg caagacattg tattgcattt   4200
agagccccaa aatgaaattc cggttgacct tctatgtcac gagcaattaa gcgactcaga   4260
ggaagaaaac gatgaaatag atggagttaa tcatcaacat ttaccagccc gacgagccga   4320
accacaacgt cacacaatgt tgtgtatgtg ttgtaagtgt gaagccagaa ttgagctagt   4380
agtagaaagc tcagcagacg accttcgagc attccagcag ctgtttctga acaccctgtc   4440
ctttgtgtgt ccgtggtgtg catcccagca gtaagcaaca atggctgatc cagaaggtac   4500
agacggggag ggcacgggtt gtaacggctg gttttatgta caagctattg tagacaaaaa   4560
aacaggagat gtaatatcag atgacgagga cgaaaatgca acagacacag ggtcggatat   4620
ggtagatttt attgatacac aaggaacatt ttgtgaacag gcagagctag agacagcaca   4680
ggcattgttc catgcgcagg aggtccacaa tgatgcacaa gtgttgcatg ttttaaaacg   4740
aaagtttgca ggaggcagca cagaaaacag tccattaggg gagcggctgg aggtggatac   4800
agagttaagt ccacggttac aagaaatatc tttaaatagt gggcagaaaa aggcaaaaag   4860
gcggctgttt acaatatcag atagtggcta tggctgttct gaagtggaag caacacagat   4920
tcaggtaact acaaatggcg aacatggcgg caatgtatgt agtggcggca gtacggaggc   4980
tatagacaac gggggcacag agggcaacaa cagcagtgta gacggtacaa gtgacaatag   5040
caatatagaa aatgtaaatc cacaatgtac catagcacaa ttaaaagact tgttaaaagt   5100
aaacaataaa caaggagcta tgttagcagt atttaaagac acatatgggc tatcatttac   5160
agatttagtt agaaatttta aaagtgataa aaccacgtgt acagattggg ttacagctat   5220
atttggagta aacccaacaa tagcagaagg atttaaaaca ctaatacagc catttatatt   5280
atatgcccat attcaatgtc tagactgtaa atggggagta ttaatattag ccctgttgcg   5340
ttacaaatgt ggtaagagta gactaacagt tgctaaaggt ttaagtacgt tgttacacgt   5400
acctgaaact tgtatgttaa ttcaaccacc aaaattgcga agtagtgttg cagcactata   5460
ttggtataga acaggaatat caaatattag tgaagtaatg ggagacacac ctgagtggat   5520
acaaagactt actattatac aacatggaat agatgatagc aattttgatt tgtcagaaat   5580
ggtacaatgg gcatttgata atgagctgac agatgaaagc gatatggcat ttgaatatgc   5640
cttattagca gacagcaaca gcaatgcagc tgccttttta aaaagcaatt gccaagctaa   5700
atatttaaaa gattgtgcca caatgtgcaa acattatagg cgagcccaaa aacgacaaat   5760
gaatatgtca cagtggatac gatttagatg ttcaaaaata gatgaagggg gagattggag   5820
accaatagtg caattcctgc gataccaaca aatagagttt ataacatttt taggagcctt   5880
aaaatcattt ttaaaaggaa cccccaaaaa aaattgttta gtattttgtg gaccagcaaa   5940
tacaggaaaa tcatattttg gaatgagttt tatacacttt atacaaggag cagtaatatc   6000
atttgtgaat tccactagtc atttttggtt ggaaccgtta acagatacta aggtggccat   6060
gttagatgat gcaacgacca cgtgttggac atactttgat acctatatga gaaatgcgtt   6120
agatggcaat ccaataagta ttgatagaaa gcacaaacca ttaatacaac taaaatgtcc   6180
tccaatacta ctaaccacaa atatacatcc agcaaaggat aatagatggc catatttaga   6240
aagtagaata acagtatttg aatttccaaa tgcatttcca tttgataaaa atggcaatcc   6300
agtatatgaa ataaatgaca aaaattggaa atgttttttt gaaaggacat ggtccagatt   6360
agatttgcac gaggaagagg aagatgcaga caccgaagga aaccctttcg gaacgtttaa   6420
gttgcgtgca ggacaaaatc atagaccact atgaaaatga cagtaaagac atagacagcc   6480
```

-continued

```
aaatacagta ttggcaacta atacgttggg aaaatgcaat attctttgca gcaagggaac   6540
atggcataca gacattaaac caccaggtgg tgccagccta taacatttca aaaagtaaag   6600
cacataaagc tattgaactg caaatggccc tacaaggcct tgcacaaagt cgatacaaaa   6660
ccgaggattg gacactgcaa gacacatgcg aggaactatg gaatacagaa cctactcact   6720
gctttaaaaa aggtggccaa acagtacaag tatattttga tggcaacaaa gacaattgta   6780
tgacctatgt agcatgggac agtgtgtatt atatgactga tgcaggaaca tgggacaaaa   6840
ccgctacctg tgtaagtcac aggggattgt attatgtaaa ggaagggtac aacacgtttt   6900
atatagaatt taaaagtgaa tgtgaaaaat atgggaacac aggtacgtgg gaagtacatt   6960
ttgggaataa tgtaattgat tgtaatgact ctatgtgcag taccagtgac gacacggtat   7020
ccgctactca gcttgttaaa cagctacagc acaccccctc accgtattcc agcaccgtgt   7080
ccgtgggcac cgcaaagacc tacggccaga cgtcggctgc tacacgacct ggacactgtg   7140
gactcgcgga gaagcagcat tgtggacctg tcaacccact tctcggtgca gctacaccta   7200
caggcaacaa caaaagacgg aaactctgta gtggtaacac tacgcctata atacatttaa   7260
aaggtgacag aaacagttta aaatgtttac ggtacagatt gcgaaaacat agcgaccact   7320
atagagatat atcatccacc tggcattgga caggtgcagg caatgaaaaa acaggaatac   7380
tgactgtaac ataccatagt gaaacacaaa gaacaaaatt tttaaatact gttgcaattc   7440
cagatagtgt acaaatattg gtgggataca tgacaatgta atacatatgc tgtagtacca   7500
atatgttatc acttattttt ttattttgct tttgtgtatg catgtatgtg tgctgccatg   7560
tcccgctttt gccatctgtc tgtatgtgtg cgtatgcatg ggtattggta tttgtgtata   7620
ttgtggtaat aacgtcccct gccacagcat tcacagtata tgtattttgt tttttattgc   7680
ccatgttact attgcatata catgctatat tgtctttaca gtaattgtat aggttgtttt   7740
atacagtgta ttgtacattg tatattttgt tttatacctt ttatgctttt tgtatttttg   7800
taataaaagt atggtatccc accgtgccgc acgacgcaaa cgggcttcgg taactgactt   7860
atataaaaca tgtaaacaat ctggtacatg tccacctgat gttgttccta aggtggaggg   7920
caccacgtta gcagataaaa tattgcaatg gtcaagcctt ggtatatttt tgggtggact   7980
tggcataggt actggcagtg gtacaggggg tcgtacaggg tacattccat tgggtgggcg   8040
ttccaataca gtggtggatg ttggtcctac acgtccccca gtggttattg aacctgtggg   8100
cccggatcca agctatctct agagtcgacc catgggggcc cgccccaact ggggtaacct   8160
ttgagttctc tcagttgggg gtaatcagca tcatgatgtg gtaccacatc atgatgctga   8220
ttataagaat gcggccgcca cactctagtg gatctcgagt taataattca gaagaactcg   8280
tcaagaaggc gatagaaggc gatgcgctgc gaatcgggag cggcgatacc gtaaagcacg   8340
aggaagcggt cagcccattc gccgccaagc tcttcagcaa tatcacgggt agccaacgct   8400
atgtcctgat agcggtccgc cacacccagc cggccacagt cgatgaatcc agaaaagcgg   8460
ccattttcca ccatgatatt cggcaagcag gcatcgccat gggtcacgac gagatcctcg   8520
ccgtcgggca tgctcgcctt gagcctggcg aacagttcgg ctggcgcgag cccctgatgc   8580
tcttcgtcca gatcatcctg atcgacaaga ccggcttcca tccgagtacg tgctcgctcg   8640
atgcgatgtt tcgcttggtg gtcgaatggg caggtagccg gatcaagcgt atgcagccgc   8700
cgcattgcat cagccatgat ggatactttc tcggcaggag caaggtgtag atgacatgga   8760
gatcctgccc cggcacttcg cccaatagca gccagtccct tcccgcttca gtgacaacgt   8820
cgagcacagc tgcgcaagga acgcccgtcg tggccagcca cgatagccgc gctgcctcgt   8880
```

```
cttgcagttc attcagggca ccggacaggt cggtcttgac aaaaagaacc gggcgcccct   8940
gcgctgacag ccggaacacg gcggcatcag agcagccgat tgtctgttgt gcccagtcat   9000
agccgaatag cctctccacc caagcggccg gagaacctgc gtgcaatcca tcttgttcaa   9060
tcatgcgaaa cgatcctcat cctgtctctt gatcagagct tgatcccctg cgccatcaga   9120
tccttggcgg cgagaaagcc atccagttta ctttgcaggg cttcccaacc ttaccagagg   9180
gcgccccagc tggcaattcc ggttcgcttg ctgtccataa aaccgcccag tctagctatc   9240
gccatgtaag cccactgcaa gctacctgct ttctctttgc gcttgcgttt tcccttgtcc   9300
agatagccca gtagctgaca ttcatccggg gtcagcaccg tttctgcgga ctggctttct   9360
acgtgctcga ggggggccaa acggtctcca gcttggctgt tttggcggat gagagaagat   9420
tttcagcctg atacagatta aatcagaacg cagaagcggt ctgataaaac agaatttgcc   9480
tggcggcagt agcgcggtgg tcccacctga ccccatgccg aactcagaag tgaaacgccg   9540
tagcgccgat ggtagtgtgg ggtctcccca tgcgagagta gggaactgcc aggcatcaaa   9600
taaaacgaaa ggctcagtcg aaagactggg cctttcgttt tatctgttgt ttgtcggtga   9660
acgctctcct gagtaggaca aatccgccgg gagcggattt gaacgttgcg aagcaacggc   9720
ccggagggtg gcgggcagga cgcccgccat aaactgccag gcatcaaatt aagcagaagg   9780
ccatcctgac ggatggcctt tttgcgtttc tacaaactct tttgtttatt tttctaaata   9840
cattcaaata tgtatccgct catgaccaaa atcccttaac gtgagttttc gttccactga   9900
gcgtcagacc ccgtagaaaa gatcaaagga tcttcttgag atcctttttt tctgcgcgta   9960
atctgctgct tgcaaacaaa aaaaccaccg ctaccagcgg tggtttgttt gccggatcaa  10020
gagctaccaa ctctttttcc gaaggtaact ggcttcagca gagcgcagat accaaatact  10080
gtccttctag tgtagccgta gttaggccac cacttcaaga actctgtagc accgcctaca  10140
tacctcgctc tgctaatcct gttaccagtg gctgctgcca gtggcgataa gtcgtgtctt  10200
accgggttgg actcaagacg atagttaccg gataaggcgc agcggtcggg ctgaacgggg  10260
ggttcgtgca cacagcccag cttggagcga acgacctaca ccgaactgag atacctacag  10320
cgtgagctat gagaaagcgc cacgcttccc gaagggagaa aggcggacag gtatccggta  10380
agcggcaggg tcggaacagg agagcgcacg agggagcttc caggggggaaa cgcctggtat  10440
ctttatagtc ctgtcgggtt tcgccacctc tgacttgagc gtcgattttt gtgatgctcg  10500
tcaggggggc ggagcctatg gaaaaacgcc agcaacgcgg cctttttacg gttcctggcc  10560
ttttgctggc cttttgctca catgttcttt cctgcgttat cccctgattc tgtggataac  10620
cgtattaccg cctttgagtg agctgatacc gctcgccgca gccgaacgac cgagcgcagc  10680
gagtcagtga gcgaggaagc ggaagagcgc ctgatgcggt attttctcct tacgcatctg  10740
tgcggtattt cacaccgcat atggtgcact ctcagtacaa tctgctctga tgccgcatag  10800
ttaagccagt atacactccg ctatcgctac gtgactgggt catggctgcg ccccgacacc  10860
cgccaacacc cgctgacgcg ccctgacggg cttgtctgct cccggcatcc gcttacagac  10920
aagctgtgac cgtctccggg agctgcatgt gtcagaggtt ttcaccgtca tcaccgaaac  10980
gcgcgaggca gcagatcaat tcgcgcgcga aggcgaagcg gcatgcataa tgtgcctgtc  11040
aaatggacga agcagggatt ctgcaaaccc tatgctactc cgtcaagccg tcaattgtct  11100
gattcgttac caattatgac aacttgacgg ctacatcatt cactttttct tcacaaccgg  11160
cacggaactc gctcgggctg gccccggtgc atttttttaaa tacccgcgag aaatagagtt  11220
```

-continued gatcgtcaaa accaacattg cgaccgacgg tggcgatagg catccgggtg gtgctcaaaa 11280
gcagcttcgc ctggctgata cgttggtcct cgcgccagct taagacgcta atccctaact 11340
gctggcggaa aagatgtgac agacgcgacg gcgacaagca aacatgctgt gcgacgctgg 11400
cgat 11404

<210> SEQ ID NO 6
<211> LENGTH: 11275
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11275)
<223> OTHER INFORMATION: pMC_HPV18-RSV-RFP

<400> SEQUENCE: 6
acattaccct gttatcccta gatgacatta ccctgttatc ccagatgaca ttaccctgtt 60
atccctagat gacattaccc tgttatccct agatgacatt taccctgtta tccctagatg 120
acattaccct gttatcccag atgacattac cctgttatcc ctagatacat taccctgtta 180
tcccagatga cataccctgt tatccctaga tgacattacc ctgttatccc agatgacatt 240
accctgttat ccctagatac attaccctgt tatcccagat gacataccct gttatcccta 300
gatgacatta ccctgttatc ccagatgaca ttaccctgtt atccctagat acattaccct 360
gttatcccag atgacatacc ctgttatccc tagatgacat taccctgtta tcccagatga 420
cattaccctg ttatccctag atacattacc ctgttatccc agatgacata ccctgttatc 480
cctagatgac attaccctgt tatcccagat gacattaccc tgttatccct agatacatta 540
ccctgttatc ccagatgaca taccctgtta tccctagatg acattaccct gttatcccag 600
atgacattac cctgttatcc ctagatacat taccctgtta tcccagatga cataccctgt 660
tatccctaga tgacattacc ctgttatccc agataaactc aatgatgatg atgatgatgg 720
tcgagactca gcggccgcgg tgccagggcg tgcccttggg ctccccgggc gcgactagtg 780
aattcagatc tgatagctta gatctcggct agcgtatacc ctcgacctgc aggtcgatcg 840
actctagtat ggtgcactct cagtacaatc tgctctgatg ccgcatagtt aagccagtat 900
ctgctccctg cttgtgtgtt ggaggtcgct gagtagtgcg cgagcaaaat ttaagctaca 960
acaaggcaag gcttgaccga caattgcatg aagaatctgc ttagggttag gcgttttgcg 1020
ctgcttcgcg atgtacgggc cagatatacg cgtatctgag gggactaggg tgtgtttagg 1080
cgaaaagcgg ggcttcggtt gtacgcggtt aggagtcccc tcaggatata gtagtttcgc 1140
ttttgcatag ggagggggaa atgtagtctt atgcaatact cttgtagtct tgcaacatgg 1200
taacgatgag ttagcaacat gccttacaag gagagaaaaa gcaccgtgca tgccgattgg 1260
tggaagtaag gtggtacgat cgtgccttat taggaaggca acagacgggt ctgacatgga 1320
ttggacgaac cactgaattc cgcattgcag agatattgta tttaagtgcc tagctcgata 1380
caataaacgc catttgacca ttcaccacat tggtgtgcac ctccaagctg gtagaggatc 1440
ggtcgatcga ctctagcgta tacggatcga tcctgcaggt cgactctaga caggtaagtg 1500
gcgtttctcg gggagccagc tgcgtccgct gtcgtgctgt cggtgtagta ctagcaagcg 1560
ttaagtcccc atctggctgc ggcctaccga agagtggtct tcacgtcaca cgctgtccca 1620
cgcacgtggt tggtttggtc gcttctggtt actgactact aagcagcctt ttcttttttc 1680
ctttcaggtt ctagacgcca ccatggtgtc taagggcgaa gagctgatta aggagaacat 1740

-continued

```
gcacatgaag ctgtacatgg agggcaccgt gaacaaccac cacttcaagt gcacatccga   1800
gggcgaaggc aagccctacg agggcaccca gaccatgaga atcaaggtgg tcgagggcgg   1860
ccctctcccc ttcgccttcg acatcctggc taccagcttc atgtacggca gcagaacctt   1920
catcaaccac acccagggca tccccgactt ctttaagcag tccttccctg agggcttcac   1980
atgggagaga gtcaccacat acgaagacgg gggcgtgctg accgctaccc aggacaccag   2040
cctccaggac ggctgcctca tctacaacgt caagatcaga ggggtgaact tcccatccaa   2100
cggccctgtg atgcagaaga aaacactcgg ctgggaggcc aacaccgaga tgctgtaccc   2160
cgctgacggc ggcctggaag gcagaagcga catggccctg aagctcgtgg gcgggggcca   2220
cctgatctgc aacttcaaga ccacatacag atccaagaaa cccgctaaga acctcaagat   2280
gcccggcgtc tactatgtgg accacagact ggaaagaatc aaggaggccg acaaagagac   2340
ctacgtcgag cagcacgagg tggctgtggc cagatactgc gacctcccta gcaaactggg   2400
gcacaaactt aattgagcgg ccgcctcgag ctcgctgatc agcctcgact gtgccttcta   2460
gttgccagcc atctgttgtt tgcccctccc ccgtgccttc cttgaccctg gaaggtgcca   2520
ctcccactgt cctttcctaa taaaatgagg aaattgcatc gcattgtctg agtaggtgtc   2580
attctattct ggggggtggg gtggggcagg acagcaaggg ggaggattgg gaagacaata   2640
gcaggcatgc ttaattaacc taaggcacta cgtcttctaa acctgccaag cgtgtgcgtg   2700
tacgtgccag gaagtaatat gtgtgtgtgt atatatatat acatctattg ttgtgtttgt   2760
atgtcctgtg tttgtgtttg ttgtatgatt gcattgtatg gtatgtatgg ttgttgttgt   2820
atgttgtatg ttactatatt tgttggtatg tggcattaaa taaaatatgt tttgtggttc   2880
tgtgtgttat gtggttgcgc cctagtgagt aacaactgta tttgtgtttg tggtatgggt   2940
gttgcttgtt gggctatata ttgtcctgta tttcaagtta taaaactgca caccttacag   3000
catccatttt atcctacaat cctccatttt gctgtgcaac cgatttcggt tgcctttggc   3060
ttatgtctgt ggttttctgc acaatacagt acgctggcac tattgcaaac tttaatcttt   3120
tgggcactgc tcctacatat tttgaacaat tggcgcgcct ctttggcgca tataaggcgc   3180
acctggtatt agtcattttc ctgtccaggt gcgctacaac aattgcttgc ataactatat   3240
ccactcccta agtaataaaa ctgcttttag gcacatattt tagtttgttt ttacttaagc   3300
taattgcata cttggcttgt acaactactt tcatgtccaa cattctgtct acccttaaca   3360
tgaactataa tatgactaag ctgtgcatac atagtttatg caaccgaaat aggttgggca   3420
gcacatacta tacttttcat taatactttt aacaattgta gtatataaaa aagggagtaa   3480
ccgaaaacgg tcgggaccga aaacggtgta tataaaagat gtgagaaaca caccacaata   3540
ctatggcgcg ctttgaggat ccaacacggc gaccctacaa gctacctgat ctgtgcacgg   3600
aactgaacac ttcactgcaa gacatagaaa taacctgtgt atattgcaag acagtattgg   3660
aacttacaga ggtatttgaa tttgcattta aagatttatt tgtggtgtat agagacagta   3720
taccccatgc tgcatgccat aaatgtatag atttttattc tagaattaga gaattaagac   3780
attattcaga ctctgtgtat ggagacacat tggaaaaact aactaacact gggttataca   3840
atttattaat aaggtgcctg cggtgccaga aaccgttgaa tccagcagaa aaacttagac   3900
accttaatga aaaacgacga tttcacaaca tagctgggca ctatagaggc cagtgccatt   3960
cgtgctgcaa ccgagcacga caggaacgac tccaacgacg cagagaaaca caagtataat   4020
attaagtatg catggaccta aggcaacatt gcaagacatt gtattgcatt tagagcccca   4080
```

-continued

```
aaatgaaatt ccggttgacc ttctatgtca cgagcaatta agcgactcag aggaagaaaa   4140
cgatgaaata gatggagtta atcatcaaca tttaccagcc cgacgagccg aaccacaacg   4200
tcacacaatg ttgtgtatgt gttgtaagtg tgaagccaga attgagctag tagtagaaag   4260
ctcagcagac gaccttcgag cattccagca gctgtttctg aacaccctgt cctttgtgtg   4320
tccgtggtgt gcatcccagc agtaagcaac aatggctgat ccagaaggta cagacgggga   4380
gggcacgggt tgtaacggct ggttttatgt acaagctatt gtagacaaaa aaacaggaga   4440
tgtaatatca gatgacgagg acgaaaatgc aacagacaca gggtcggata tggtagattt   4500
tattgataca caaggaacat tttgtgaaca ggcagagcta gagacagcac aggcattgtt   4560
ccatgcgcag gaggtccaca atgatgcaca agtgttgcat gttttaaaac gaaagtttgc   4620
aggaggcagc acagaaaaca gtccattagg ggagcggctg gaggtggata cagagttaag   4680
tccacggtta caagaaatat ctttaaatag tgggcagaaa aaggcaaaaa ggcggctgtt   4740
tacaatatca gatagtggct atggctgttc tgaagtggaa gcaacacaga ttcaggtaac   4800
tacaaatggc gaacatggcg gcaatgtatg tagtggcggc agtacggagg ctatagacaa   4860
cgggggcaca gagggcaaca acagcagtgt agacggtaca agtgacaata gcaatataga   4920
aaatgtaaat ccacaatgta ccatagcaca attaaaagac ttgttaaaag taaacaataa   4980
acaaggagct atgttagcag tatttaaaga cacatatggg ctatcattta cagatttagt   5040
tagaaatttt aaaagtgata aaaccacgtg tacagattgg gttacagcta tatttggagt   5100
aaacccaaca atagcagaag gatttaaaac actaatacag ccatttatat tatatgccca   5160
tattcaatgt ctagactgta aatggggagt attaatatta gccctgttgc gttacaaatg   5220
tggtaagagt agactaacag ttgctaaagg tttaagtacg ttgttacacg tacctgaaac   5280
ttgtatgtta attcaaccac caaaattgcg aagtagtgtt gcagcactat attggtatag   5340
aacaggaata tcaaatatta gtgaagtaat gggagacaca cctgagtgga tacaaagact   5400
tactattata caacatggaa tagatgatag caattttgat ttgtcagaaa tggtacaatg   5460
ggcatttgat aatgagctga cagatgaaag cgatatggca tttgaatatg ccttattagc   5520
agacagcaac agcaatgcag ctgccttttt aaaaagcaat tgccaagcta aatatttaaa   5580
agattgtgcc acaatgtgca aacattatag gcgagcccaa aaacgacaaa tgaatatgtc   5640
acagtggata cgatttagat gttcaaaaat agatgaaggg ggagattgga gaccaatagt   5700
gcaattcctg cgataccaac aaatagagtt tataacattt ttaggagcct taaaatcatt   5760
tttaaaagga acccccaaaa aaaattgttt agtattttgt ggaccagcaa atacaggaaa   5820
atcatatttt ggaatgagtt ttatacactt tatacaagga gcagtaatat catttgtgaa   5880
ttccactagt catttttggt tggaaccgtt aacagatact aaggtggcca tgttagatga   5940
tgcaacgacc acgtgttgga catactttga tacctatatg agaaatgcgt tagatggcaa   6000
tccaataagt attgatagaa agcacaaacc attaatacaa ctaaaatgtc ctccaatact   6060
actaaccaca aatatacatc cagcaaagga taatagatgg ccatatttag aaagtagaat   6120
aacagtattt gaatttccaa atgcatttcc atttgataaa aatggcaatc cagtatatga   6180
aataaatgac aaaaattgga aatgtttttt tgaaaggaca tggtccagat tagatttgca   6240
cgaggaagag gaagatgcag acaccgaagg aaacccctttc ggaacgttta agttgcgtgc   6300
aggacaaaat catagaccac tatgaaaatg acagtaaaga catagacagc caaatacagt   6360
attggcaact aatacgttgg gaaaatgcaa tattctttgc agcaagggaa catggcatac   6420
agacattaaa ccaccaggtg gtgccagcct ataacatttc aaaaagtaaa gcacataaag   6480
```

```
ctattgaact gcaaatggcc ctacaaggcc ttgcacaaag tcgatacaaa accgaggatt   6540
ggacactgca agacacatgc gaggaactat ggaatacaga acctactcac tgctttaaaa   6600
aaggtggcca aacagtacaa gtatattttg atggcaacaa agacaattgt atgacctatg   6660
tagcatggga cagtgtgtat tatatgactg atgcaggaac atgggacaaa accgctacct   6720
gtgtaagtca caggggattg tattatgtaa aggaagggta caacacgttt tatatagaat   6780
ttaaaagtga atgtgaaaaa tatgggaaca caggtacgtg ggaagtacat tttgggaata   6840
atgtaattga ttgtaatgac tctatgtgca gtaccagtga cgacacggta tccgctactc   6900
agcttgttaa acagctacag cacacccccct caccgtattc cagcaccgtg tccgtgggca   6960
ccgcaaagac ctacggccag acgtcggctg ctacacgacc tggacactgt ggactcgcgg   7020
agaagcagca ttgtggacct gtcaacccac ttctcggtgc agctacacct acaggcaaca   7080
acaaaagacg gaaactctgt agtggtaaca ctacgcctat aatacattta aaaggtgaca   7140
gaaacagttt aaaatgttta cggtacagat tgcgaaaaca tagcgaccac tatagagata   7200
tatcatccac ctggcattgg acaggtgcag gcaatgaaaa aacaggaata ctgactgtaa   7260
cataccatag tgaaacacaa agaacaaaat ttttaaatac tgttgcaatt ccagatagtg   7320
tacaaatatt ggtgggatac atgacaatgt aatacatatg ctgtagtacc aatatgttat   7380
cacttatttt tttattttgc ttttgtgtat gcatgtatgt gtgctgccat gtcccgcttt   7440
tgccatctgt ctgtatgtgt gcgtatgcat gggtattggt atttgtgtat attgtggtaa   7500
taacgtcccc tgccacagca ttcacagtat atgtattttg ttttttattg cccatgttac   7560
tattgcatat acatgctata ttgtctttac agtaattgta taggttgttt tatacagtgt   7620
attgtacatt gtatattttg ttttatacct tttatgcttt ttgtattttt gtaataaaag   7680
tatggtatcc caccgtgccg cacgacgcaa acgggcttcg gtaactgact tatataaaac   7740
atgtaaacaa tctggtacat gtccacctga tgttgttcct aaggtggagg gcaccacgtt   7800
agcagataaa atattgcaat ggtcaagcct tggtatattt ttgggtggac ttggcatagg   7860
tactggcagt ggtacagggg gtcgtacagg gtacattcca ttgggtgggc gttccaatac   7920
agtggtggat gttggtccta cacgtccccc agtggttatt gaacctgtgg gcccggatcc   7980
aagctatctc tagagtcgac ccatgggggc ccgccccaac tggggtaacc tttgagttct   8040
ctcagttggg ggtaatcagc atcatgatgt ggtaccacat catgatgctg attataagaa   8100
tgcggccgcc acactctagt ggatctcgag ttaataattc agaagaactc gtcaagaagg   8160
cgatagaagg cgatgcgctg cgaatcggga gcggcgatac cgtaaagcac gaggaagcgg   8220
tcagcccatt cgccgccaag ctcttcagca atatcacggg tagccaacgc tatgtcctga   8280
tagcggtccg ccacacccag ccggccacag tcgatgaatc cagaaaagcg gccattttcc   8340
accatgatat tcggcaagca ggcatcgcca tgggtcacga cgagatcctc gccgtcgggc   8400
atgctcgcct tgagcctggc gaacagttcg gctggcgcga gcccctgatg ctcttcgtcc   8460
agatcatcct gatcgacaag accggcttcc atccgagtac gtgctcgctc gatgcgatgt   8520
ttcgcttggt ggtcgaatgg gcaggtagcc ggatcaagcg tatgcagccg ccgcattgca   8580
tcagccatga tggatacttt ctcggcagga gcaaggtgta gatgacatgg agatcctgcc   8640
ccggcacttc gcccaatagc agccagtccc ttcccgcttc agtgacaacg tcgagcacag   8700
ctgcgcaagg aacgcccgtc gtggccagcc acgatagccg cgctgcctcg tcttgcagtt   8760
cattcagggc accggacagg tcggtcttga caaaaagaac cgggcgcccc tgcgctgaca   8820
```

-continued

```
gccggaacac ggcggcatca gagcagccga ttgtctgttg tgcccagtca tagccgaata   8880
gcctctccac ccaagcggcc ggagaacctg cgtgcaatcc atcttgttca atcatgcgaa   8940
acgatcctca tcctgtctct tgatcagagc ttgatcccct gcgccatcag atccttggcg   9000
gcgagaaagc catccagttt actttgcagg gcttcccaac cttaccagag ggcgccccag   9060
ctggcaattc cggttcgctt gctgtccata aaaccgccca gtctagctat cgccatgtaa   9120
gcccactgca agctacctgc tttctctttg cgcttgcgtt ttcccttgtc cagatagccc   9180
agtagctgac attcatccgg ggtcagcacc gtttctgcgg actggctttc tacgtgctcg   9240
agggggccca aacggtctcc agcttggctg ttttggcgga tgagagaaga ttttcagcct   9300
gatacagatt aaatcagaac gcagaagcgg tctgataaaa cagaatttgc ctggcggcag   9360
tagcgcggtg gtcccacctg accccatgcc gaactcagaa gtgaaacgcc gtagcgccga   9420
tggtagtgtg gggtctcccc atgcgagagt agggaactgc caggcatcaa ataaaacgaa   9480
aggctcagtc gaaagactgg gcctttcgtt ttatctgttg tttgtcggtg aacgctctcc   9540
tgagtaggac aaatccgccg ggagcggatt tgaacgttgc gaagcaacgg cccggagggt   9600
ggcgggcagg acgcccgcca taaactgcca ggcatcaaat taagcagaag gccatcctga   9660
cggatggcct ttttgcgttt ctacaaactc ttttgtttat ttttctaaat acattcaaat   9720
atgtatccgc tcatgaccaa aatcccttaa cgtgagtttt cgttccactg agcgtcagac   9780
cccgtagaaa agatcaaagg atcttcttga gatccttttt ttctgcgcgt aatctgctgc   9840
ttgcaaacaa aaaaaccacc gctaccagcg gtggtttgtt tgccggatca agagctacca   9900
actctttttc cgaaggtaac tggcttcagc agagcgcaga taccaaatac tgtccttcta   9960
gtgtagccgt agttaggcca ccacttcaag aactctgtag caccgcctac atacctcgct  10020
ctgctaatcc tgttaccagt ggctgctgcc agtggcgata agtcgtgtct taccgggttg  10080
gactcaagac gatagttacc ggataaggcg cagcggtcgg gctgaacggg gggttcgtgc  10140
acacagccca gcttggagcg aacgacctac accgaactga gatacctaca gcgtgagcta  10200
tgagaaagcg ccacgcttcc cgaagggaga aaggcggaca ggtatccggt aagcggcagg  10260
gtcggaacag gagagcgcac gagggagctt ccagggggaa acgcctggta tctttatagt  10320
cctgtcgggt ttcgccacct ctgacttgag cgtcgatttt tgtgatgctc gtcagggggg  10380
cggagcctat ggaaaaacgc cagcaacgcg gcctttttac ggttcctggc cttttgctgg  10440
ccttttgctc acatgttctt tcctgcgtta tcccctgatt ctgtggataa ccgtattacc  10500
gcctttgagt gagctgatac cgctcgccgc agccgaacga ccgagcgcag cgagtcagtg  10560
agcgaggaag cggaagagcg cctgatgcgg tattttctcc ttacgcatct gtgcggtatt  10620
tcacaccgca tatggtgcac tctcagtaca atctgctctg atgccgcata gttaagccag  10680
tatacactcc gctatcgcta cgtgactggg tcatggctgc gccccgacac ccgccaacac  10740
ccgctgacgc gccctgacgg gcttgtctgc tcccggcatc cgcttacaga caagctgtga  10800
ccgtctccgg gagctgcatg tgtcagaggt tttcaccgtc atcaccgaaa cgcgcgaggc  10860
agcagatcaa ttcgcgcgcg aaggcgaagc ggcatgcata atgtgcctgt caaatggacg  10920
aagcagggat tctgcaaacc ctatgctact ccgtcaagcc gtcaattgtc tgattcgtta  10980
ccaattatga caacttgacg gctacatcat tcactttttc ttcacaaccg gcacggaact  11040
cgctcgggct ggccccggtg cattttttaa atacccgcga gaaatagagt tgatcgtcaa  11100
aaccaacatt gcgaccgacg gtggcgatag gcatccgggt ggtgctcaaa agcagcttcg  11160
cctggctgat acgttggtcc tcgcgccagc ttaagacgct aatccctaac tgctggcgga  11220
```

aaagatgtga cagacgcgac ggcgacaagc aaacatgctg tgcgacgctg gcgat 11275

<210> SEQ ID NO 7
<211> LENGTH: 11506
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11506)

<400> SEQUENCE: 7
acattaccct gttatcccta gatgacatta ccctgttatc ccagatgaca ttaccctgtt 60
atccctagat gacattaccc tgttatccct agatgacatt taccctgtta tccctagatg 120
acattaccct gttatcccag atgacattac cctgttatcc ctagatacat taccctgtta 180
tcccagatga cataccctgt tatccctaga tgacattacc ctgttatccc agatgacatt 240
accctgttat ccctagatac attaccctgt tatcccagat gacataccct gttatcccta 300
gatgacatta ccctgttatc ccagatgaca ttaccctgtt atccctagat acattaccct 360
gttatcccag atgacatacc ctgttatccc tagatgacat taccctgtta tcccagatga 420
cattaccctg ttatccctag atacattacc ctgttatccc agatgacata ccctgttatc 480
cctagatgac attaccctgt tatcccagat gacattaccc tgttatccct agatacatta 540
ccctgttatc ccagatgaca taccctgtta tccctagatg acattaccct gttatcccag 600
atgacattac cctgttatcc ctagatacat taccctgtta tcccagatga cataccctgt 660
tatccctaga tgacattacc ctgttatccc agataaactc aatgatgatg atgatgatgg 720
tcgagactca gcggccgcgg tgccagggcg tgcccttggg ctccccgggc gcgactagtg 780
aattcagatc tgatagctta gatctcggct agcgtatacc ctcgacctgc aggtcgatcg 840
actctagtat ggtgcactct cagtacaatc tgctctgatg ccgcatagtt aagccagtat 900
ctgctccctg cttgtgtgtt ggaggtcgct gagtagtgcg cgagcaaaat ttaagctaca 960
acaaggcaag gcttgaccga caattgcatg aagaatctgc ttagggttag gcgttttgcg 1020
ctgcttcgcg atgtacgggc cagatatacg cgtatctgag gggactaggg tgtgtttagg 1080
cgaaaagcgg ggcttcggtt gtacgcggtt aggagtcccc tcaggatata gtagtttcgc 1140
ttttgcatag ggagggggaa atgtagtctt atgcaatact cttgtagtct tgcaacatgg 1200
taacgatgag ttagcaacat gccttacaag gagagaaaaa gcaccgtgca tgccgattgg 1260
tggaagtaag gtggtacgat cgtgccttat taggaaggca acagacgggt ctgacatgga 1320
ttggacgaac cactgaattc cgcattgcag agatattgta tttaagtgcc tagctcgata 1380
caataaacgc catttgacca ttcaccacat tggtgtgcac ctccaagctg gtagaggatc 1440
ggtcgatcga ctctagcgta tacggatcga tcctgcaggt cgactctaga caggtaagtg 1500
gcgtttctcg gggagccagc tgcgtccgct gtcgtgctgt cggtgtagta ctagcaagcg 1560
ttaagtcccc atctggctgc ggcctaccga agagtggtct tcacgtcaca cgctgtccca 1620
cgcacgtggt tggtttggtc gcttctggtt actgactact aagcagcctt ttcttttttc 1680
ctttcaggtt ctagacgcca ccatggccac ttcgaaagtt tatgatccag aacaaaggaa 1740
acggatgata actggtccgc agtggtgggc cagatgtaaa caaatgaatg ttcttgattc 1800
atttattaat tattatgatt cagaaaaaca tgcagaaaat gctgttattt ttttacatgg 1860
taacgcggcc tcttcttatt tatggcgaca tgttgtgcca catattgagc cagtagcgcg 1920

-continued

```
gtgtattata ccagacctta ttggtatggg caaatcaggc aaatctggta atggttctta   1980
taggttactt gatcattaca aatatcttac tgcatggttt gaacttctta atttaccaaa   2040
gaagatcatt tttgtcggcc atgattgggg tgcttgtttg gcatttcatt atagctatga   2100
gcatcaagat aagatcaaag caatagttca cgctgaaagt gtagtagatg tgattgaatc   2160
atgggatgaa tggcctgata ttgaagaaga tattgcgttg atcaaatctg aagaaggaga   2220
aaaaatggtt ttggagaata acttcttcgt ggaaaccatg ttgccatcaa aaatcatgag   2280
aaagttagaa ccagaagaat ttgcagcata tcttgaacca ttcaaagaga aaggtgaagt   2340
tcgtcgtcca acattatcat ggcctcgtga aatcccgtta gtaaaaggtg gtaaacctga   2400
cgttgtacaa attgttagga attataatgc ttatctacgt gcaagtgatg atttaccaaa   2460
aatgtttatt gaatcggacc caggattctt ttccaatgct attgttgaag gtgccaagaa   2520
gtttcctaat actgaatttg tcaaagtaaa aggtcttcat ttttcgcaag aagatgcacc   2580
tgatgaaatg ggaaaatata tcaaatcgtt cgttgagcga gttctcaaaa atgaacaata   2640
attctagagc ggccgcctcg agctcgctga tcagcctcga ctgtgccttc tagttgccag   2700
ccatctgttg tttgcccctc ccccgtgcct tccttgaccc tggaaggtgc cactcccact   2760
gtcctttcct aataaaatga ggaaattgca tcgcattgtc tgagtaggtg tcattctatt   2820
ctggggggtg gggtggggca ggacagcaag ggggaggatt gggaagacaa tagcaggcat   2880
gcttaattaa cctaaggcac tacgtcttct aaacctgcca agcgtgtgcg tgtacgtgcc   2940
aggaagtaat atgtgtgtgt gtatatatat atacatctat tgttgtgttt gtatgtcctg   3000
tgtttgtgtt tgttgtatga ttgcattgta tggtatgtat ggttgttgtt gtatgttgta   3060
tgttactata tttgttggta tgtggcatta aataaaatat gttttgtggt tctgtgtgtt   3120
atgtggttgc gccctagtga gtaacaactg tatttgtgtt tgtggtatgg gtgttgcttg   3180
ttgggctata tattgtcctg tatttcaagt tataaaactg cacaccttac agcatccatt   3240
ttatcctaca atcctccatt ttgctgtgca accgatttcg gttgcctttg gcttatgtct   3300
gtggttttct gcacaataca gtacgctggc actattgcaa actttaatct tttgggcact   3360
gctcctacat attttgaaca attggcgcgc ctctttggcg catataaggc gcacctggta   3420
ttagtcattt tcctgtccag gtgcgctaca acaattgctt gcataactat atccactccc   3480
taagtaataa aactgctttt aggcacatat tttagtttgt ttttacttaa gctaattgca   3540
tacttggctt gtacaactac tttcatgtcc aacattctgt ctacccttaa catgaactat   3600
atatgactaa gctgtgcata catagtttat gcaaccgaaa taggttgggc agcacatact   3660
atacttttca ttaatacttt taacaattgt agtatataaa aaagggagta accgaaaacg   3720
gtcgggaccg aaaacggtgt atataaaaga tgtgagaaac acaccacaat actatggcgc   3780
gctttgagga tccaacacgg cgaccctaca agctacctga tctgtgcacg gaactgaaca   3840
cttcactgca agacatagaa ataacctgtg tatattgcaa gacagtattg gaacttacag   3900
aggtatttga atttgcattt aaagatttat ttgtggtgta tagagacagt ataccccatg   3960
ctgcatgcca taaatgtata gatttttatt ctagaattag agaattaaga cattattcag   4020
actctgtgta tggagacaca ttggaaaaac taactaacac tgggttatac aatttattaa   4080
taaggtgcct gcggtgccag aaaccgttga atccagcaga aaaacttaga caccttaatg   4140
aaaaacgacg atttcacaac atagctgggc actatagagg ccagtgccat tcgtgctgca   4200
accgagcacg acaggaacga ctccaacgac gcagagaaac acaagtataa tattaagtat   4260
```

-continued gcatggacct aaggcaacat tgcaagacat tgtattgcat ttagagcccc aaaatgaaat 4320
tccggttgac cttctatgtc acgagcaatt aagcgactca gaggaagaaa acgatgaaat 4380
agatggagtt aatcatcaac atttaccagc ccgacgagcc gaaccacaac gtcacacaat 4440
gttgtgtatg tgttgtaagt gtgaagccag aattgagcta gtagtagaaa gctcagcaga 4500
cgaccttcga gcattccagc agctgtttct gaacaccctg tcctttgtgt gtccgtggtg 4560
tgcatcccag cagtaagcaa caatggctga tccagaaggt acagacgggg agggcacggg 4620
ttgtaacggc tggttttatg tacaagctat tgtagacaaa aaaacaggag atgtaatatc 4680
agatgacgag gacgaaaatg caacagacac agggtcggat atggtagatt ttattgatac 4740
acaaggaaca ttttgtgaac aggcagagct agagacagca caggcattgt tccatgcgca 4800
ggaggtccac aatgatgcac aagtgttgca tgttttaaaa cgaaagtttg caggaggcag 4860
cacagaaaac agtccattag gggagcggct ggaggtggat acagagttaa gtccacggtt 4920
acaagaaata tctttaaata gtgggcagaa aaaggcaaaa aggcggctgt ttacaatatc 4980
agatagtggc tatggctgtt ctgaagtgga agcaacacag attcaggtaa ctacaaatgg 5040
cgaacatggc ggcaatgtat gtagtggcgg cagtacggag gctatagaca acgggggcac 5100
agagggcaac aacagcagtg tagacggtac aagtgacaat agcaatatag aaaatgtaaa 5160
tccacaatgt accatagcac aattaaaaga cttgttaaaa gtaaacaata aacaaggagc 5220
tatgttagca gtatttaaag acacatatgg gctatcattt acagatttag ttagaaattt 5280
taaaagtgat aaaaccacgt gtacagattg ggttacagct atatttggag taaacccaac 5340
aatagcagaa ggatttaaaa cactaataca gccatttata ttatatgccc atattcaatg 5400
tctagactgt aaatggggag tattaatatt agccctgttg cgttacaaat gtggtaagag 5460
tagactaaca gttgctaaag gtttaagtac gttgttacac gtacctgaaa cttgtatgtt 5520
aattcaacca ccaaaattgc gaagtagtgt tgcagcacta tattggtata gaacaggaat 5580
atcaaatatt agtgaagtaa tgggagacac acctgagtgg atacaaagac ttactattat 5640
acaacatgga atagatgata gcaattttga tttgtcagaa atggtacaat gggcatttga 5700
taatgagctg acagatgaaa gcgatatggc atttgaatat gccttattag cagacagcaa 5760
cagcaatgca gctgcctttt taaaaagcaa ttgccaagct aaatatttaa aagattgtgc 5820
cacaatgtgc aaacattata ggcgagccca aaaacgacaa atgaatatgt cacagtggat 5880
acgatttaga tgttcaaaaa tagatgaagg gggagattgg agaccaatag tgcaattcct 5940
gcgataccaa caaatagagt ttataacatt tttaggagcc ttaaaatcat ttttaaaagg 6000
aacccccaaa aaaaattgtt tagtattttg tggaccagca aatacaggaa aatcatattt 6060
tggaatgagt tttatacact ttatacaagg agcagtaata tcatttgtga attccactag 6120
tcatttttgg ttggaaccgt taacagatac taaggtggcc atgttagatg atgcaacgac 6180
cacgtgttgg acatactttg atacctatat gagaaatgcg ttagatggca atccaataag 6240
tattgataga aagcacaaac cattaataca actaaaatgt cctccaatac tactaaccac 6300
aaatatacat ccagcaaagg ataatagatg gccatattta gaaagtagaa taacagtatt 6360
tgaatttcca aatgcatttc catttgataa aaatggcaat ccagtatatg aaataaatga 6420
caaaaattgg aaatgttttt ttgaaaggac atggtccaga ttagatttgc acgaggaaga 6480
ggaagatgca gacaccgaag gaaacccttt cggaacgttt aagttgcgtg caggacaaaa 6540
tcatagacca ctatgaaaat gacagtaaag acatagacag ccaaatacag tattggcaac 6600
taatacgttg ggaaaatgca atattctttg cagcaaggga acatggcata cagacattaa 6660

-continued accaccaggt ggtgccagcc tataacattt caaaaagtaa agcacataaa gctattgaac 6720
tgcaaatggc cctacaaggc cttgcacaaa gtcgatacaa aaccgaggat tggacactgc 6780
aagacacatg cgaggaacta tggaatacag aacctactca ctgctttaaa aaaggtggcc 6840
aaacagtaca agtatatttt gatggcaaca aagacaattg tatgacctat gtagcatggg 6900
acagtgtgta ttatatgact gatgcaggaa catgggacaa aaccgctacc tgtgtaagtc 6960
acaggggatt gtattatgta aaggaagggt acaacacgtt ttatatagaa tttaaaagtg 7020
aatgtgaaaa atatgggaac acaggtacgt gggaagtaca ttttgggaat aatgtaattg 7080
attgtaatga ctctatgtgc agtaccagtg acgacacggt atccgctact cagcttgtta 7140
aacagctaca gcacaccccc tcaccgtatt ccagcaccgt gtccgtgggc accgcaaaga 7200
cctacggcca gacgtcggct gctacacgac ctggacactg tggactcgcg gagaagcagc 7260
attgtggacc tgtcaaccca cttctcggtg cagctacacc tacaggcaac aacaaaagac 7320
ggaaactctg tagtggtaac actacgccta taatacattt aaaaggtgac agaaacagtt 7380
taaaatgttt acggtacaga ttgcgaaaac atagcgacca ctatagagat atatcatcca 7440
cctggcattg gacaggtgca ggcaatgaaa aaacaggaat actgactgta acataccata 7500
gtgaaacaca aagaacaaaa tttttaaata ctgttgcaat tccagatagt gtacaaatat 7560
tggtgggata catgacaatg taatacatat gctgtagtac caatatgtta tcacttattt 7620
ttttattttg cttttgtgta tgcatgtatg tgtgctgcca tgtcccgctt ttgccatctg 7680
tctgtatgtg tgcgtatgca tgggtattgg tatttgtgta tattgtggta ataacgtccc 7740
ctgccacagc attcacagta tatgtatttt gtttttttatt gcccatgtta ctattgcata 7800
tacatgctat attgtcttta cagtaattgt ataggttgtt ttatacagtg tattgtacat 7860
tgtatatttt gttttatacc ttttatgctt tttgtatttt tgtaataaaa gtatggtatc 7920
ccaccgtgcc gcacgacgca aacgggcttc ggtaactgac ttatataaaa catgtaaaca 7980
atctggtaca tgtccacctg atgttgttcc taaggtggag ggcaccacgt tagcagataa 8040
aatattgcaa tggtcaagcc ttggtatatt tttgggtgga cttggcatag gtactggcag 8100
tggtacaggg ggtcgtacag ggtacattcc attgggtggg cgttccaata cagtggtgga 8160
tgttggtcct acacgtcccc cagtggttat tgaacctgtg ggcccggatc caagctatct 8220
ctagagtcga cccatggggg cccgccccaa ctggggtaac ctttgagttc tctcagttgg 8280
gggtaatcag catcatgatg tggtaccaca tcatgatgct gattataaga atgcggccgc 8340
cacactctag tggatctcga gttaataatt cagaagaact cgtcaagaag gcgatagaag 8400
gcgatgcgct gcgaatcggg agcggcgata ccgtaaagca cgaggaagcg gtcagcccat 8460
tcgccgccaa gctcttcagc aatatcacgg gtagccaacg ctatgtcctg atagcggtcc 8520
gccacaccca gccggccaca gtcgatgaat ccagaaaagc ggccattttc caccatgata 8580
ttcggcaagc aggcatcgcc atgggtcacg acgagatcct cgccgtcggg catgctcgcc 8640
ttgagcctgg cgaacagttc ggctggcgcg agcccctgat gctcttcgtc cagatcatcc 8700
tgatcgacaa gaccggcttc catccgagta cgtgctcgct cgatgcgatg tttcgcttgg 8760
tggtcgaatg ggcaggtagc cggatcaagc gtatgcagcc gccgcattgc atcagccatg 8820
atggatactt tctcggcagg agcaaggtgt agatgacatg gagatcctgc cccggcactt 8880
cgcccaatag cagccagtcc cttcccgctt cagtgacaac gtcgagcaca gctgcgcaag 8940
gaacgcccgt cgtggccagc cacgatagcc gcgctgcctc gtcttgcagt tcattcaggg 9000

-continued

```
caccggacag gtcggtcttg acaaaaagaa ccgggcgccc ctgcgctgac agccggaaca   9060
cggcggcatc agagcagccg attgtctgtt gtgcccagtc atagccgaat agcctctcca   9120
cccaagcggc cggagaacct gcgtgcaatc catcttgttc aatcatgcga aacgatcctc   9180
atcctgtctc ttgatcagag cttgatcccc tgcgccatca gatccttggc ggcgagaaag   9240
ccatccagtt tactttgcag ggcttcccaa ccttaccaga gggcgcccca gctggcaatt   9300
ccggttcgct tgctgtccat aaaaccgccc agtctagcta tcgccatgta agcccactgc   9360
aagctacctg ctttctcttt gcgcttgcgt tttcccttgt ccagatagcc cagtagctga   9420
cattcatccg gggtcagcac cgtttctgcg gactggcttt ctacgtgctc gaggggggcc   9480
aaacggtctc cagcttggct gttttggcgg atgagagaag attttcagcc tgatacagat   9540
taaatcagaa cgcagaagcg gtctgataaa acagaatttg cctggcggca gtagcgcggt   9600
ggtcccacct gaccccatgc cgaactcaga agtgaaacgc cgtagcgccg atggtagtgt   9660
ggggtctccc catgcgagag tagggaactg ccaggcatca aataaaacga aaggctcagt   9720
cgaaagactg ggcctttcgt tttatctgtt gtttgtcggt gaacgctctc ctgagtagga   9780
caaatccgcc gggagcggat ttgaacgttg cgaagcaacg gcccggaggg tggcgggcag   9840
gacgcccgcc ataaactgcc aggcatcaaa ttaagcagaa ggccatcctg acggatggcc   9900
tttttgcgtt tctacaaact cttttgttta tttttctaaa tacattcaaa tatgtatccg   9960
ctcatgacca aaatccctta acgtgagttt tcgttccact gagcgtcaga ccccgtagaa  10020
aagatcaaag gatcttcttg agatcctttt tttctgcgcg taatctgctg cttgcaaaca  10080
aaaaaaccac cgctaccagc ggtggtttgt ttgccggatc aagagctacc aactcttttt  10140
ccgaaggtaa ctggcttcag cagagcgcag ataccaaata ctgtccttct agtgtagccg  10200
tagttaggcc accacttcaa gaactctgta gcaccgccta catacctcgc tctgctaatc  10260
ctgttaccag tggctgctgc cagtggcgat aagtcgtgtc ttaccgggtt ggactcaaga  10320
cgatagttac cggataaggc gcagcggtcg ggctgaacgg ggggttcgtg cacacagccc  10380
agcttggagc gaacgaccta caccgaactg agatacctac agcgtgagct atgagaaagc  10440
gccacgcttc ccgaagggag aaaggcggac aggtatccgg taagcggcag ggtcggaaca  10500
ggagagcgca cgagggagct tccaggggga aacgcctggt atctttatag tcctgtcggg  10560
tttcgccacc tctgacttga gcgtcgattt ttgtgatgct cgtcaggggg gcggagccta  10620
tggaaaaacg ccagcaacgc ggccttttta cggttcctgg ccttttgctg gccttttgct  10680
cacatgttct ttcctgcgtt atcccctgat tctgtggata accgtattac cgcctttgag  10740
tgagctgata ccgctcgccg cagccgaacg accgagcgca gcgagtcagt gagcgaggaa  10800
gcggaagagc gcctgatgcg gtattttctc cttacgcatc tgtgcggtat ttcacaccgc  10860
atatggtgca ctctcagtac aatctgctct gatgccgcat agttaagcca gtatacactc  10920
cgctatcgct acgtgactgg gtcatggctg cgccccgaca cccgccaaca cccgctgacg  10980
cgccctgacg ggcttgtctg ctcccggcat ccgcttacag acaagctgtg accgtctccg  11040
ggagctgcat gtgtcagagg ttttcaccgt catcaccgaa acgcgcgagg cagcagatca  11100
attcgcgcgc gaaggcgaag cggcatgcat aatgtgcctg tcaaatggac gaagcaggga  11160
ttctgcaaac cctatgctac tccgtcaagc cgtcaattgt ctgattcgtt accaattatg  11220
acaacttgac ggctacatca ttcacttttt cttcacaacc ggcacggaac tcgctcgggc  11280
tggccccggt gcatttttta aatacccgcg agaaatagag ttgatcgtca aaaccaacat  11340
tgcgaccgac ggtggcgata ggcatccggg tggtgctcaa aagcagcttc gcctggctga  11400
```

tacgttggtc ctcgcgccag cttaagacgc taatccctaa ctgctggcgg aaaagatgtg 11460
acagacgcga cggcgacaag caaacatgct gtgcgacgct ggcgat 11506

<210> SEQ ID NO 8
<211> LENGTH: 11122
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11122)
<223> OTHER INFORMATION: pMC_HPV18-RSV-Gluc

<400> SEQUENCE: 8
acattaccct gttatcccta gatgacatta ccctgttatc ccagatgaca ttaccctgtt 60
atccctagat gacattaccc tgttatccct agatgacatt taccctgtta tccctagatg 120
acattaccct gttatcccag atgacattac cctgttatcc ctagatacat taccctgtta 180
tcccagatga cataccctgt tatccctaga tgacattacc ctgttatccc agatgacatt 240
accctgttat ccctagatac attaccctgt tatcccagat gacataccct gttatcccta 300
gatgacatta ccctgttatc ccagatgaca ttaccctgtt atccctagat acattaccct 360
gttatcccag atgacatacc ctgttatccc tagatgacat taccctgtta tcccagatga 420
cattaccctg ttatccctag atacattacc ctgttatccc agatgacata ccctgttatc 480
cctagatgac attaccctgt tatcccagat gacattaccc tgttatccct agatacatta 540
ccctgttatc ccagatgaca taccctgtta tccctagatg acattaccct gttatcccag 600
atgacattac cctgttatcc ctagatacat taccctgtta tcccagatga cataccctgt 660
tatccctaga tgacattacc ctgttatccc agataaactc aatgatgatg atgatgatgg 720
tcgagactca gcggccgcgg tgccagggcg tgcccttggg ctccccgggc gcgactagtg 780
aattcagatc tgatagctta gatctcggct agcgtatacc ctcgacctgc aggtcgatcg 840
actctagtat ggtgcactct cagtacaatc tgctctgatg ccgcatagtt aagccagtat 900
ctgctccctg cttgtgtgtt ggaggtcgct gagtagtgcg cgagcaaaat ttaagctaca 960
acaaggcaag gcttgaccga caattgcatg aagaatctgc ttagggttag gcgttttgcg 1020
ctgcttcgcg atgtacgggc cagatatacg cgtatctgag gggactaggg tgtgtttagg 1080
cgaaaagcgg ggcttcggtt gtacgcggtt aggagtcccc tcaggatata gtagtttcgc 1140
ttttgcatag ggagggggaa atgtagtctt atgcaatact cttgtagtct tgcaacatgg 1200
taacgatgag ttagcaacat gccttacaag gagagaaaaa gcaccgtgca tgccgattgg 1260
tggaagtaag gtggtacgat cgtgccttat taggaaggca acagacgggt ctgacatgga 1320
ttggacgaac cactgaattc cgcattgcag agatattgta tttaagtgcc tagctcgata 1380
caataaacgc catttgacca ttcaccacat tggtgtgcac ctccaagctg gtagaggatc 1440
ggtcgatcga ctctagcgta tacggatcga tcctgcaggt cgactctaga caggtaagtg 1500
gcgtttctcg gggagccagc tgcgtccgct gtcgtgctgt cggtgtagta ctagcaagcg 1560
ttaagtcccc atctggctgc ggcctaccga agagtggtct tcacgtcaca cgctgtccca 1620
cgcacgtggt tggtttggtc gcttctggtt actgactact aagcagcctt ttcttttttc 1680
ctttcaggtt ctagacgcca ccatgggcgt gaaggtgctg ttcgccctga tctgtatcgc 1740
cgtggccgag gccaagccca ccgagaacaa cgaggacttc aacatcgtgg ccgtggccag 1800

-continued

```
caacttcgcc accacagacc tggacgccga cagaggcaag ctgcccggca agaaactgcc   1860
cctggaagtg ctgaaagaga tggaagccaa cgccagaaag gccggctgca ccagaggctg   1920
cctgatctgc ctgagccaca tcaagtgcac ccccaagatg aagaagttca tccccggcag   1980
atgccacacc tacgagggcg acaaagagag cgcccagggc ggcatcggcg aggccatcgt   2040
ggacatcccc gagatccccg gcttcaagga cctggaaccc atggaacagt ttatcgccca   2100
ggtggacctg tgcgtggact gcaccaccgg ctgtctgaag ggcctggcca acgtgcagtg   2160
cagcgacctg ctgaagaagt ggctgcccca gagatgcgcc accttcgcca gcaagatcca   2220
gggccaggtg gacaagatca agggcgctgg cggcgactga tgagcggccg cctcgagctc   2280
gctgatcagc ctcgactgtg ccttctagtt gccagccatc tgttgtttgc ccctcccccg   2340
tgccttcctt gaccctggaa ggtgccactc ccactgtcct ttcctaataa aatgaggaaa   2400
ttgcatcgca ttgtctgagt aggtgtcatt ctattctggg gggtggggtg gggcaggaca   2460
gcaaggggga ggattgggaa gacaatagca ggcatgctta attaacctaa ggcactacgt   2520
cttctaaacc tgccaagcgt gtgcgtgtac gtgccaggaa gtaatatgtg tgtgtgtata   2580
tatatataca tctattgttg tgtttgtatg tcctgtgttt gtgtttgttg tatgattgca   2640
ttgtatggta tgtatggttg ttgttgtatg ttgtatgtta ctatatttgt tggtatgtgg   2700
cattaaataa aatatgtttt gtggttctgt gtgttatgtg gttgcgccct agtgagtaac   2760
aactgtattt gtgtttgtgg tatgggtgtt gcttgttggg ctatatattg tcctgtattt   2820
caagttataa aactgcacac cttacagcat ccattttatc ctacaatcct ccattttgct   2880
gtgcaaccga tttcggttgc ctttggctta tgtctgtggt tttctgcaca atacagtacg   2940
ctggcactat tgcaaacttt aatcttttgg gcactgctcc tacatatttt gaacaattgg   3000
cgcgcctctt tggcgcatat aaggcgcacc tggtattagt cattttcctg tccaggtgcg   3060
ctacaacaat tgcttgcata actatatcca ctccctaagt aataaaactg cttttaggca   3120
catattttag tttgttttta cttaagctaa ttgcatactt ggcttgtaca actactttca   3180
tgtccaacat tctgtctacc cttaacatga actataatat gactaagctg tgcatacata   3240
gtttatgcaa ccgaaatagg ttgggcagca catactatac ttttcattaa tacttttaac   3300
aattgtagta tataaaaaag ggagtaaccg aaaacggtcg ggaccgaaaa cggtgtatat   3360
aaaagatgtg agaaacacac cacaatacta tggcgcgctt tgaggatcca acacggcgac   3420
cctacaagct acctgatctg tgcacggaac tgaacacttc actgcaagac atagaaataa   3480
cctgtgtata ttgcaagaca gtattggaac ttacagaggt atttgaattt gcatttaaag   3540
atttatttgt ggtgtataga gacagtatac cccatgctgc atgccataaa tgtatagatt   3600
tttattctag aattagagaa ttaagacatt attcagactc tgtgtatgga gacacattgg   3660
aaaaactaac taacactggg ttatacaatt tattaataag gtgcctgcgg tgccagaaac   3720
cgttgaatcc agcagaaaaa cttagacacc ttaatgaaaa acgacgattt cacaacatag   3780
ctgggcacta tagaggccag tgccattcgt gctgcaaccg agcacgacag gaacgactcc   3840
aacgacgcag agaaacacaa gtataatatt aagtatgcat ggacctaagg caacattgca   3900
agacattgta ttgcatttag agccccaaaa tgaaattccg gttgaccttc tatgtcacga   3960
gcaattaagc gactcagagg aagaaaacga tgaaatagat ggagttaatc atcaacattt   4020
accagcccga cgagccgaac cacaacgtca cacaatgttg tgtatgtgtt gtaagtgtga   4080
agccagaatt gagctagtag tagaaagctc agcagacgac cttcgagcat tccagcagct   4140
gtttctgaac accctgtcct ttgtgtgtcc gtggtgtgca tcccagcagt aagcaacaat   4200
```

```
ggctgatcca gaaggtacag acggggaggg cacgggttgt aacggctggt tttatgtaca   4260
agctattgta gacaaaaaaa caggagatgt aatatcagat gacgaggacg aaaatgcaac   4320
agacacaggg tcggatatgg tagattttat tgatacacaa ggaacatttt gtgaacaggc   4380
agagctagag acagcacagg cattgttcca tgcgcaggag gtccacaatg atgcacaagt   4440
gttgcatgtt ttaaaacgaa agtttgcagg aggcagcaca gaaaacagtc cattagggga   4500
gcggctggag gtggatacag agttaagtcc acggttacaa gaaatatctt taaatagtgg   4560
gcagaaaaag gcaaaaaggc ggctgtttac aatatcagat agtggctatg gctgttctga   4620
agtggaagca acacagattc aggtaactac aaatggcgaa catggcggca atgtatgtag   4680
tggcggcagt acggaggcta tagacaacgg gggcacagag ggcaacaaca gcagtgtaga   4740
cggtacaagt gacaatagca atatagaaaa tgtaaatcca caatgtacca tagcacaatt   4800
aaaagacttg ttaaaagtaa acaataaaca aggagctatg ttagcagtat ttaaagacac   4860
atatgggcta tcatttacag atttagttag aaattttaaa agtgataaaa ccacgtgtac   4920
agattgggtt acagctatat ttggagtaaa cccaacaata gcagaaggat ttaaaacact   4980
aatacagcca tttatattat atgcccatat tcaatgtcta gactgtaaat ggggagtatt   5040
aatattagcc ctgttgcgtt acaaatgtgg taagagtaga ctaacagttg ctaaaggttt   5100
aagtacgttg ttacacgtac ctgaaacttg tatgttaatt caaccaccaa aattgcgaag   5160
tagtgttgca gcactatatt ggtatagaac aggaatatca aatattagtg aagtaatggg   5220
agacacacct gagtggatac aaagacttac tattatacaa catggaatag atgatagcaa   5280
ttttgatttg tcagaaatgg tacaatgggc atttgataat gagctgacag atgaaagcga   5340
tatggcattt gaatatgcct tattagcaga cagcaacagc aatgcagctg cctttttaaa   5400
aagcaattgc caagctaaat atttaaaaga ttgtgccaca atgtgcaaac attataggcg   5460
agcccaaaaa cgacaaatga atatgtcaca gtggatacga tttagatgtt caaaaataga   5520
tgaaggggga gattggagac caatagtgca attcctgcga taccaacaaa tagagtttat   5580
aacattttta ggagccttaa aatcattttt aaaaggaacc cccaaaaaaa attgtttagt   5640
attttgtgga ccagcaaata caggaaaatc atattttgga atgagtttta tacactttat   5700
acaaggagca gtaatatcat ttgtgaattc cactagtcat tttggttgg aaccgttaac   5760
agatactaag gtggccatgt tagatgatgc aacgaccacg tgttggacat actttgatac   5820
ctatatgaga aatgcgttag atggcaatcc aataagtatt gatagaaagc acaaaccatt   5880
aatacaacta aaatgtcctc caatactact aaccacaaat atacatccag caaaggataa   5940
tagatggcca tatttagaaa gtagaataac agtatttgaa tttccaaatg catttccatt   6000
tgataaaaat ggcaatccag tatatgaaat aaatgacaaa aattggaaat gtttttttga   6060
aaggacatgg tccagattag atttgcacga ggaagaggaa gatgcagaca ccgaaggaaa   6120
ccctttcgga acgtttaagt tgcgtgcagg acaaaatcat agaccactat gaaaatgaca   6180
gtaaagacat agacagccaa atacagtatt ggcaactaat acgttgggaa aatgcaatat   6240
tctttgcagc aagggaacat ggcatacaga cattaaacca ccaggtggtg ccagcctata   6300
acatttcaaa aagtaaagca cataaagcta ttgaactgca aatggcccta caaggccttg   6360
cacaaagtcg atacaaaacc gaggattgga cactgcaaga cacatgcgag gaactatgga   6420
atacagaacc tactcactgc tttaaaaaag gtggccaaac agtacaagta tattttgatg   6480
gcaacaaaga caattgtatg acctatgtag catgggacag tgtgtattat atgactgatg   6540
```

```
caggaacatg ggacaaaacc gctacctgtg taagtcacag gggattgtat tatgtaaagg   6600
aagggtacaa cacgttttat atagaattta aaagtgaatg tgaaaaatat gggaacacag   6660
gtacgtggga agtacatttt gggaataatg taattgattg taatgactct atgtgcagta   6720
ccagtgacga cacggtatcc gctactcagc ttgttaaaca gctacagcac accccctcac   6780
cgtattccag caccgtgtcc gtgggcaccg caaagaccta cggccagacg tcggctgcta   6840
cacgacctgg acactgtgga ctcgcggaga agcagcattg tggacctgtc aacccacttc   6900
tcggtgcagc tacacctaca ggcaacaaca aaagacggaa actctgtagt ggtaacacta   6960
cgcctataat acatttaaaa ggtgacagaa acagtttaaa atgtttacgg tacagattgc   7020
gaaaacatag cgaccactat agagatatat catccacctg gcattggaca ggtgcaggca   7080
atgaaaaaac aggaatactg actgtaacat accatagtga aacacaaaga acaaaatttt   7140
taaatactgt tgcaattcca gatagtgtac aaatattggt gggatacatg acaatgtaat   7200
acatatgctg tagtaccaat atgttatcac ttattttttt attttgcttt tgtgtatgca   7260
tgtatgtgtg ctgccatgtc ccgcttttgc catctgtctg tatgtgtgcg tatgcatggg   7320
tattggtatt tgtgtatatt gtggtaataa cgtcccctgc cacagcattc acagtatatg   7380
tattttgttt tttattgccc atgttactat tgcatataca tgctatattg tctttacagt   7440
aattgtatag gttgttttat acagtgtatt gtacattgta tattttgttt tataccttttt   7500
atgctttttg tatttttgta ataaaagtat ggtatcccac cgtgccgcac gacgcaaacg   7560
ggcttcggta actgacttat ataaaacatg taaacaatct ggtacatgtc cacctgatgt   7620
tgttcctaag gtggagggca ccacgttagc agataaaata ttgcaatggt caagccttgg   7680
tatatttttg ggtggacttg gcataggtac tggcagtggt acagggggtc gtacagggta   7740
cattccattg ggtgggcgtt ccaatacagt ggtggatgtt ggtcctacac gtcccccagt   7800
ggttattgaa cctgtgggcc cggatccaag ctatctctag agtcgaccca tgggggcccg   7860
ccccaactgg ggtaaccttt gagttctctc agttgggggt aatcagcatc atgatgtggt   7920
accacatcat gatgctgatt ataagaatgc ggccgccaca ctctagtgga tctcgagtta   7980
ataattcaga agaactcgtc aagaaggcga tagaaggcga tgcgctgcga atcgggagcg   8040
gcgataccgt aaagcacgag gaagcggtca gcccattcgc cgccaagctc ttcagcaata   8100
tcacgggtag ccaacgctat gtcctgatag cggtccgcca cacccagccg gccacagtcg   8160
atgaatccag aaaagcggcc attttccacc atgatattcg gcaagcaggc atcgccatgg   8220
gtcacgacga gatcctcgcc gtcgggcatg ctcgccttga gcctggcgaa cagttcggct   8280
ggcgcgagcc cctgatgctc ttcgtccaga tcatcctgat cgacaagacc ggcttccatc   8340
cgagtacgtg ctcgctcgat gcgatgtttc gcttggtggt cgaatgggca ggtagccgga   8400
tcaagcgtat gcagccgccg cattgcatca gccatgatgg atactttctc ggcaggagca   8460
aggtgtagat gacatggaga tcctgccccg gcacttcgcc caatagcagc cagtcccttc   8520
ccgcttcagt gacaacgtcg agcacagctg cgcaaggaac gcccgtcgtg gccagccacg   8580
atagccgcgc tgcctcgtct tgcagttcat tcagggcacc ggacaggtcg gtcttgacaa   8640
aaagaaccgg gcgcccctgc gctgacagcc ggaacacggc ggcatcagag cagccgattg   8700
tctgttgtgc ccagtcatag ccgaatagcc tctccaccca agcggccgga gaacctgcgt   8760
gcaatccatc ttgttcaatc atgcgaaacg atcctcatcc tgtctcttga tcagagcttg   8820
atcccctgcg ccatcagatc cttggcggcg agaaagccat ccagtttact ttgcagggct   8880
tcccaacctt accagagggc gccccagctg gcaattccgg ttcgcttgct gtccataaaa   8940
```

-continued

```
ccgcccagtc tagctatcgc catgtaagcc cactgcaagc tacctgcttt ctctttgcgc   9000

ttgcgttttc ccttgtccag atagcccagt agctgacatt catccggggt cagcaccgtt   9060

tctgcggact ggctttctac gtgctcgagg ggggccaaac ggtctccagc ttggctgttt   9120

tggcggatga gagaagattt tcagcctgat acagattaaa tcagaacgca gaagcggtct   9180

gataaaacag aatttgcctg gcggcagtag cgcggtggtc ccacctgacc ccatgccgaa   9240

ctcagaagtg aaacgccgta gcgccgatgg tagtgtgggg tctccccatg cgagagtagg   9300

gaactgccag gcatcaaata aaacgaaagg ctcagtcgaa agactgggcc tttcgtttta   9360

tctgttgttt gtcggtgaac gctctcctga gtaggacaaa tccgccggga gcggatttga   9420

acgttgcgaa gcaacggccc ggagggtggc gggcaggacg cccgccataa actgccaggc   9480

atcaaattaa gcagaaggcc atcctgacgg atggcctttt tgcgtttcta caaactcttt   9540

tgtttatttt tctaaataca ttcaaatatg tatccgctca tgaccaaaat cccttaacgt   9600

gagttttcgt tccactgagc gtcagacccc gtagaaaaga tcaaaggatc ttcttgagat   9660

cctttttttc tgcgcgtaat ctgctgcttg caaacaaaaa aaccaccgct accagcggtg   9720

gtttgtttgc cggatcaaga gctaccaact ctttttccga aggtaactgg cttcagcaga   9780

gcgcagatac caaatactgt ccttctagtg tagccgtagt taggccacca cttcaagaac   9840

tctgtagcac cgcctacata cctcgctctg ctaatcctgt taccagtggc tgctgccagt   9900

ggcgataagt cgtgtcttac cgggttggac tcaagacgat agttaccgga taaggcgcag   9960

cggtcgggct gaacgggggg ttcgtgcaca cagcccagct tggagcgaac gacctacacc  10020

gaactgagat acctacagcg tgagctatga gaaagcgcca cgcttcccga agggagaaag  10080

gcggacaggt atccggtaag cggcagggtc ggaacaggag agcgcacgag ggagcttcca  10140

gggggaaacg cctggtatct ttatagtcct gtcgggtttc gccacctctg acttgagcgt  10200

cgatttttgt gatgctcgtc aggggggcgg agcctatgga aaaacgccag caacgcggcc  10260

tttttacggt tcctggcctt ttgctggcct tttgctcaca tgttctttcc tgcgttatcc  10320

cctgattctg tggataaccg tattaccgcc tttgagtgag ctgataccgc tcgccgcagc  10380

cgaacgaccg agcgcagcga gtcagtgagc gaggaagcgg aagagcgcct gatgcggtat  10440

tttctcctta cgcatctgtg cggtatttca caccgcatat ggtgcactct cagtacaatc  10500

tgctctgatg ccgcatagtt aagccagtat acactccgct atcgctacgt gactgggtca  10560

tggctgcgcc ccgacacccg ccaacacccg ctgacgcgcc ctgacgggct tgtctgctcc  10620

cggcatccgc ttacagacaa gctgtgaccg tctccgggag ctgcatgtgt cagaggtttt  10680

caccgtcatc accgaaacgc gcgaggcagc agatcaattc gcgcgcgaag gcgaagcggc  10740

atgcataatg tgcctgtcaa atggacgaag cagggattct gcaaacccta tgctactccg  10800

tcaagccgtc aattgtctga ttcgttacca attatgacaa cttgacggct acatcattca  10860

ctttttcttc acaaccggca cggaactcgc tcgggctggc cccggtgcat tttttaaata  10920

cccgcgagaa atagagttga tcgtcaaaac caacattgcg accgacggtg gcgataggca  10980

tccgggtggt gctcaaaagc agcttcgcct ggctgatacg ttggtcctcg cgccagctta  11040

agacgctaat ccctaactgc tggcggaaaa gatgtgacag acgcgacggc gacaagcaaa  11100

catgctgtgc gacgctggcg at                                           11122
```

<210> SEQ ID NO 9
<211> LENGTH: 11319
<212> TYPE: DNA

```
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11319)
<223> OTHER INFORMATION: pMC_HPV18-L2-Rluc

<400> SEQUENCE: 9

attaatactt ttaacaattg tagtatataa aaaagggagt aaccgaaaac ggtcgggacc      60

gaaaacggtg tatataaaag atgtgagaaa cacaccacaa tactatggcg cgctttgagg     120

atccaacacg gcgaccctac aagctacctg atctgtgcac ggaactgaac acttcactgc     180

aagacataga aataacctgt gtatattgca agacagtatt ggaacttaca gaggtatttg     240

aatttgcatt taaagattta tttgtggtgt atagagacag tataccgcat gctgcatgcc     300

ataaatgtat agatttttat tctagaatta gagaattaag acattattca gactctgtgt     360

atggagacac attggaaaaa ctaactaaca ctgggttata caatttatta ataaggtgcc     420

tgcggtgcca gaaaccgttg aatccagcag aaaaacttag acaccttaat gaaaaacgac     480

gatttcacaa catagctggg cactatagag gccagtgcca ttcgtgctgc aaccgagcac     540

gacaggaacg actccaacga cgcagagaaa cacaagtata atattaagta tgcatggacc     600

taaggcaaca ttgcaagaca ttgtattgca tttagagccc caaaatgaaa ttccggttga     660

ccttctatgt cacgagcaat taagcgactc agaggaagaa aacgatgaaa tagatggagt     720

taatcatcaa catttaccag cccgacgagc cgaaccacaa cgtcacacaa tgttgtgtat     780

gtgttgtaag tgtgaagcca gaattgagct agtagtagaa agctcagcag acgaccttcg     840

agcattccag cagctgtttc tgaacaccct gtcctttgtg tgtccgtggt gtgcatccca     900

gcagtaagca acaatggctg atccagaagg tacagacggg gagggcacgg gttgtaacgg     960

ctggttttat gtacaagcta ttgtagacaa aaaaacagga gatgtaatat cagatgacga    1020

ggacgaaaat gcaacagaca cagggtcgga tatggtagat tttattgata cacaaggaac    1080

attttgtgaa caggcagagc tagagacagc acaggcattg ttccatgcgc aggaggtcca    1140

caatgatgca caagtgttgc atgttttaaa acgaaagttt gcaggaggca gcacagaaaa    1200

cagtccatta ggggagcggc tggaggtgga tacagagtta agtccacggt tacaagaaat    1260

atctttaaat agtgggcaga aaaaggcaaa aaggcggctg tttacaatat cagatagtgg    1320

ctatggctgt tctgaagtgg aagcaacaca gattcaggta actacaaatg gcgaacatgg    1380

cggcaatgta tgtagtggcg gcagtacgga ggctatagac aacgggggca cagagggcaa    1440

caacagcagt gtagacggta caagtgacaa tagcaatata gaaaatgtaa atccacaatg    1500

taccatagca caattaaaag acttgttaaa agtaaacaat aaacaaggag ctatgttagc    1560

agtatttaaa gacacatatg ggctatcatt tacagattta gttagaaatt ttaaaagtga    1620

taaaaccacg tgtacagatt gggttacagc tatatttgga gtaaacccaa caatagcaga    1680

aggatttaaa acactaatac agccatttat attatatgcc catattcaat gtctagactg    1740

taaatgggga gtattaatat tagccctgtt gcgttacaaa tgtggtaaga gtagactaac    1800

agttgctaaa ggtttaagta cgttgttaca cgtacctgaa acttgtatgt taattcaacc    1860

accaaaattg cgaagtagtg ttgcagcact atattggtat agaacaggaa tatcaaatat    1920

tagtgaagta atgggagaca cacctgagtg gatacaaaga cttactatta tacaacatgg    1980

aatagatgat agcaattttg atttgtcaga aatggtacaa tgggcatttg ataatgagct    2040

gacagatgaa agcgatatgg catttgaata tgccttatta gcagacagca acagcaatgc    2100
```

-continued

```
agctgccttt ttaaaaagca attgccaagc taaatattta aaagattgtg ccacaatgtg   2160
caaacattat aggcgagccc aaaaacgaca aatgaatatg tcacagtgga tacgatttag   2220
atgttcaaaa atagatgaag ggggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagtgcgtt gcaggacaaa atcatagacc   2880
actatgaaaa tgacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtgcataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaacggctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctacac ctacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa atttttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgttttttat tgcccatgtt actattgcat atacatgcta   4140
tattgtcttt acagtaattg tataggttgt tttatacagt gtattgtaca ttgtatattt   4200
tgttttatac cttttatgct ttttgtattt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
```

-continued

```
gggtcgtaca gggtacattc cattgggtgg gcgttccaat acagtggtgg atgttggtcc   4500
tacacgtccc ccagtggtta ttgaacctgt gggccccaca gacccatcta ttgttacatt   4560
aatagaggac tccagtgtgg ttacatcagg tgcacctagg cctacgttta ctggcacgtc   4620
tgggtttgat ataacatctg cgggtacaac tacacctgcg gttttggata tcacaccttc   4680
gtctacctct gtgtctattt ccacaaccaa ttttaccaat cctgcatttt ctgatccgtc   4740
cattattgaa gttccacaaa ctggggaggt ggcaggtaat gtatttgttg gtacccctac   4800
atctggaaca catgggtatg aggaaatacc tttacaaaca tttgcttctt ctggtacggg   4860
ggaggaaccc attagtagta ccccattgcc tactgtgcgg cgtgtagcag gtcccgacct   4920
cgtgaaataa aagtgcagaa aacaaaccca ggcgatcaca gcagcagccg ccgcggcagc   4980
agcaccaaca gcaggaggag caggaggagc cggaggagga ggaggaggag gaggcaaagt   5040
tagagttggg gctggcgctc cggagttgct gggctcagcg cagctcccat tcattaagga   5100
accagctgcg gaggaaggtg gccgagcgcc cgcgctgccc actcgctcgc tcgcgcactc   5160
agacgcgcgc cacaacagcg cgccccaagc tgcgcagctc tgcaaaagtt tctgctcggg   5220
atctggctct cttccccttg gactttagaa cgatttaggg ttgacagagg aaagcagagg   5280
cgcgcaggag gagcagaaaa caccaccttc tgcagttgga ggcaggcagc cccggctgca   5340
ctctagccgc cgcgcccgga gccggggccg acccgccact atccgcagca gcctcggcca   5400
ggaggcgacc cgggcgcctg ggtgtgtggc tgctgttgcg ggacgtcttc gcggggcggg   5460
aggctcgcgc cgcagccagc gccatggcca cttcgaaagt ttatgatcca gaacaaagga   5520
aacggatgat aactggtccg cagtggtggg ccagatgtaa acaaatgaat gttcttgatt   5580
catttattaa ttattatgat tcagaaaaac atgcagaaaa tgctgttatt tttttacatg   5640
gtaacgcggc ctcttcttat ttatggcgac atgttgtgcc acatattgag ccagtagcgc   5700
ggtgtattat accagacctt attggtatgg gcaaatcagg caaatctggt aatggttctt   5760
ataggttact tgatcattac aaatatctta ctgcatggtt tgaacttctt aatttaccaa   5820
agaagatcat tttgtcggc catgattggg gtgcttgttt ggcatttcat tatagctatg   5880
agcatcaaga taagatcaaa gcaatagttc acgctgaaag tgtagtagat gtgattgaat   5940
catgggatga atggcctgat attgaagaag atattgcgtt gatcaaatct gaagaaggag   6000
aaaaaatggt tttggagaat aacttcttcg tggaaaccat gttgccatca aaaatcatga   6060
gaaagttaga accagaagaa tttgcagcat atcttgaacc attcaaagag aaaggtgaag   6120
ttcgtcgtcc aacattatca tggcctcgtg aaatcccgtt agtaaaaggt ggtaaacctg   6180
acgttgtaca aattgttagg aattataatg cttatctacg tgcaagtgat gatttaccaa   6240
aaatgtttat tgaatcggac ccaggattct tttccaatgc tattgttgaa ggtgccaaga   6300
agtttcctaa tactgaattt gtcaaagtaa aaggtcttca tttttcgcaa gaagatgcac   6360
ctgatgaaat gggaaaatat atcaaatcgt tcgttgagcg agttctcaaa aatgaacaat   6420
aattctagag cggccgcaag cttaattaac gtctcgcact acgtcttcta aacctgccaa   6480
gcgtgtgcgt gtacgtgcca ggaagtaata tgtgtgtgtg tatatatata tacatctatt   6540
gttgtgtttg tatgtcctgt gtttgtgttt gttgtatgat tgcattgtat ggtatgtatg   6600
gttgttgttg tatgttgtat gttactatat ttgttggtat gtggcattaa ataaaatatg   6660
ttttgtggtt ctgtgtgtta tgtggttgcg ccctagtgag taacaactgt atttgtgttt   6720
gtggtatggg tgttgcttgt tgggctatat attgtcctgt atttcaagtt ataaaactgc   6780
acaccttaca gcatccattt tatcctacaa tcctccattt tgctgtgcaa ccgatttcgg   6840
```

```
ttgccagatc tgatatctct agagtcgacc catgggggcc cgccccaact ggggtaacct   6900
ttgagttctc tcagttgggg gtaatcagca tcatgatgtg gtaccacatc atgatgctga   6960
ttataagaat gcggccgcca cactctagtg gatctcgagt taataattca gaagaactcg   7020
tcaagaaggc gatagaaggc gatgcgctgc gaatcgggag cggcgatacc gtaaagcacg   7080
aggaagcggt cagcccattc gccgccaagc tcttcagcaa tatcacgggt agccaacgct   7140
atgtcctgat agcggtccgc cacacccagc cggccacagt cgatgaatcc agaaaagcgg   7200
ccattttcca ccatgatatt cggcaagcag gcatcgccat gggtcacgac gagatcctcg   7260
ccgtcgggca tgctcgcctt gagcctggcg aacagttcgg ctggcgcgag cccctgatgc   7320
tcttcgtcca gatcatcctg atcgacaaga ccggcttcca tccgagtacg tgctcgctcg   7380
atgcgatgtt tcgcttggtg gtcgaatggg caggtagccg gatcaagcgt atgcagccgc   7440
cgcattgcat cagccatgat ggatactttc tcggcaggag caaggtgtag atgacatgga   7500
gatcctgccc cggcacttcg cccaatagca gccagtccct tcccgcttca gtgacaacgt   7560
cgagcacagc tgcgcaagga acgcccgtcg tggccagcca cgatagccgc gctgcctcgt   7620
cttgcagttc attcagggca ccggacaggt cggtcttgac aaaaagaacc gggcgcccct   7680
gcgctgacag ccggaacacg gcggcatcag agcagccgat tgtctgttgt gcccagtcat   7740
agccgaatag cctctccacc caagcggccg gagaacctgc gtgcaatcca tcttgttcaa   7800
tcatgcgaaa cgatcctcat cctgtctctt gatcagagct tgatcccctg cgccatcaga   7860
tccttggcgg cgagaaagcc atccagttta ctttgcaggg cttcccaacc ttaccagagg   7920
gcgccccagc tggcaattcc ggttcgcttg ctgtccataa aaccgcccag tctagctatc   7980
gccatgtaag cccactgcaa gctacctgct ttctctttgc gcttgcgttt tcccttgtcc   8040
agatagccca gtagctgaca ttcatccggg gtcagcaccg tttctgcgga ctggctttct   8100
acgtgctcga ggggggccaa acggtctcca gcttggctgt tttggcggat gagagaagat   8160
tttcagcctg atacagatta aatcagaacg cagaagcggt ctgataaaac agaatttgcc   8220
tggcggcagt agcgcggtgg tcccacctga ccccatgccg aactcagaag tgaaacgccg   8280
tagcgccgat ggtagtgtgg ggtctcccca tgcgagagta gggaactgcc aggcatcaaa   8340
taaaacgaaa ggctcagtcg aaagactggg cctttcgttt tatctgttgt ttgtcggtga   8400
acgctctcct gagtaggaca aatccgccgg gagcggattt gaacgttgcg aagcaacggc   8460
ccggagggtg gcgggcagga cgcccgccat aaactgccag gcatcaaatt aagcagaagg   8520
ccatcctgac ggatggcctt tttgcgtttc tacaaactct tttgtttatt tttctaaata   8580
cattcaaata tgtatccgct catgaccaaa atcccttaac gtgagttttc gttccactga   8640
gcgtcagacc ccgtagaaaa gatcaaagga tcttcttgag atcctttttt tctgcgcgta   8700
atctgctgct tgcaaacaaa aaaaccaccg ctaccagcgg tggtttgttt gccggatcaa   8760
gagctaccaa ctctttttcc gaaggtaact ggcttcagca gagcgcagat accaaatact   8820
gtccttctag tgtagccgta gttaggccac cacttcaaga actctgtagc accgcctaca   8880
tacctcgctc tgctaatcct gttaccagtg gctgctgcca gtggcgataa gtcgtgtctt   8940
accgggttgg actcaagacg atagttaccg gataaggcgc agcggtcggg ctgaacgggg   9000
ggttcgtgca cacagcccag cttggagcga acgacctaca ccgaactgag atacctacag   9060
cgtgagctat gagaaagcgc cacgcttccc gaagggagaa aggcggacag gtatccggta   9120
agcggcaggg tcggaacagg agagcgcacg agggagcttc cagggggaaa cgcctggtat   9180
```

-continued

```
ctttatagtc ctgtcgggtt tcgccacctc tgacttgagc gtcgattttt gtgatgctcg   9240
tcaggggggc ggagcctatg gaaaaacgcc agcaacgcgg cctttttacg gttcctggcc   9300
ttttgctggc cttttgctca catgttcttt cctgcgttat cccctgattc tgtggataac   9360
cgtattaccg cctttgagtg agctgatacc gctcgccgca gccgaacgac cgagcgcagc   9420
gagtcagtga gcgaggaagc ggaagagcgc ctgatgcggt attttctcct tacgcatctg   9480
tgcggtattt cacaccgcat atggtgcact ctcagtacaa tctgctctga tgccgcatag   9540
ttaagccagt atacactccg ctatcgctac gtgactgggt catggctgcg ccccgacacc   9600
cgccaacacc cgctgacgcg ccctgacggg cttgtctgct cccggcatcc gcttacagac   9660
aagctgtgac cgtctccggg agctgcatgt gtcagaggtt ttcaccgtca tcaccgaaac   9720
gcgcgaggca gcagatcaat tcgcgcgcga aggcgaagcg gcatgcataa tgtgcctgtc   9780
aaatggacga agcagggatt ctgcaaaccc tatgctactc cgtcaagccg tcaattgtct   9840
gattcgttac caattatgac aacttgacgg ctacatcatt cactttttct tcacaaccgg   9900
cacggaactc gctcgggctg gccccggtgc atttttaaa tacccgcgag aaatagagtt   9960
gatcgtcaaa accaacattg cgaccgacgg tggcgatagg catccgggtg gtgctcaaaa  10020
gcagcttcgc ctggctgata cgttggtcct cgcgccagct taagacgcta atccctaact  10080
gctggcggaa aagatgtgac agacgcgacg gcgacaagca aacatgctgt gcgacgctgg  10140
cgatacatta ccctgttatc cctagatgac attaccctgt tatcccagat gacattaccc  10200
tgttatccct agatgacatt accctgttat ccctagatga catttaccct gttatcccta  10260
gatgacatta ccctgttatc ccagatgaca ttaccctgtt atccctagat acattaccct  10320
gttatcccag atgacatacc ctgttatccc tagatgacat taccctgtta tcccagatga  10380
cattaccctg ttatccctag atacattacc ctgttatccc agatgacata ccctgttatc  10440
cctagatgac attaccctgt tatcccagat gacattaccc tgttatccct agatacatta  10500
ccctgttatc ccagatgaca taccctgtta tccctagatg acattaccct gttatcccag  10560
atgacattac cctgttatcc ctagatacat taccctgtta tcccagatga cataccctgt  10620
tatccctaga tgacattacc ctgttatccc agatgacatt accctgttat ccctagatac  10680
attaccctgt tatcccagat gacataccct gttatcccta gatgacatta ccctgttatc  10740
ccagatgaca ttaccctgtt atccctagat acattaccct gttatcccag atgacatacc  10800
ctgttatccc tagatgacat taccctgtta tcccagataa actcaatgat gatgatgatg  10860
atggtcgaga ctcagcggcc gcggtgccag ggcgtgccct tgggctcccc gggcgcgact  10920
agtgaattca gatcttttgg cttatgtctg tggttttctg cacaatacag tacgctggca  10980
ctattgcaaa ctttaatctt ttgggcactg ctcctacata ttttgaacaa ttggcgcgcc  11040
tctttggcgc atataaggcg cacctggtat tagtcatttt cctgtccagg tgcgctacaa  11100
caattgcttg cataactata tccactccct aagtaataaa actgctttta ggcacatatt  11160
ttagtttgtt tttacttaag ctaattgcat acttggcttg tacaactact ttcatgtcca  11220
acattctgtc taccccttaac atgaactata atatgactaa gctgtgcata catagtttat  11280
gcaaccgaaa taggttgggc agcacatact atactttttc                           11319
```

<210> SEQ ID NO 10
<211> LENGTH: 11541
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(11541)
<223> OTHER INFORMATION: pMC_HPV18-L2-Rluc-pA

<400> SEQUENCE: 10
attaatactt ttaacaattg tagtatataa aaaagggagt aaccgaaaac ggtcgggacc 60
gaaaacggtg tatataaaag atgtgagaaa cacaccacaa tactatggcg cgctttgagg 120
atccaacacg gcgaccctac aagctacctg atctgtgcac ggaactgaac acttcactgc 180
aagacataga aataacctgt gtatattgca agacagtatt ggaacttaca gaggtatttg 240
aatttgcatt taaagattta tttgtggtgt atagagacag tataccgcat gctgcatgcc 300
ataaatgtat agatttttat tctagaatta gagaattaag acattattca gactctgtgt 360
atggagacac attggaaaaa ctaactaaca ctgggttata caatttatta ataaggtgcc 420
tgcggtgcca gaaaccgttg aatccagcag aaaaacttag acaccttaat gaaaaacgac 480
gatttcacaa catagctggg cactatagag gccagtgcca ttcgtgctgc aaccgagcac 540
gacaggaacg actccaacga cgcagagaaa cacaagtata atattaagta tgcatggacc 600
taaggcaaca ttgcaagaca ttgtattgca tttagagccc caaaatgaaa ttccggttga 660
ccttctatgt cacgagcaat taagcgactc agaggaagaa aacgatgaaa tagatggagt 720
taatcatcaa catttaccag cccgacgagc cgaaccacaa cgtcacacaa tgttgtgtat 780
gtgttgtaag tgtgaagcca gaattgagct agtagtagaa agctcagcag acgaccttcg 840
agcattccag cagctgtttc tgaacaccct gtcctttgtg tgtccgtggt gtgcatccca 900
gcagtaagca acaatggctg atccagaagg tacagacggg gagggcacgg gttgtaacgg 960
ctggttttat gtacaagcta ttgtagacaa aaaaacagga gatgtaatat cagatgacga 1020
ggacgaaaat gcaacagaca cagggtcgga tatggtagat tttattgata cacaaggaac 1080
attttgtgaa caggcagagc tagagacagc acaggcattg ttccatgcgc aggaggtcca 1140
caatgatgca caagtgttgc atgttttaaa acgaaagttt gcaggaggca gcacagaaaa 1200
cagtccatta ggggagcggc tggaggtgga tacagagtta agtccacggt tacaagaaat 1260
atctttaaat agtgggcaga aaaaggcaaa aaggcggctg tttacaatat cagatagtgg 1320
ctatggctgt tctgaagtgg aagcaacaca gattcaggta actacaaatg gcgaacatgg 1380
cggcaatgta tgtagtggcg gcagtacgga ggctatagac aacgggggca cagagggcaa 1440
caacagcagt gtagacggta caagtgacaa tagcaatata gaaaatgtaa atccacaatg 1500
taccatagca caattaaaag acttgttaaa agtaaacaat aaacaaggag ctatgttagc 1560
agtatttaaa gacacatatg ggctatcatt tacagattta gttagaaatt ttaaaagtga 1620
taaaaccacg tgtacagatt gggttacagc tatatttgga gtaaacccaa caatagcaga 1680
aggatttaaa acactaatac agccatttat attatatgcc catattcaat gtctagactg 1740
taaatgggga gtattaatat tagccctgtt gcgttacaaa tgtggtaaga gtagactaac 1800
agttgctaaa ggtttaagta cgttgttaca cgtacctgaa acttgtatgt taattcaacc 1860
accaaaattg cgaagtagtg ttgcagcact atattggtat agaacaggaa tatcaaatat 1920
tagtgaagta atgggagaca cacctgagtg gatacaaaga cttactatta tacaacatgg 1980
aatagatgat agcaattttg atttgtcaga aatggtacaa tgggcatttg ataatgagct 2040
gacagatgaa agcgatatgg catttgaata tgccttatta gcagacagca acagcaatgc 2100
agctgccttt ttaaaaagca attgccaagc taaatattta aaagattgtg ccacaatgtg 2160

-continued

```
caaacattat aggcgagccc aaaaacgaca aatgaatatg tcacagtgga tacgatttag   2220
atgttcaaaa atagatgaag ggggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagtgcgtt gcaggacaaa atcatagacc   2880
actatgaaaa tgacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtgcataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaacggctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctacac ctacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa atttttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgttttttat tgcccatgtt actattgcat atacatgcta   4140
tattgtcttt acagtaattg tataggttgt tttatacagt gtattgtaca ttgtatattt   4200
tgttttatac cttttatgct ttttgtattt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
gggtcgtaca gggtacattc cattgggtgg gcgttccaat acagtggtgg atgttggtcc   4500
tacacgtccc ccagtggtta ttgaacctgt gggccccaca gacccatcta ttgttacatt   4560
```

```
aatagaggac tccagtgtgg ttacatcagg tgcacctagg cctacgttta ctggcacgtc   4620
tgggtttgat ataacatctg cgggtacaac tacacctgcg gttttggata tcacaccttc   4680
gtctacctct gtgtctattt ccacaaccaa ttttaccaat cctgcatttt ctgatccgtc   4740
cattattgaa gttccacaaa ctggggaggt ggcaggtaat gtatttgttg gtacccctac   4800
atctggaaca catgggtatg aggaaatacc tttacaaaca tttgcttctt ctggtacggg   4860
ggaggaaccc attagtagta ccccattgcc tactgtgcgg cgtgtagcag gtcccgacct   4920
cgtgaaataa aagtgcagaa aacaaaccca ggcgatcaca gcagcagccg ccgcggcagc   4980
agcaccaaca gcaggaggag caggaggagc cggaggagga ggaggaggag gaggcaaagt   5040
tagagttggg gctggcgctc cggagttgct gggctcagcg cagctcccat tcattaagga   5100
accagctgcg gaggaaggtg gccgagcgcc cgcgctgccc actcgctcgc tcgcgcactc   5160
agacgcgcgc cacaacagcg cgccccaagc tgcgcagctc tgcaaaagtt tctgctcggg   5220
atctggctct cttccccttg gactttagaa cgatttaggg ttgacagagg aaagcagagg   5280
cgcgcaggag gagcagaaaa caccaccttc tgcagttgga ggcaggcagc cccggctgca   5340
ctctagccgc cgcgcccgga gccggggccg acccgccact atccgcagca gcctcggcca   5400
ggaggcgacc cgggcgcctg ggtgtgtggc tgctgttgcg ggacgtcttc gcggggcggg   5460
aggctcgcgc cgcagccagc gccatggcca cttcgaaagt ttatgatcca gaacaaagga   5520
aacggatgat aactggtccg cagtggtggg ccagatgtaa acaaatgaat gttcttgatt   5580
catttattaa ttattatgat tcagaaaaac atgcagaaaa tgctgttatt tttttacatg   5640
gtaacgcggc ctcttcttat ttatggcgac atgttgtgcc acatattgag ccagtagcgc   5700
ggtgtattat accagacctt attggtatgg gcaaatcagg caaatctggt aatggttctt   5760
ataggttact tgatcattac aaatatctta ctgcatggtt tgaacttctt aatttaccaa   5820
agaagatcat ttttgtcggc catgattggg gtgcttgttt ggcatttcat tatagctatg   5880
agcatcaaga taagatcaaa gcaatagttc acgctgaaag tgtagtagat gtgattgaat   5940
catgggatga atggcctgat attgaagaag atattgcgtt gatcaaatct gaagaaggag   6000
aaaaaatggt tttggagaat aacttcttcg tggaaaccat gttgccatca aaaatcatga   6060
gaaagttaga accagaagaa tttgcagcat atcttgaacc attcaaagag aaaggtgaag   6120
ttcgtcgtcc aacattatca tggcctcgtg aaatcccgtt agtaaaaggt ggtaaacctg   6180
acgttgtaca aattgttagg aattataatg cttatctacg tgcaagtgat gatttaccaa   6240
aaatgtttat tgaatcggac ccaggattct tttccaatgc tattgttgaa ggtgccaaga   6300
agtttcctaa tactgaattt gtcaaagtaa aaggtcttca tttttcgcaa gaagatgcac   6360
ctgatgaaat gggaaaatat atcaaatcgt tcgttgagcg agttctcaaa aatgaacaat   6420
aattctagag cggccgcctc gagctcgctg atcagcctcg actgtgcctt ctagttgcca   6480
gccatctgtt gtttgcccct cccccgtgcc ttccttgacc ctggaaggtg ccactcccac   6540
tgtcctttcc taataaaatg aggaaattgc atcgcattgt ctgagtaggt gtcattctat   6600
tctggggggt ggggtggggc aggacagcaa gggggaggat tgggaagaca atagcaggca   6660
tgcttaatta acgtctcgca ctacgtcttc taaacctgcc aagcgtgtgc gtgtacgtgc   6720
caggaagtaa tatgtgtgtg tgtatatata tatacatcta ttgttgtgtt tgtatgtcct   6780
gtgtttgtgt ttgttgtatg attgcattgt atggtatgta tggttgttgt tgtatgttgt   6840
atgttactat atttgttggt atgtggcatt aaataaaata tgttttgtgg ttctgtgtgt   6900
```

```
tatgtggttg cgccctagtg agtaacaact gtatttgtgt ttgtggtatg ggtgttgctt   6960
gttgggctat atattgtcct gtatttcaag ttataaaact gcacacctta cagcatccat   7020
tttatcctac aatcctccat tttgctgtgc aaccgatttc ggttgccaga tctgatatct   7080
ctagagtcga cccatggggg cccgccccaa ctggggtaac ctttgagttc tctcagttgg   7140
gggtaatcag catcatgatg tggtaccaca tcatgatgct gattataaga atgcggccgc   7200
cacactctag tggatctcga gttaataatt cagaagaact cgtcaagaag gcgatagaag   7260
gcgatgcgct gcgaatcggg agcggcgata ccgtaaagca cgaggaagcg gtcagcccat   7320
tcgccgccaa gctcttcagc aatatcacgg gtagccaacg ctatgtcctg atagcggtcc   7380
gccacaccca gccggccaca gtcgatgaat ccagaaaagc ggccattttc caccatgata   7440
ttcggcaagc aggcatcgcc atgggtcacg acgagatcct cgccgtcggg catgctcgcc   7500
ttgagcctgg cgaacagttc ggctggcgcg agcccctgat gctcttcgtc cagatcatcc   7560
tgatcgacaa gaccggcttc catccgagta cgtgctcgct cgatgcgatg tttcgcttgg   7620
tggtcgaatg ggcaggtagc cggatcaagc gtatgcagcc gccgcattgc atcagccatg   7680
atggatactt tctcggcagg agcaaggtgt agatgacatg gagatcctgc cccggcactt   7740
cgcccaatag cagccagtcc cttcccgctt cagtgacaac gtcgagcaca gctgcgcaag   7800
gaacgcccgt cgtggccagc cacgatagcc gcgctgcctc gtcttgcagt tcattcaggg   7860
caccggacag gtcggtcttg acaaaaagaa ccgggcgccc ctgcgctgac agccggaaca   7920
cggcggcatc agagcagccg attgtctgtt gtgcccagtc atagccgaat agcctctcca   7980
cccaagcggc cggagaacct gcgtgcaatc catcttgttc aatcatgcga aacgatcctc   8040
atcctgtctc ttgatcagag cttgatcccc tgcgccatca gatccttggc ggcgagaaag   8100
ccatccagtt tactttgcag ggcttcccaa ccttaccaga gggcgcccca gctggcaatt   8160
ccggttcgct tgctgtccat aaaaccgccc agtctagcta tcgccatgta agcccactgc   8220
aagctacctg ctttctcttt gcgcttgcgt tttcccttgt ccagatagcc cagtagctga   8280
cattcatccg gggtcagcac cgtttctgcg gactggcttt ctacgtgctc gaggggggcc   8340
aaacggtctc cagcttggct gttttggcgg atgagagaag attttcagcc tgatacagat   8400
taaatcagaa cgcagaagcg gtctgataaa acagaatttg cctggcggca gtagcgcggt   8460
ggtcccacct gaccccatgc cgaactcaga agtgaaacgc cgtagcgccg atggtagtgt   8520
ggggtctccc catgcgagag tagggaactg ccaggcatca aataaaacga aaggctcagt   8580
cgaaagactg ggcctttcgt tttatctgtt gtttgtcggt gaacgctctc ctgagtagga   8640
caaatccgcc gggagcggat ttgaacgttg cgaagcaacg gcccggaggg tggcgggcag   8700
gacgcccgcc ataaactgcc aggcatcaaa ttaagcagaa ggccatcctg acggatggcc   8760
tttttgcgtt tctacaaact cttttgttta tttttctaaa tacattcaaa tatgtatccg   8820
ctcatgacca aaatccctta acgtgagttt tcgttccact gagcgtcaga ccccgtagaa   8880
aagatcaaag gatcttcttg agatcctttt tttctgcgcg taatctgctg cttgcaaaca   8940
aaaaaaccac cgctaccagc ggtggtttgt ttgccggatc aagagctacc aactcttttt   9000
ccgaaggtaa ctggcttcag cagagcgcag ataccaaata ctgtccttct agtgtagccg   9060
tagttaggcc accacttcaa gaactctgta gcaccgccta catacctcgc tctgctaatc   9120
ctgttaccag tggctgctgc cagtggcgat aagtcgtgtc ttaccgggtt ggactcaaga   9180
cgatagttac cggataaggc gcagcggtcg ggctgaacgg ggggttcgtg cacacagccc   9240
agcttggagc gaacgaccta caccgaactg agatacctac agcgtgagct atgagaaagc   9300
```

```
gccacgcttc ccgaagggag aaaggcggac aggtatccgg taagcggcag ggtcggaaca   9360
ggagagcgca cgagggagct tccaggggga aacgcctggt atctttatag tcctgtcggg   9420
tttcgccacc tctgacttga gcgtcgattt ttgtgatgct cgtcaggggg gcggagccta   9480
tggaaaaacg ccagcaacgc ggccttttta cggttcctgg ccttttgctg gccttttgct   9540
cacatgttct ttcctgcgtt atcccctgat tctgtggata accgtattac cgcctttgag   9600
tgagctgata ccgctcgccg cagccgaacg accgagcgca gcgagtcagt gagcgaggaa   9660
gcggaagagc gcctgatgcg gtattttctc cttacgcatc tgtgcggtat ttcacaccgc   9720
atatggtgca ctctcagtac aatctgctct gatgccgcat agttaagcca gtatacactc   9780
cgctatcgct acgtgactgg gtcatggctg cgccccgaca cccgccaaca cccgctgacg   9840
cgccctgacg ggcttgtctg ctcccggcat ccgcttacag acaagctgtg accgtctccg   9900
ggagctgcat gtgtcagagg ttttcaccgt catcaccgaa acgcgcgagg cagcagatca   9960
attcgcgcgc gaaggcgaag cggcatgcat aatgtgcctg tcaaatggac gaagcaggga  10020
ttctgcaaac cctatgctac tccgtcaagc cgtcaattgt ctgattcgtt accaattatg  10080
acaacttgac ggctacatca ttcacttttt cttcacaacc ggcacggaac tcgctcgggc  10140
tggccccggt gcattttttta aatacccgcg agaaatagag ttgatcgtca aaaccaacat  10200
tgcgaccgac ggtggcgata ggcatccggg tggtgctcaa aagcagcttc gcctggctga  10260
tacgttggtc ctcgcgccag cttaagacgc taatccctaa ctgctggcgg aaaagatgtg  10320
acagacgcga cggcgacaag caaacatgct gtgcgacgct ggcgatacat taccctgtta  10380
tccctagatg acattaccct gttatcccag atgacattac cctgttatcc ctagatgaca  10440
ttaccctgtt atccctagat gacatttacc ctgttatccc tagatgacat taccctgtta  10500
tcccagatga cattaccctg ttatccctag atacattacc ctgttatccc agatgacata  10560
ccctgttatc cctagatgac attaccctgt tatcccagat gacattaccc tgttatccct  10620
agatacatta ccctgttatc ccagatgaca taccctgtta tccctagatg acattaccct  10680
gttatcccag atgacattac cctgttatcc ctagatacat taccctgtta tcccagatga  10740
cataccctgt tatccctaga tgacattacc ctgttatccc agatgacatt accctgttat  10800
ccctagatac attaccctgt tatcccagat gacataccct gttatcccta gatgacatta  10860
ccctgttatc ccagatgaca ttaccctgtt atccctagat acattaccct gttatcccag  10920
atgacatacc ctgttatccc tagatgacat taccctgtta tcccagatga cattaccctg  10980
ttatccctag atacattacc ctgttatccc agatgacata ccctgttatc cctagatgac  11040
attaccctgt tatcccagat aaactcaatg atgatgatga tgatggtcga gactcagcgg  11100
ccgcggtgcc agggcgtgcc cttgggctcc ccgggcgcga ctagtgaatt cagatctttt  11160
ggcttatgtc tgtggttttc tgcacaatac agtacgctgg cactattgca aactttaatc  11220
ttttgggcac tgctcctaca tattttgaac aattggcgcg cctctttggc gcatataagg  11280
cgcacctggt attagtcatt ttcctgtcca ggtgcgctac aacaattgct tgcataacta  11340
tatccactcc ctaagtaata aaactgcttt taggcacata ttttagtttg tttttactta  11400
agctaattgc atacttggct tgtacaacta ctttcatgtc caacattctg tctaccctta  11460
acatgaacta taatatgact aagctgtgca tacatagttt atgcaaccga aataggttgg  11520
gcagcacata ctatactttt c                                            11541
```

<210> SEQ ID NO 11

<211> LENGTH: 72
<212> TYPE: DNA
<213> ORGANISM: artificial sequence
<220> FEATURE:
<223> OTHER INFORMATION: chemically synthetised
<220> FEATURE:
<221> NAME/KEY: misc_feature
<222> LOCATION: (1)..(72)
<223> OTHER INFORMATION: C-terminal sequence of FMDV 2A

<400> SEQUENCE: 11
gcaccggtga aacagacttt gaattttgac cttctcaagt tggcgggaga cgtggagtcc 60
aaccctgggc cc 72

<210> SEQ ID NO 12
<211> LENGTH: 1974
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1975)
<223> OTHER INFORMATION: HPV18 E1 ORF

<400> SEQUENCE: 12
atggctgatc cagaaggtac agacggggag ggcacgggtt gtaacggctg gttttatgta 60
caagctattg tagacaaaaa aacaggagat gtaatatcag atgacgagga cgaaaatgca 120
acagacacag ggtcggatat ggtagatttt attgatacac aaggaacatt ttgtgaacag 180
gcagagctag agacagcaca ggcattgttc catgcgcagg aggtccacaa tgatgcacaa 240
gtgttgcatg ttttaaaacg aaagtttgca ggaggcagca cagaaaacag tccattaggg 300
gagcggctgg aggtggatac agagttaagt ccacggttac aagaaatatc tttaaatagt 360
gggcagaaaa aggcaaaaag gcggctgttt acaatatcag atagtggcta tggctgttct 420
gaagtggaag caacacagat tcaggtaact acaaatggcg aacatggcgg caatgtatgt 480
agtggcggca gtacggaggc tatagacaac gggggcacag agggcaacaa cagcagtgta 540
gacggtacaa gtgacaatag caatatagaa aatgtaaatc cacaatgtac catagcacaa 600
ttaaaagact tgttaaaagt aaacaataaa caaggagcta tgttagcagt atttaaagac 660
acatatgggc tatcatttac agatttagtt agaaatttta aaagtgataa aaccacgtgt 720
acagattggg ttacagctat atttggagta aacccaacaa tagcagaagg atttaaaaca 780
ctaatacagc catttatatt atatgcccat attcaatgtc tagactgtaa atggggagta 840
ttaatattag ccctgttgcg ttacaaatgt ggtaagagta gactaacagt tgctaaaggt 900
ttaagtacgt tgttacacgt acctgaaact tgtatgttaa ttcaaccacc aaaattgcga 960
agtagtgttg cagcactata ttggtataga acaggaatat caaatattag tgaagtaatg 1020
ggagacacac ctgagtggat acaaagactt actattatac aacatggaat agatgatagc 1080
aattttgatt tgtcagaaat ggtacaatgg gcatttgata atgagctgac agatgaaagc 1140
gatatggcat ttgaatatgc cttattagca gacagcaaca gcaatgcagc tgccttttta 1200
aaaagcaatt gccaagctaa atatttaaaa gattgtgcca caatgtgcaa acattatagg 1260
cgagcccaaa aacgacaaat gaatatgtca cagtggatac gatttagatg ttcaaaaata 1320
gatgaagggg gagattggag accaatagtg caattcctgc gataccaaca aatagagttt 1380
ataacatttt taggagcctt aaaatcattt ttaaaaggaa cccccaaaaa aaattgttta 1440
gtattttgtg gaccagcaaa tacaggaaaa tcatattttg gaatgagttt tatacacttt 1500
atacaaggag cagtaatatc atttgtgaat tccactagtc atttttggtt ggaaccgtta 1560
acagatacta aggtggccat gttagatgat gcaacgacca cgtgttggac atactttgat 1620
acctatatga gaaatgcgtt agatggcaat ccaataagta ttgatagaaa gcacaaacca 1680
ttaatacaac taaaatgtcc tccaatacta ctaaccacaa atatacatcc agcaaaggat 1740
aatagatggc catatttaga aagtagaata acagtatttg aatttccaaa tgcatttcca 1800
tttgataaaa atggcaatcc agtatatgaa ataaatgaca aaaattggaa atgttttttt 1860
gaaaggacat ggtccagatt agatttgcac gaggaagagg aagatgcaga caccgaagga 1920
aaccctttcg gaacgtttaa gttgcgtgca ggacaaaatc atagaccact atga 1974

<210> SEQ ID NO 13
<211> LENGTH: 1821
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1821)
<223> OTHER INFORMATION: HPV 5 E1 ORF

<400> SEQUENCE: 13
atgacggatc ctaattctaa aggtagtaca tctaaagaag ggtttggtga ttggtgttta 60
ttggaagctg actgtagtga tgtagaaaat gatttgggac aattatttga gagagataca 120
gactctgata tatcggattt gttagatgat actgaactgg agcagggcaa ttctttggaa 180
ctatttcatc aacaggagtg tgagcagagc gaggagcaat tacaaaaact aaaacgaaag 240
tatcttagtc caaaagctgt cgcacagctt agtccgcgac ttgagtcaat ttcattgtca 300
cctcagcaga agtctaagcg aaggcttttt gcagagcagg acagcggact cgagctgact 360
ttaaacaatg aagctgaaga tgttactcct gaggtggagg taccggctat tgactctcgg 420
ccggatgacg agggaggttc aggggacgta gatatacatt ttactgcatt gttgcgttct 480
agcaacaaaa aagctacatt aatggctaag tttaaagagt catttggagt aggttttaat 540
gaattgacac ggcaattcaa aagccacaaa acctgctgta aagactgggt tgtctctgta 600
tatgcagtgc atgatgattt atttgaaagc tcaaagcagc tgttgcaaca gcattgtgac 660
tatatctggg tccgtgggat aggtgcaatg tcattatatc tattgtgttt caaggcggga 720
aaaaatcgcg ggacagttca taagttaatt acctcaatgt taaatgtgca tgaacagcaa 780
atattgtctg agccgccaaa attgagaaac acagccgctg cattgttctg gtataagggt 840
tgtatgggat cgggggcgtt tagccatgga ccatatcctg attggattgc ccaacaaact 900
atattaggtc acaaaagtgc tgaggcaagt acttttgatt tttcagcaat ggtacaatgg 960
gcgtttgata atcatttatt agacgaagca gatatagcat accagtatgc aaggcttgca 1020
cccgaagatg cgaatgcagt agcttggctt gcacataaca accaggccaa atttgtgaga 1080
gaatgtgctt atatggtacg attctataag aagggacaaa tgagagacat gagcatatct 1140
gaatggatat acactaaaat caatgaagta gaaggggaag ggcactggtc agatatagta 1200
aagtttatta gataccaaaa tataaacttt attgtatttc taactgcatt aaaagaattc 1260
ctacactcag tgccaaaaaa aaattgtatt ttaatttatg gtcctccaaa ttctggaaag 1320
tcatcatttg caatgtcttt aataagagtg ttgaagggta gggtgttgtc atttgtgaac 1380
tctaaaagtc agttttggct gcaacccctt tcagagtgca agatagctct attggatgat 1440

-continued gtaacagacc cttgttggat atacatggat acatatttaa gaaatggctt ggatggacat 1500
tatgtttcat tagattgtaa atatagagcc ccaacgcaaa tgaaatttcc cccattatta 1560
ttaacatcta acatcaatgt gcatggggaa actaattata gatatttaca cagtagaata 1620
aaaggatttg aatttccaaa tccttttcct atgaaagcag ataatacacc tcagtttgaa 1680
ctaactgacc aaagctggaa atcttttttt acaaggcttt ggacacaatt agacctgagt 1740
gatcaagaag aggagggcga ggatggagaa tctcagcgag cgtttcaatg ctctgcaaga 1800
tcagctaatg aacatttatg a 1821

<210> SEQ ID NO 14
<211> LENGTH: 1098
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1098)
<223> OTHER INFORMATION: HPV18 E2 ORF

<400> SEQUENCE: 14
atgcagacac cgaaggaaac cctttcggaa cgtttaagtg cgttgcagga caaaatcata 60
gaccactatg aaaatgacag taaagacata gacagccaaa tacagtattg gcaactaata 120
cgttgggaaa atgcaatatt ctttgcagca agggaacatg gcatacagac attaaaccac 180
caggtggtgc cagcctataa catttcaaaa agtaaagcac ataaagctat tgaactgcaa 240
atggccctac aaggccttgc acaaagtgca tacaaaaccg aggattggac actgcaagac 300
acatgcgagg aactatggaa tacagaacct actcactgct ttaaaaaagg tggccaaaca 360
gtacaagtat attttgatgg caacaaagac aattgtatga cctatgtagc atgggacagt 420
gtgtattata tgactgatgc aggaacatgg gacaaaacgg ctacctgtgt aagtcacagg 480
ggattgtatt atgtaaagga agggtacaac acgttttata tagaatttaa aagtgaatgt 540
gaaaaatatg ggaacacagg tacgtgggaa gtacattttg ggaataatgt aattgattgt 600
aatgactcta tgtgcagtac cagtgacgac acggtatccg ctactcagct tgttaaacag 660
ctacagcaca ccccctcacc gtattccagc accgtgtccg tgggcaccgc aaagacctac 720
ggccagacgt cggctgctac acgacctgga cactgtggac tcgcggagaa gcagcattgt 780
ggacctgtca acccacttct cggtgcagct acacctacag gcaacaacaa aagacggaaa 840
ctctgtagtg gtaacactac gcctataata catttaaaag gtgacagaaa cagtttaaaa 900
tgtttacggt acagattgcg aaaacatagc gaccactata gagatatatc atccacctgg 960
cattggacag gtgcaggcaa tgaaaaaaca ggaatactga ctgtaacata ccatagtgaa 1020
acacaaagaa caaaattttt aaatactgtt gcaattccag atagtgtaca aatattggtg 1080
ggatacatga caatgtaa 1098

<210> SEQ ID NO 15
<211> LENGTH: 1545
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1545)
<223> OTHER INFORMATION: HPV5 E2 ORF

<400> SEQUENCE: 15

```
atggagaatc tcagcgagcg tttcaatgct ctgcaagatc agctaatgaa catttatgaa     60

gctgcagaac aaacattgca ggcacaaatt aaacattggc aaaccttacg aaaagaagct    120

gtattactct actatgctag ggagaaaggt gttacaaggc ttggatatca acctgtgcct    180

gtaaaggcag tatcagaaac aaaggctaaa gaagccatag caatggtgct gcagcttgag    240

tcactacaga cgtctgattt tgctcatgag ccatggactc tagttgatac cagcatagaa    300

acatttagaa gcgctccaga aggtcacttc aaaaaaggcc ccgtccctgt agaagttatt    360

tatgacaatg atccagataa tgccaatttg tatacaatgt ggacctatgt gtattatatg    420

gatgcggatg ataagtggca taaggcaaga agtggggtga atcacattgg catttattat    480

ttacaaggaa cgtttaaaaa ctattatgta ctgtttgctg acgatgcaaa aagatatggt    540

acaactggag aatgggaagt aaaagttaat aaggaaactg tgtttgctcc tgtcaccagc    600

tccacgcctc cagggtcgcc aggaggacaa gcagacacaa acaccacctc cgcgaccccc    660

accacctcca caaccgccgt tgactccacg tccagacagc tcactacatc aaaacagcca    720

caacaaaccg aaaccagagg aagaaggtac ggacggaggg cctccagcaa gtcaaggaga    780

tcgcaaacgc agcaaaggcg atcaaggtcc cgacaccggt cccggtctcg gtcccggtcg    840

cggtccaagt ccaaaaccca caccactcgg tccaccacca ggtcccggtc cacgtcgctc    900

accaagactc gggcccttac aagcagatcg cgatccagag gaaggtcccc aaccacctgc    960

agaaggggag gtggaaggtc acccaggcgg cgatcaaggt caccctccac ctcctcctcc   1020

tgcaccacac aacggtcaca gcgggcacgg gccgaaagtt caacaaccag aggggcccga   1080

gggtcgagag ggtcacgagg agggagccgt ggggggagag ggcggcgacg aggaaggtca   1140

tcctcctcct cctcccccac ccacaaacgg tcacgagggg aatctgctaa gctccgtggc   1200

gtctctcctg gtgaagtggg agggtcactt cgatcagtta gttcaaagca tacaggtcga   1260

cttggaagat tactggaaga agctcgcgac cccccagtaa tcattgtcaa aggggcggct   1320

aacacactga aatgcttccg caacagagct aaaattacat acaagggact gtttaggtca   1380

tttagcacta cctggtcatg ggtggcagga gatggcactg agcgtctagg caggcccaga   1440

atgctcatta gcttttcttc atatactcaa aggagagatt ttgatgaagc ggtacgatac   1500

cctaaaggag ttgataaggc ctatggcaac ctggacagtc tttaa                   1545
```

<210> SEQ ID NO 16
<211> LENGTH: 724
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(724)
<223> OTHER INFORMATION: HPV 18 RLuc -E2 fusion protein

<400> SEQUENCE: 16

```
Met Gln Thr Pro Lys Glu Thr Leu Ser Glu Arg Leu Ser Cys Val Gln
1               5                   10                  15

Asp Lys Ile Ile Asp His Tyr Glu Ala Thr Ser Lys Val Tyr Asp Pro
            20                  25                  30

Glu Gln Arg Lys Arg Met Ile Thr Gly Pro Gln Trp Trp Ala Arg Cys
        35                  40                  45

Lys Gln Met Asn Val Leu Asp Ser Phe Ile Asn Tyr Tyr Asp Ser Glu
    50                  55                  60
```

-continued

```
Lys His Ala Glu Asn Ala Val Ile Phe Leu His Gly Asn Ala Ala Ser
65                  70                  75                  80

Ser Tyr Leu Trp Arg His Val Val Pro His Ile Glu Pro Val Ala Arg
                85                  90                  95

Cys Ile Ile Pro Asp Leu Ile Gly Met Gly Lys Ser Gly Lys Ser Gly
            100                 105                 110

Asn Gly Ser Tyr Arg Leu Leu Asp His Tyr Lys Tyr Leu Thr Ala Trp
        115                 120                 125

Phe Glu Leu Leu Asn Leu Pro Lys Lys Ile Ile Phe Val Gly His Asp
    130                 135                 140

Trp Gly Ala Cys Leu Ala Phe His Tyr Ser Tyr Glu His Gln Asp Lys
145                 150                 155                 160

Ile Lys Ala Ile Val His Ala Glu Ser Val Val Asp Val Ile Glu Ser
                165                 170                 175

Trp Asp Glu Trp Pro Asp Ile Glu Glu Asp Ile Ala Leu Ile Lys Ser
            180                 185                 190

Glu Glu Gly Glu Lys Met Val Leu Glu Asn Asn Phe Phe Val Glu Thr
        195                 200                 205

Met Leu Pro Ser Lys Ile Met Arg Lys Leu Glu Pro Glu Glu Phe Ala
    210                 215                 220

Ala Tyr Leu Glu Pro Phe Lys Glu Lys Gly Glu Val Arg Arg Pro Thr
225                 230                 235                 240

Leu Ser Trp Pro Arg Glu Ile Pro Leu Val Lys Gly Gly Lys Pro Asp
                245                 250                 255

Val Val Gln Ile Val Arg Asn Tyr Asn Ala Tyr Leu Arg Ala Ser Asp
            260                 265                 270

Asp Leu Pro Lys Met Phe Ile Glu Ser Asp Pro Gly Phe Phe Ser Asn
        275                 280                 285

Ala Ile Val Glu Gly Ala Lys Lys Phe Pro Asn Thr Glu Phe Val Lys
    290                 295                 300

Val Lys Gly Leu His Phe Ser Gln Glu Asp Ala Pro Asp Glu Met Gly
305                 310                 315                 320

Lys Tyr Ile Lys Ser Phe Val Glu Arg Val Leu Lys Asn Glu Gln Ala
                325                 330                 335

Pro Val Lys Gln Thr Leu Asn Phe Asp Leu Leu Lys Leu Ala Gly Asp
            340                 345                 350

Val Glu Ser Asn Pro Gly Pro Met Gln Thr Pro Lys Glu Thr Leu Ser
        355                 360                 365

Glu Arg Leu Ser Ala Leu Gln Asp Lys Ile Ile Asp His Tyr Glu Asn
    370                 375                 380

Asp Ser Lys Asp Ile Asp Ser Gln Ile Gln Tyr Trp Gln Leu Ile Arg
385                 390                 395                 400

Trp Glu Asn Ala Ile Phe Phe Ala Ala Arg Glu His Gly Ile Gln Thr
                405                 410                 415

Leu Asn His Gln Val Val Pro Ala Tyr Asn Ile Ser Lys Ser Lys Ala
            420                 425                 430

His Lys Ala Ile Glu Leu Gln Met Ala Leu Gln Gly Leu Ala Gln Ser
        435                 440                 445

Ala Tyr Lys Thr Glu Asp Trp Thr Leu Gln Asp Thr Cys Glu Glu Leu
    450                 455                 460

Trp Asn Thr Glu Pro Thr His Cys Phe Lys Lys Gly Gly Gln Thr Val
465                 470                 475                 480

Gln Val Tyr Phe Asp Gly Asn Lys Asp Asn Cys Met Thr Tyr Val Ala
```

485 490 495

Trp Asp Ser Val Tyr Tyr Met Thr Asp Ala Gly Thr Trp Asp Lys Thr
500 505 510

Ala Thr Cys Val Ser His Arg Gly Leu Tyr Tyr Val Lys Glu Gly Tyr
515 520 525

Asn Thr Phe Tyr Ile Glu Phe Lys Ser Glu Cys Glu Lys Tyr Gly Asn
530 535 540

Thr Gly Thr Trp Glu Val His Phe Gly Asn Asn Val Ile Asp Cys Asn
545 550 555 560

Asp Ser Met Cys Ser Thr Ser Asp Asp Thr Val Ser Ala Thr Gln Leu
565 570 575

Val Lys Gln Leu Gln His Thr Pro Ser Pro Tyr Ser Ser Thr Val Ser
580 585 590

Val Gly Thr Ala Lys Thr Tyr Gly Gln Thr Ser Ala Ala Thr Arg Pro
595 600 605

Gly His Cys Gly Leu Ala Glu Lys Gln His Cys Gly Pro Val Asn Pro
610 615 620

Leu Leu Gly Ala Ala Thr Pro Thr Gly Asn Asn Lys Arg Arg Lys Leu
625 630 635 640

Cys Ser Gly Asn Thr Thr Pro Ile Ile His Leu Lys Gly Asp Arg Asn
645 650 655

Ser Leu Lys Cys Leu Arg Tyr Arg Leu Arg Lys His Ser Asp His Tyr
660 665 670

Arg Asp Ile Ser Ser Thr Trp His Trp Thr Gly Ala Gly Asn Glu Lys
675 680 685

Thr Gly Ile Leu Thr Val Thr Tyr His Ser Glu Thr Gln Arg Thr Lys
690 695 700

Phe Leu Asn Thr Val Ala Ile Pro Asp Ser Val Gln Ile Leu Val Gly
705 710 715 720

Tyr Met Thr Met

<210> SEQ ID NO 17
<211> LENGTH: 869
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(869)
<223> OTHER INFORMATION: HPV 5 RLuc-E2 fusion protein

<400> SEQUENCE: 17

Met Glu Asn Leu Ser Glu Arg Phe Asn Ala Leu Gln Asp Gln Leu Met
1 5 10 15

Asn Ile Tyr Glu Ala Thr Ser Lys Val Tyr Asp Pro Glu Gln Arg Lys
20 25 30

Arg Met Ile Thr Gly Pro Gln Trp Trp Ala Arg Cys Lys Gln Met Asn
35 40 45

Val Leu Asp Ser Phe Ile Asn Tyr Tyr Asp Ser Glu Lys His Ala Glu
50 55 60

Asn Ala Val Ile Phe Leu His Gly Asn Ala Ala Ser Ser Tyr Leu Trp
65 70 75 80

Arg His Val Val Pro His Ile Glu Pro Val Ala Arg Cys Ile Ile Pro
85 90 95

Asp Leu Ile Gly Met Gly Lys Ser Gly Lys Ser Gly Asn Gly Ser Tyr

```
            100                 105                 110

Arg Leu Leu Asp His Tyr Lys Tyr Leu Thr Ala Trp Phe Glu Leu Leu
        115                 120                 125

Asn Leu Pro Lys Lys Ile Ile Phe Val Gly His Asp Trp Gly Ala Cys
    130                 135                 140

Leu Ala Phe His Tyr Ser Tyr Glu His Gln Asp Lys Ile Lys Ala Ile
145                 150                 155                 160

Val His Ala Glu Ser Val Val Asp Val Ile Glu Ser Trp Asp Glu Trp
                165                 170                 175

Pro Asp Ile Glu Glu Asp Ile Ala Leu Ile Lys Ser Glu Glu Gly Glu
            180                 185                 190

Lys Met Val Leu Glu Asn Asn Phe Phe Val Glu Thr Met Leu Pro Ser
        195                 200                 205

Lys Ile Met Arg Lys Leu Glu Pro Glu Glu Phe Ala Ala Tyr Leu Glu
    210                 215                 220

Pro Phe Lys Glu Lys Gly Glu Val Arg Arg Pro Thr Leu Ser Trp Pro
225                 230                 235                 240

Arg Glu Ile Pro Leu Val Lys Gly Gly Lys Pro Asp Val Val Gln Ile
                245                 250                 255

Val Arg Asn Tyr Asn Ala Tyr Leu Arg Ala Ser Asp Asp Leu Pro Lys
            260                 265                 270

Met Phe Ile Glu Ser Asp Pro Gly Phe Phe Ser Asn Ala Ile Val Glu
        275                 280                 285

Gly Ala Lys Lys Phe Pro Asn Thr Glu Phe Val Lys Val Lys Gly Leu
    290                 295                 300

His Phe Ser Gln Glu Asp Ala Pro Asp Glu Met Gly Lys Tyr Ile Lys
305                 310                 315                 320

Ser Phe Val Glu Arg Val Leu Lys Asn Glu Gln Ala Pro Val Lys Gln
                325                 330                 335

Thr Leu Asn Phe Asp Leu Leu Lys Leu Ala Gly Asp Val Glu Ser Asn
            340                 345                 350

Pro Gly Pro Met Glu Asn Leu Ser Glu Arg Phe Asn Ala Leu Gln Asp
        355                 360                 365

Gln Leu Met Asn Ile Tyr Glu Ala Ala Glu Gln Thr Leu Gln Ala Gln
    370                 375                 380

Ile Lys His Trp Gln Thr Leu Arg Lys Glu Ala Val Leu Leu Tyr Tyr
385                 390                 395                 400

Ala Arg Glu Lys Gly Val Thr Arg Leu Gly Tyr Gln Pro Val Pro Val
                405                 410                 415

Lys Ala Val Ser Glu Thr Lys Ala Lys Glu Ala Ile Ala Met Val Leu
            420                 425                 430

Gln Leu Glu Ser Leu Gln Thr Ser Asp Phe Ala His Glu Pro Trp Thr
        435                 440                 445

Leu Val Asp Thr Ser Ile Glu Thr Phe Arg Ser Ala Pro Glu Gly His
    450                 455                 460

Phe Lys Lys Gly Pro Val Pro Val Glu Val Ile Tyr Asp Asn Asp Pro
465                 470                 475                 480

Asp Asn Ala Asn Leu Tyr Thr Met Trp Thr Tyr Val Tyr Tyr Met Asp
                485                 490                 495

Ala Asp Asp Lys Trp His Lys Ala Arg Ser Gly Val Asn His Ile Gly
            500                 505                 510

Ile Tyr Tyr Leu Gln Gly Thr Phe Lys Asn Tyr Tyr Val Leu Phe Ala
        515                 520                 525
```

```
Asp Asp Ala Lys Arg Tyr Gly Thr Thr Gly Glu Trp Glu Val Lys Val
    530                 535                 540

Asn Lys Glu Thr Val Phe Ala Pro Val Thr Ser Ser Thr Pro Pro Gly
545                 550                 555                 560

Ser Pro Gly Gly Gln Ala Asp Thr Asn Thr Thr Ser Ala Thr Pro Thr
                565                 570                 575

Thr Ser Thr Thr Ala Val Asp Ser Thr Ser Arg Gln Leu Thr Thr Ser
            580                 585                 590

Lys Gln Pro Gln Gln Thr Glu Thr Arg Gly Arg Arg Tyr Gly Arg Arg
        595                 600                 605

Ala Ser Ser Lys Ser Arg Arg Ser Gln Thr Gln Gln Arg Arg Ser Arg
    610                 615                 620

Ser Arg His Arg Ser Arg Ser Arg Ser Arg Ser Arg Ser Lys Ser Lys
625                 630                 635                 640

Thr His Thr Thr Arg Ser Thr Thr Arg Ser Arg Ser Thr Ser Leu Thr
                645                 650                 655

Lys Thr Arg Ala Leu Thr Ser Arg Ser Arg Ser Arg Gly Arg Ser Pro
            660                 665                 670

Thr Thr Cys Arg Arg Gly Gly Gly Arg Ser Pro Arg Arg Arg Ser Arg
        675                 680                 685

Ser Pro Ser Thr Ser Ser Ser Cys Thr Thr Gln Arg Ser Gln Arg Ala
    690                 695                 700

Arg Ala Glu Ser Ser Thr Thr Arg Gly Ala Arg Gly Ser Arg Gly Ser
705                 710                 715                 720

Arg Gly Gly Ser Arg Gly Gly Arg Gly Arg Arg Arg Gly Arg Ser Ser
                725                 730                 735

Ser Ser Ser Ser Pro Thr His Lys Arg Ser Arg Gly Glu Ser Ala Lys
            740                 745                 750

Leu Arg Gly Val Ser Pro Gly Glu Val Gly Gly Ser Leu Arg Ser Val
        755                 760                 765

Ser Ser Lys His Thr Gly Arg Leu Gly Arg Leu Leu Glu Glu Ala Arg
    770                 775                 780

Asp Pro Pro Val Ile Ile Val Lys Gly Ala Ala Asn Thr Leu Lys Cys
785                 790                 795                 800

Phe Arg Asn Arg Ala Lys Ile Thr Tyr Lys Gly Leu Phe Arg Ser Phe
                805                 810                 815

Ser Thr Thr Trp Ser Trp Val Ala Gly Asp Gly Thr Glu Arg Leu Gly
            820                 825                 830

Arg Pro Arg Met Leu Ile Ser Phe Ser Ser Tyr Thr Gln Arg Arg Asp
        835                 840                 845

Phe Asp Glu Ala Val Arg Tyr Pro Lys Gly Val Asp Lys Ala Tyr Gly
    850                 855                 860

Asn Leu Asp Ser Leu
865
```

<210> SEQ ID NO 18
<211> LENGTH: 24
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(24)
<223> OTHER INFORMATION: 24 N-terminal amino acids of HPV18 E2 encoded by part of E2 ORF that is overlapped with E1 ORF

<400> SEQUENCE: 18

Met Gln Thr Pro Lys Glu Thr Leu Ser Glu Arg Leu Ser Cys Val Gln
1               5                   10                  15

Asp Lys Ile Ile Asp His Tyr Glu
            20

<210> SEQ ID NO 19
<211> LENGTH: 310
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(310)
<223> OTHER INFORMATION: Rluc protein starting from the second amino
      acid

<400> SEQUENCE: 19

Thr Ser Lys Val Tyr Asp Pro Glu Gln Arg Lys Arg Met Ile Thr Gly
1               5                   10                  15

Pro Gln Trp Trp Ala Arg Cys Lys Gln Met Asn Val Leu Asp Ser Phe
            20                  25                  30

Ile Asn Tyr Tyr Asp Ser Glu Lys His Ala Glu Asn Ala Val Ile Phe
        35                  40                  45

Leu His Gly Asn Ala Ala Ser Ser Tyr Leu Trp Arg His Val Val Pro
    50                  55                  60

His Ile Glu Pro Val Ala Arg Cys Ile Ile Pro Asp Leu Ile Gly Met
65                  70                  75                  80

Gly Lys Ser Gly Lys Ser Gly Asn Gly Ser Tyr Arg Leu Leu Asp His
                85                  90                  95

Tyr Lys Tyr Leu Thr Ala Trp Phe Glu Leu Leu Asn Leu Pro Lys Lys
            100                 105                 110

Ile Ile Phe Val Gly His Asp Trp Gly Ala Cys Leu Ala Phe His Tyr
        115                 120                 125

Ser Tyr Glu His Gln Asp Lys Ile Lys Ala Ile Val His Ala Glu Ser
    130                 135                 140

Val Val Asp Val Ile Glu Ser Trp Asp Glu Trp Pro Asp Ile Glu Glu
145                 150                 155                 160

Asp Ile Ala Leu Ile Lys Ser Glu Glu Gly Glu Lys Met Val Leu Glu
                165                 170                 175

Asn Asn Phe Phe Val Glu Thr Met Leu Pro Ser Lys Ile Met Arg Lys
            180                 185                 190

Leu Glu Pro Glu Glu Phe Ala Ala Tyr Leu Glu Pro Phe Lys Glu Lys
        195                 200                 205

Gly Glu Val Arg Arg Pro Thr Leu Ser Trp Pro Arg Glu Ile Pro Leu
    210                 215                 220

Val Lys Gly Gly Lys Pro Asp Val Val Gln Ile Val Arg Asn Tyr Asn
225                 230                 235                 240

Ala Tyr Leu Arg Ala Ser Asp Asp Leu Pro Lys Met Phe Ile Glu Ser
                245                 250                 255

Asp Pro Gly Phe Phe Ser Asn Ala Ile Val Glu Gly Ala Lys Lys Phe
            260                 265                 270

Pro Asn Thr Glu Phe Val Lys Val Lys Gly Leu His Phe Ser Gln Glu
        275                 280                 285

Asp Ala Pro Asp Glu Met Gly Lys Tyr Ile Lys Ser Phe Val Glu Arg

```
    290                 295                 300

Val Leu Lys Asn Glu Gln
305                 310


<210> SEQ ID NO 20
<211> LENGTH: 24
<212> TYPE: PRT
<213> ORGANISM: artificial sequence
<220> FEATURE:
<223> OTHER INFORMATION: chemcially synthesized
<220> FEATURE:
<221> NAME/KEY: PEPTIDE
<222> LOCATION: (1)..(24)
<223> OTHER INFORMATION: FMDV 2A peptide

<400> SEQUENCE: 20

Ala Pro Val Lys Gln Thr Leu Asn Phe Asp Leu Leu Lys Leu Ala Gly
1               5                   10                  15

Asp Val Glu Ser Asn Pro Gly Pro
            20


<210> SEQ ID NO 21
<211> LENGTH: 365
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(365)
<223> OTHER INFORMATION: Full-length HPV18 E2 protein starting from
      initiating methionine

<400> SEQUENCE: 21

Met Gln Thr Pro Lys Glu Thr Leu Ser Glu Arg Leu Ser Ala Leu Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Ala Tyr Lys Thr Glu Asp Trp
                85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
        115                 120                 125

Lys Asp Asn Cys Met Thr Tyr Val Ala Trp Asp Ser Val Tyr Tyr Met
    130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
        195                 200                 205
```

```
Asp Asp Thr Val Ser Ala Thr Gln Leu Val Lys Gln Leu Gln His Thr
    210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
            260                 265                 270

Thr Gly Asn Asn Lys Arg Arg Lys Leu Cys Ser Gly Asn Thr Thr Pro
        275                 280                 285

Ile Ile His Leu Lys Gly Asp Arg Asn Ser Leu Lys Cys Leu Arg Tyr
    290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
                325                 330                 335

Tyr His Ser Glu Thr Gln Arg Thr Lys Phe Leu Asn Thr Val Ala Ile
            340                 345                 350

Pro Asp Ser Val Gln Ile Leu Val Gly Tyr Met Thr Met
        355                 360                 365


<210> SEQ ID NO 22
<211> LENGTH: 358
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(358)
<223> OTHER INFORMATION: Rluc protein fused with 24 N-terminal aa of
      HPV18 E2 + Ala at its N-teminus and with  FMDV 2A peptide at its
      C-terminus

<400> SEQUENCE: 22

Met Gln Thr Pro Lys Glu Thr Leu Ser Glu Arg Leu Ser Cys Val Gln
1               5                   10                  15

Asp Lys Ile Ile Asp His Tyr Glu Ala Thr Ser Lys Val Tyr Asp Pro
            20                  25                  30

Glu Gln Arg Lys Arg Met Ile Thr Gly Pro Gln Trp Trp Ala Arg Cys
        35                  40                  45

Lys Gln Met Asn Val Leu Asp Ser Phe Ile Asn Tyr Tyr Asp Ser Glu
    50                  55                  60

Lys His Ala Glu Asn Ala Val Ile Phe Leu His Gly Asn Ala Ala Ser
65                  70                  75                  80

Ser Tyr Leu Trp Arg His Val Val Pro His Ile Glu Pro Val Ala Arg
                85                  90                  95

Cys Ile Ile Pro Asp Leu Ile Gly Met Gly Lys Ser Gly Lys Ser Gly
            100                 105                 110

Asn Gly Ser Tyr Arg Leu Leu Asp His Tyr Lys Tyr Leu Thr Ala Trp
        115                 120                 125

Phe Glu Leu Leu Asn Leu Pro Lys Lys Ile Ile Phe Val Gly His Asp
    130                 135                 140

Trp Gly Ala Cys Leu Ala Phe His Tyr Ser Tyr Glu His Gln Asp Lys
145                 150                 155                 160

Ile Lys Ala Ile Val His Ala Glu Ser Val Val Asp Val Ile Glu Ser
                165                 170                 175
```

```
Trp Asp Glu Trp Pro Asp Ile Glu Glu Asp Ile Ala Leu Ile Lys Ser
            180                 185                 190

Glu Glu Gly Glu Lys Met Val Leu Glu Asn Asn Phe Phe Val Glu Thr
        195                 200                 205

Met Leu Pro Ser Lys Ile Met Arg Lys Leu Glu Pro Glu Glu Phe Ala
    210                 215                 220

Ala Tyr Leu Glu Pro Phe Lys Glu Lys Gly Glu Val Arg Arg Pro Thr
225                 230                 235                 240

Leu Ser Trp Pro Arg Glu Ile Pro Leu Val Lys Gly Gly Lys Pro Asp
                245                 250                 255

Val Val Gln Ile Val Arg Asn Tyr Asn Ala Tyr Leu Arg Ala Ser Asp
            260                 265                 270

Asp Leu Pro Lys Met Phe Ile Glu Ser Asp Pro Gly Phe Phe Ser Asn
        275                 280                 285

Ala Ile Val Glu Gly Ala Lys Lys Phe Pro Asn Thr Glu Phe Val Lys
    290                 295                 300

Val Lys Gly Leu His Phe Ser Gln Glu Asp Ala Pro Asp Glu Met Gly
305                 310                 315                 320

Lys Tyr Ile Lys Ser Phe Val Glu Arg Val Leu Lys Asn Glu Gln Ala
                325                 330                 335

Pro Val Lys Gln Thr Leu Asn Phe Asp Leu Leu Lys Leu Ala Gly Asp
            340                 345                 350

Val Glu Ser Asn Pro Gly
        355
```

```
<210> SEQ ID NO 23
<211> LENGTH: 366
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(366)
<223> OTHER INFORMATION: full-length HPV18 E2 protein containing
      additional Pro at N-terminal end

<400> SEQUENCE: 23

Pro Met Gln Thr Pro Lys Glu Thr Leu Ser Glu Arg Leu Ser Ala Leu
1               5                   10                  15

Gln Asp Lys Ile Ile Asp His Tyr Glu Asn Asp Ser Lys Asp Ile Asp
            20                  25                  30

Ser Gln Ile Gln Tyr Trp Gln Leu Ile Arg Trp Glu Asn Ala Ile Phe
        35                  40                  45

Phe Ala Ala Arg Glu His Gly Ile Gln Thr Leu Asn His Gln Val Val
    50                  55                  60

Pro Ala Tyr Asn Ile Ser Lys Ser Lys Ala His Lys Ala Ile Glu Leu
65                  70                  75                  80

Gln Met Ala Leu Gln Gly Leu Ala Gln Ser Ala Tyr Lys Thr Glu Asp
                85                  90                  95

Trp Thr Leu Gln Asp Thr Cys Glu Glu Leu Trp Asn Thr Glu Pro Thr
            100                 105                 110

His Cys Phe Lys Lys Gly Gly Gln Thr Val Gln Val Tyr Phe Asp Gly
        115                 120                 125

Asn Lys Asp Asn Cys Met Thr Tyr Val Ala Trp Asp Ser Val Tyr Tyr
    130                 135                 140

Met Thr Asp Ala Gly Thr Trp Asp Lys Thr Ala Thr Cys Val Ser His
```

```
145                 150                 155                 160

Arg Gly Leu Tyr Tyr Val Lys Glu Gly Tyr Asn Thr Phe Tyr Ile Glu
                165                 170                 175

Phe Lys Ser Glu Cys Glu Lys Tyr Gly Asn Thr Gly Thr Trp Glu Val
            180                 185                 190

His Phe Gly Asn Asn Val Ile Asp Cys Asn Asp Ser Met Cys Ser Thr
        195                 200                 205

Ser Asp Asp Thr Val Ser Ala Thr Gln Leu Val Lys Gln Leu Gln His
    210                 215                 220

Thr Pro Ser Pro Tyr Ser Ser Thr Val Ser Val Gly Thr Ala Lys Thr
225                 230                 235                 240

Tyr Gly Gln Thr Ser Ala Ala Thr Arg Pro Gly His Cys Gly Leu Ala
                245                 250                 255

Glu Lys Gln His Cys Gly Pro Val Asn Pro Leu Leu Gly Ala Ala Thr
            260                 265                 270

Pro Thr Gly Asn Asn Lys Arg Arg Lys Leu Cys Ser Gly Asn Thr Thr
        275                 280                 285

Pro Ile Ile His Leu Lys Gly Asp Arg Asn Ser Leu Lys Cys Leu Arg
    290                 295                 300

Tyr Arg Leu Arg Lys His Ser Asp His Tyr Arg Asp Ile Ser Ser Thr
305                 310                 315                 320

Trp His Trp Thr Gly Ala Gly Asn Glu Lys Thr Gly Ile Leu Thr Val
                325                 330                 335

Thr Tyr His Ser Glu Thr Gln Arg Thr Lys Phe Leu Asn Thr Val Ala
            340                 345                 350

Ile Pro Asp Ser Val Gln Ile Leu Val Gly Tyr Met Thr Met
        355                 360                 365
```

<210> SEQ ID NO 24
<211> LENGTH: 18
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(18)
<223> OTHER INFORMATION: primer

<400> SEQUENCE: 24
gcgctttgag gatccaac 18

<210> SEQ ID NO 25
<211> LENGTH: 18
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(18)
<223> OTHER INFORMATION: primer

<400> SEQUENCE: 25
gttccgtgca cagatcag 18

<210> SEQ ID NO 26
<211> LENGTH: 20
<212> TYPE: DNA
<213> ORGANISM: artificial sequence
<220> FEATURE:

<223> OTHER INFORMATION: chemcially synthesized
<220> FEATURE:
<221> NAME/KEY: misc_feature
<222> LOCATION: (1)..(20)
<223> OTHER INFORMATION: primer

<400> SEQUENCE: 26
ggttgcagga actgtgaggt 20

<210> SEQ ID NO 27
<211> LENGTH: 22
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(22)
<223> OTHER INFORMATION: primer

<400> SEQUENCE: 27
tccgcgacag tcggggcaca gg 22

<210> SEQ ID NO 28
<211> LENGTH: 20
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: primer

<400> SEQUENCE: 28
gcggcgttat tcccatgacc 20

<210> SEQ ID NO 29
<211> LENGTH: 20
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: primer

<400> SEQUENCE: 29
ggtgcccttc cgtcaattcc 20

<210> SEQ ID NO 30
<211> LENGTH: 936
<212> TYPE: DNA
<213> ORGANISM: Renilla luciferase

<400> SEQUENCE: 30
atgacttcga aagtttatga tccagaacaa aggaaacgga tgataactgg tccgcagtgg 60
tgggccagat gtaaacaaat gaatgttctt gattcattta ttaattatta tgattcagaa 120
aaacatgcag aaaatgctgt tatttttta catggtaacg cggcctcttc ttatttatgg 180
cgacatgttg tgccacatat tgagccagta gcgcggtgta ttataccaga ccttattggt 240
atgggcaaat caggcaaatc tggtaatggt tcttataggt tacttgatca ttacaaatat 300
cttactgcat ggtttgaact tcttaattta ccaaagaaga tcatttttgt cggccatgat 360
tggggtgctt gtttggcatt tcattatagc tatgagcatc aagataagat caaagcaata 420
gttcacgctg aaagtgtagt agatgtgatt gaatcatggg atgaatggcc tgatattgaa 480
gaagatattg cgttgatcaa atctgaagaa ggagaaaaaa tggttttgga gaataacttc 540
ttcgtggaaa ccatgttgcc atcaaaaatc atgagaaagt tagaaccaga agaatttgca 600
gcatatcttg aaccattcaa agagaaaggt gaagttcgtc gtccaacatt atcatggcct 660
cgtgaaatcc cgttagtaaa aggtggtaaa cctgacgttg tacaaattgt taggaattat 720
aatgcttatc tacgtgcaag tgatgattta ccaaaaatgt ttattgaatc ggacccagga 780
ttcttttcca atgctattgt tgaaggtgcc aagaagtttc ctaatactga atttgtcaaa 840
gtaaaaggtc ttcatttttc gcaagaagat gcacctgatg aaatgggaaa atatatcaaa 900
tcgttcgttg agcgagttct caaaaatgaa caataa 936

<210> SEQ ID NO 31
<211> LENGTH: 27
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(27)
<223> OTHER INFORMATION: Pr1397 primer

<400> SEQUENCE: 31
cactacatac attgccgcca tgttcgc 27

<210> SEQ ID NO 32
<211> LENGTH: 27
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(27)
<223> OTHER INFORMATION: Pr904-1 primer

<400> SEQUENCE: 32
ctgctgggat gcacaccacg gacacac 27

<210> SEQ ID NO 33
<211> LENGTH: 1950
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1950)
<223> OTHER INFORMATION: HPV16 E1

<400> SEQUENCE: 33
atggctgatc ctgcaggtac caatggggaa gagggtacgg gatgtaatgg atggttttat 60
gtagaggctg tagtggaaaa aaaaacaggg gatgctatat cagatgacga gaacgaaaat 120
gacagtgata caggtgaaga tttggtagat tttatagtaa atgataatga ttatttaaca 180
caggcagaaa cagagacagc acatgcgttg tttactgcac aggaagcaaa acaacataga 240
gatgcagtac aggttctaaa acgaaagtat ttgggtagtc cacttagtga tattagtgga 300
tgtgtagaca ataatattag tcctagatta aaagctatat gtatagaaaa acaaagtaga 360
gctgcaaaaa ggagattatt tgaaagcgaa gacagcgggt atggcaatac tgaagtggaa 420

```
actcagcaga tgttacaggt agaagggcgc catgagactg aaacaccatg tagtcagtat    480
agtggtggaa gtgggggtgg ttgcagtcag tacagtagtg gaagtggggg agagggtgtt    540
agtgaaagac acactatatg ccaaacacca cttacaaata ttttaaatgt actaaaaact    600
agtaatgcaa aggcagcaat gttagcaaaa tttaaagagt tatacggggt gagtttttca    660
gaattagtaa gaccatttaa aagtaataaa tcaacgtgtt gcgattggtg tattgctgca    720
tttggactta cacccagtat agctgacagt ataaaaacac tattacaaca atattgttta    780
tatttacaca ttcaaagttt agcatgttca tggggaatgg ttgtgttact attagtaaga    840
tataaatgtg gaaaaaatag agaaacaatt gaaaaattgc tgtctaaact attatgtgtg    900
tctccaatgt gtatgatgat agagcctcca aaattgcgta gtacagcagc agcattatat    960
tggtataaaa caggtatatc aaatattagt gaagtgtatg gagacacgcc agaatggata   1020
caaagacaaa cagtattaca acatagtttt aatgattgta catttgaatt atcacagatg   1080
gtacaatggg cctacgataa tgacatagta gacgatagtg aaattgcata taaatatgca   1140
caattggcag acactaatag taatgcaagt gcctttctaa aaagtaattc acaggcaaaa   1200
attgtaaagg attgtgcaac aatgtgtaga cattataaac gagcagaaaa aaaacaaatg   1260
agtatgagtc aatggataaa atatagatgt gatagggtag atgatggagg tgattggaag   1320
caaattgtta tgtttttaag gtatcaaggt gtagagttta tgtcattttt aactgcatta   1380
aaaagatttt tgcaaggcat acctaaaaaa aattgcatat tactatatgg tgcagctaac   1440
acaggtaaat cattatttgg tatgagttta atgaaatttc tgcaagggtc tgtaatatgt   1500
tttgtaaatt ctaaaagcca tttttggtta caaccattag cagatgccaa aataggtatg   1560
ttagatgatg ctacagtgcc ctgttggaac tacatagatg acaatttaag aaatgcattg   1620
gatggaaatt tagtttctat ggatgtaaag catagaccat tggtacaact aaaatgccct   1680
ccattattaa ttacatctaa cattaatgct ggtacagatt ctaggtggcc ttatttacat   1740
aatagattgg tggtgtttac atttcctaat gagtttccat ttgacgaaaa cggaaatcca   1800
gtgtatgagc ttaatgataa gaactggaaa tcctttttct caaggacgtg gtccagatta   1860
agtttgcacg aggacgagga caaggaaaac gatggagact ctttgccaac gtttaaatgt   1920
gtgtcaggac aaaatactaa cacattatga                                   1950
```

```
<210> SEQ ID NO 34
<211> LENGTH: 1098
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(1098)
<223> OTHER INFORMATION: HPV16 E2

<400> SEQUENCE: 34

atggagactc tttgccaacg tttaaatgtg tgtcaggaca aaatactaac acattatgaa     60
aatgatagta cagacctacg tgaccatata gactattgga aacacatgcg cctagaatgt    120
gctatttatt acaaggccag agaaatggga tttaaacata ttaaccacca ggtggtgcca    180
acactggctg tatcaaagaa taaagcatta caagcaattg aactgcaact aacgttagaa    240
acaatatata actcacaata tagtaatgaa aagtggacat tacaagacgt tagccttgaa    300
gtgtatttaa ctgcaccaac aggatgtata aaaaaacatg gatatacagt ggaagtgcag    360
tttgatggag acatatgcaa tacaatgcat tatacaaact ggacacatat atatatttgt    420
```

```
gaagaagcat cagtaactgt ggtagagggt caagttgact attatggttt atattatgtt    480

catgaaggaa tacgaacata ttttgtgcag tttaaagatg atgcagaaaa atatagtaaa    540

aataaagtat gggaagttca tgcgggtggt caggtaatat tatgtcctac atctgtgttt    600

agcagcaacg aagtatcctc tcctgaaatt attaggcagc acttggccaa ccactccgcc    660

gcgacccata ccaaagccgt cgccttgggc accgaagaaa cacagacgac tatccagcga    720

ccaagatcag agccagacac cggaaacccc tgccacacca ctaagttgtt gcacagagac    780

tcagtggaca gtgctccaat cctcactgca tttaacagct cacacaaagg acggattaac    840

tgtaatagta acactacacc catagtacat ttaaaaggtg atgctaatac tttaaaatgt    900

ttaagatata gatttaaaaa gcattgtaca ttgtatactg cagtgtcgtc tacatggcat    960

tggacaggac ataatgtaaa acataaaagt gcaattgtta cacttacata tgatagtgaa   1020

tggcaacgtg accaattttt gtctcaagtt aaaataccaa aaactattac agtgtctact   1080

ggatttatgt ctatatga                                                 1098
```

```
<210> SEQ ID NO 35
<211> LENGTH: 720
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(720)
<223> OTHER INFORMATION: HPV 16 RLuc-E2 fusion protein

<400> SEQUENCE: 35

Met Glu Thr Leu Cys Gln Arg Leu Asn Val Cys Gln Asp Lys Ile Leu
1               5                   10                  15

Thr His Tyr Glu Ala Thr Ser Lys Val Tyr Asp Pro Glu Gln Arg Lys
            20                  25                  30

Arg Met Ile Thr Gly Pro Gln Trp Trp Ala Arg Cys Lys Gln Met Asn
        35                  40                  45

Val Leu Asp Ser Phe Ile Asn Tyr Tyr Asp Ser Glu Lys His Ala Glu
    50                  55                  60

Asn Ala Val Ile Phe Leu His Gly Asn Ala Ala Ser Ser Tyr Leu Trp
65                  70                  75                  80

Arg His Val Val Pro His Ile Glu Pro Val Ala Arg Cys Ile Ile Pro
                85                  90                  95

Asp Leu Ile Gly Met Gly Lys Ser Gly Lys Ser Gly Asn Gly Ser Tyr
            100                 105                 110

Arg Leu Leu Asp His Tyr Lys Tyr Leu Thr Ala Trp Phe Glu Leu Leu
        115                 120                 125

Asn Leu Pro Lys Lys Ile Ile Phe Val Gly His Asp Trp Gly Ala Cys
    130                 135                 140

Leu Ala Phe His Tyr Ser Tyr Glu His Gln Asp Lys Ile Lys Ala Ile
145                 150                 155                 160

Val His Ala Glu Ser Val Val Asp Val Ile Glu Ser Trp Asp Glu Trp
                165                 170                 175

Pro Asp Ile Glu Glu Asp Ile Ala Leu Ile Lys Ser Glu Glu Gly Glu
            180                 185                 190

Lys Met Val Leu Glu Asn Asn Phe Phe Val Glu Thr Met Leu Pro Ser
        195                 200                 205

Lys Ile Met Arg Lys Leu Glu Pro Glu Glu Phe Ala Ala Tyr Leu Glu
```

-continued

```
    210                 215                 220

Pro Phe Lys Glu Lys Gly Glu Val Arg Arg Pro Thr Leu Ser Trp Pro
225                 230                 235                 240

Arg Glu Ile Pro Leu Val Lys Gly Gly Lys Pro Asp Val Val Gln Ile
                245                 250                 255

Val Arg Asn Tyr Asn Ala Tyr Leu Arg Ala Ser Asp Asp Leu Pro Lys
            260                 265                 270

Met Phe Ile Glu Ser Asp Pro Gly Phe Phe Ser Asn Ala Ile Val Glu
        275                 280                 285

Gly Ala Lys Lys Phe Pro Asn Thr Glu Phe Val Lys Val Lys Gly Leu
    290                 295                 300

His Phe Ser Gln Glu Asp Ala Pro Asp Glu Met Gly Lys Tyr Ile Lys
305                 310                 315                 320

Ser Phe Val Glu Arg Val Leu Lys Asn Glu Gln Ala Pro Val Lys Gln
                325                 330                 335

Thr Leu Asn Phe Asp Leu Leu Lys Leu Ala Gly Asp Val Glu Ser Asn
            340                 345                 350

Pro Gly Pro Met Glu Thr Leu Cys Gln Arg Leu Asn Val Cys Gln Asp
        355                 360                 365

Lys Ile Leu Thr His Tyr Glu Asn Asp Ser Thr Asp Leu Arg Asp His
    370                 375                 380

Ile Asp Tyr Trp Lys His Met Arg Leu Glu Cys Ala Ile Tyr Tyr Lys
385                 390                 395                 400

Ala Arg Glu Met Gly Phe Lys His Ile Asn His Gln Val Val Pro Thr
                405                 410                 415

Leu Ala Val Ser Lys Asn Lys Ala Leu Gln Ala Ile Glu Leu Gln Leu
            420                 425                 430

Thr Leu Glu Thr Ile Tyr Asn Ser Gln Tyr Ser Asn Glu Lys Trp Thr
        435                 440                 445

Leu Gln Asp Val Ser Leu Glu Val Tyr Leu Thr Ala Pro Thr Gly Cys
    450                 455                 460

Ile Lys Lys His Gly Tyr Thr Val Glu Val Gln Phe Asp Gly Asp Ile
465                 470                 475                 480

Cys Asn Thr Met His Tyr Thr Asn Trp Thr His Ile Tyr Ile Cys Glu
                485                 490                 495

Glu Ala Ser Val Thr Val Val Glu Gly Gln Val Asp Tyr Tyr Gly Leu
            500                 505                 510

Tyr Tyr Val His Glu Gly Ile Arg Thr Tyr Phe Val Gln Phe Lys Asp
        515                 520                 525

Asp Ala Glu Lys Tyr Ser Lys Asn Lys Val Trp Glu Val His Ala Gly
    530                 535                 540

Gly Gln Val Ile Leu Cys Pro Thr Ser Val Phe Ser Ser Asn Glu Val
545                 550                 555                 560

Ser Ser Pro Glu Ile Ile Arg Gln His Leu Ala Asn His Ser Ala Ala
                565                 570                 575

Thr His Thr Lys Ala Val Ala Leu Gly Thr Glu Glu Thr Gln Thr Thr
            580                 585                 590

Ile Gln Arg Pro Arg Ser Glu Pro Asp Thr Gly Asn Pro Cys His Thr
        595                 600                 605

Thr Lys Leu Leu His Arg Asp Ser Val Asp Ser Ala Pro Ile Leu Thr
    610                 615                 620

Ala Phe Asn Ser Ser His Lys Gly Arg Ile Asn Cys Asn Ser Asn Thr
625                 630                 635                 640
```

```
Thr Pro Ile Val His Leu Lys Gly Asp Ala Asn Thr Leu Lys Cys Leu
                645                 650                 655

Arg Tyr Arg Phe Lys Lys His Cys Thr Leu Tyr Thr Ala Val Ser Ser
            660                 665                 670

Thr Trp His Trp Thr Gly His Asn Val Lys His Lys Ser Ala Ile Val
        675                 680                 685

Thr Leu Thr Tyr Asp Ser Glu Trp Gln Arg Asp Gln Phe Leu Ser Gln
    690                 695                 700

Val Lys Ile Pro Lys Thr Ile Thr Val Ser Thr Gly Phe Met Ser Ile
705                 710                 715                 720


<210> SEQ ID NO 36
<211> LENGTH: 20
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(20)
<223> OTHER INFORMATION: N-terminal amino acids of HPV16 E2 encoded by
      part of E2 ORF that is overlapped with E1 ORF

<400> SEQUENCE: 36

Met Glu Thr Leu Cys Gln Arg Leu Asn Val Cys Gln Asp Lys Ile Leu
1               5                   10                  15

Thr His Tyr Glu
            20


<210> SEQ ID NO 37
<211> LENGTH: 365
<212> TYPE: PRT
<213> ORGANISM: artificial sequence
<220> FEATURE:
<223> OTHER INFORMATION: chemically sytnhesized
<220> FEATURE:
<221> NAME/KEY: PEPTIDE
<222> LOCATION: (1)..(365)
<223> OTHER INFORMATION: Full-length HPV16 E2 protein starting from
      initiating methionine

<400> SEQUENCE: 37

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140
```

-continued

Val Thr Val Val Glu Gly Gln Val Asp Tyr Tyr Gly Leu Tyr Tyr Val
145 150 155 160

His Glu Gly Ile Arg Thr Tyr Phe Val Gln Phe Lys Asp Asp Ala Glu
165 170 175

Lys Tyr Ser Lys Asn Lys Val Trp Glu Val His Ala Gly Gly Gln Val
180 185 190

Ile Leu Cys Pro Thr Ser Val Phe Ser Ser Asn Glu Val Ser Ser Pro
195 200 205

Glu Ile Ile Arg Gln His Leu Ala Asn His Ser Ala Ala Thr His Thr
210 215 220

Lys Ala Val Ala Leu Gly Thr Glu Glu Thr Gln Thr Thr Ile Gln Arg
225 230 235 240

Pro Arg Ser Glu Pro Asp Thr Gly Asn Pro Cys His Thr Thr Lys Leu
245 250 255

Leu His Arg Asp Ser Val Asp Ser Ala Pro Ile Leu Thr Ala Phe Asn
260 265 270

Ser Ser His Lys Gly Arg Ile Asn Cys Asn Ser Asn Thr Thr Pro Ile
275 280 285

Val His Leu Lys Gly Asp Ala Asn Thr Leu Lys Cys Leu Arg Tyr Arg
290 295 300

Phe Lys Lys His Cys Thr Leu Tyr Thr Ala Val Ser Ser Thr Trp His
305 310 315 320

Trp Thr Gly His Asn Val Lys His Lys Ser Ala Ile Val Thr Leu Thr
325 330 335

Tyr Asp Ser Glu Trp Gln Arg Asp Gln Phe Leu Ser Gln Val Lys Ile
340 345 350

Pro Lys Thr Ile Thr Val Ser Thr Gly Phe Met Ser Ile
355 360 365

<210> SEQ ID NO 38
<211> LENGTH: 354
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(354)
<223> OTHER INFORMATION: Rluc protein fused with 22 N-terminal aa of HPV16 E2 + Ala at its N-teminus and with FMDV 2A peptide at its C-terminus

<400> SEQUENCE: 38

Met Glu Thr Leu Cys Gln Arg Leu Asn Val Cys Gln Asp Lys Ile Leu
1 5 10 15

Thr His Tyr Glu Ala Thr Ser Lys Val Tyr Asp Pro Glu Gln Arg Lys
20 25 30

Arg Met Ile Thr Gly Pro Gln Trp Trp Ala Arg Cys Lys Gln Met Asn
35 40 45

Val Leu Asp Ser Phe Ile Asn Tyr Tyr Asp Ser Glu Lys His Ala Glu
50 55 60

Asn Ala Val Ile Phe Leu His Gly Asn Ala Ala Ser Ser Tyr Leu Trp
65 70 75 80

Arg His Val Val Pro His Ile Glu Pro Val Ala Arg Cys Ile Ile Pro
85 90 95

Asp Leu Ile Gly Met Gly Lys Ser Gly Lys Ser Gly Asn Gly Ser Tyr
100 105 110

```
Arg Leu Leu Asp His Tyr Lys Tyr Leu Thr Ala Trp Phe Glu Leu Leu
        115                 120                 125

Asn Leu Pro Lys Lys Ile Ile Phe Val Gly His Asp Trp Gly Ala Cys
    130                 135                 140

Leu Ala Phe His Tyr Ser Tyr Glu His Gln Asp Lys Ile Lys Ala Ile
145                 150                 155                 160

Val His Ala Glu Ser Val Val Asp Val Ile Glu Ser Trp Asp Glu Trp
                165                 170                 175

Pro Asp Ile Glu Glu Asp Ile Ala Leu Ile Lys Ser Glu Glu Gly Glu
            180                 185                 190

Lys Met Val Leu Glu Asn Asn Phe Phe Val Glu Thr Met Leu Pro Ser
        195                 200                 205

Lys Ile Met Arg Lys Leu Glu Pro Glu Glu Phe Ala Ala Tyr Leu Glu
    210                 215                 220

Pro Phe Lys Glu Lys Gly Glu Val Arg Arg Pro Thr Leu Ser Trp Pro
225                 230                 235                 240

Arg Glu Ile Pro Leu Val Lys Gly Gly Lys Pro Asp Val Val Gln Ile
                245                 250                 255

Val Arg Asn Tyr Asn Ala Tyr Leu Arg Ala Ser Asp Asp Leu Pro Lys
            260                 265                 270

Met Phe Ile Glu Ser Asp Pro Gly Phe Phe Ser Asn Ala Ile Val Glu
        275                 280                 285

Gly Ala Lys Lys Phe Pro Asn Thr Glu Phe Val Lys Val Lys Gly Leu
    290                 295                 300

His Phe Ser Gln Glu Asp Ala Pro Asp Glu Met Gly Lys Tyr Ile Lys
305                 310                 315                 320

Ser Phe Val Glu Arg Val Leu Lys Asn Glu Gln Ala Pro Val Lys Gln
                325                 330                 335

Thr Leu Asn Phe Asp Leu Leu Lys Leu Ala Gly Asp Val Glu Ser Asn
            340                 345                 350

Pro Gly


<210> SEQ ID NO 39
<211> LENGTH: 366
<212> TYPE: PRT
<213> ORGANISM: artificial sequence
<220> FEATURE:
<223> OTHER INFORMATION: chemically synthesized
<220> FEATURE:
<221> NAME/KEY: PEPTIDE
<222> LOCATION: (1)..(366)
<223> OTHER INFORMATION: full-length HPV16 E2 protein containing
      additional Pro at N-terminal end

<400> SEQUENCE: 39

Pro Met Glu Thr Leu Cys Gln Arg Leu Asn Val Cys Gln Asp Lys Ile
1               5                   10                  15

Leu Thr His Tyr Glu Asn Asp Ser Thr Asp Leu Arg Asp His Ile Asp
            20                  25                  30

Tyr Trp Lys His Met Arg Leu Glu Cys Ala Ile Tyr Tyr Lys Ala Arg
        35                  40                  45

Glu Met Gly Phe Lys His Ile Asn His Gln Val Val Pro Thr Leu Ala
    50                  55                  60

Val Ser Lys Asn Lys Ala Leu Gln Ala Ile Glu Leu Gln Leu Thr Leu
65                  70                  75                  80

Glu Thr Ile Tyr Asn Ser Gln Tyr Ser Asn Glu Lys Trp Thr Leu Gln
                85                  90                  95
```

-continued

```
Asp Val Ser Leu Glu Val Tyr Leu Thr Ala Pro Thr Gly Cys Ile Lys
            100                 105                 110

Lys His Gly Tyr Thr Val Glu Val Gln Phe Asp Gly Asp Ile Cys Asn
        115                 120                 125

Thr Met His Tyr Thr Asn Trp Thr His Ile Tyr Ile Cys Glu Glu Ala
    130                 135                 140

Ser Val Thr Val Val Glu Gly Gln Val Asp Tyr Tyr Gly Leu Tyr Tyr
145                 150                 155                 160

Val His Glu Gly Ile Arg Thr Tyr Phe Val Gln Phe Lys Asp Asp Ala
                165                 170                 175

Glu Lys Tyr Ser Lys Asn Lys Val Trp Glu Val His Ala Gly Gly Gln
            180                 185                 190

Val Ile Leu Cys Pro Thr Ser Val Phe Ser Ser Asn Glu Val Ser Ser
        195                 200                 205

Pro Glu Ile Ile Arg Gln His Leu Ala Asn His Ser Ala Ala Thr His
    210                 215                 220

Thr Lys Ala Val Ala Leu Gly Thr Glu Glu Thr Gln Thr Thr Ile Gln
225                 230                 235                 240

Arg Pro Arg Ser Glu Pro Asp Thr Gly Asn Pro Cys His Thr Thr Lys
                245                 250                 255

Leu Leu His Arg Asp Ser Val Asp Ser Ala Pro Ile Leu Thr Ala Phe
            260                 265                 270

Asn Ser Ser His Lys Gly Arg Ile Asn Cys Asn Ser Asn Thr Thr Pro
        275                 280                 285

Ile Val His Leu Lys Gly Asp Ala Asn Thr Leu Lys Cys Leu Arg Tyr
    290                 295                 300

Arg Phe Lys Lys His Cys Thr Leu Tyr Thr Ala Val Ser Ser Thr Trp
305                 310                 315                 320

His Trp Thr Gly His Asn Val Lys His Lys Ser Ala Ile Val Thr Leu
                325                 330                 335

Thr Tyr Asp Ser Glu Trp Gln Arg Asp Gln Phe Leu Ser Gln Val Lys
            340                 345                 350

Ile Pro Lys Thr Ile Thr Val Ser Thr Gly Phe Met Ser Ile
        355                 360                 365


<210> SEQ ID NO 40
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: primer

<400> SEQUENCE: 40

cccacagcta cagatacac                                                   19


<210> SEQ ID NO 41
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: primer
```

<400> SEQUENCE: 41
gcaggtgtgg tatcagttg 19

<210> SEQ ID NO 42
<211> LENGTH: 13053
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(13053)
<223> OTHER INFORMATION: pMC_HPV16-RlucE2

<400> SEQUENCE: 42
acattaccct gttatcccta gatgacatta ccctgttatc ccagatgaca ttaccctgtt 60
atccctagat gacattaccc tgttatccct agatgacatt taccctgtta tccctagatg 120
acattaccct gttatcccag atgacattac cctgttatcc ctagatacat taccctgtta 180
tcccagatga cataccctgt tatccctaga tgacattacc ctgttatccc agatgacatt 240
accctgttat ccctagatac attaccctgt tatcccagat gacataccct gttatcccta 300
gatgacatta ccctgttatc ccagatgaca ttaccctgtt atccctagat acattaccct 360
gttatcccag atgacatacc ctgttatccc tagatgacat taccctgtta tcccagatga 420
cattaccctg ttatccctag atacattacc ctgttatccc agatgacata ccctgttatc 480
cctagatgac attaccctgt tatcccagat gacattaccc tgttatccct agatacatta 540
ccctgttatc ccagatgaca taccctgtta tccctagatg acattaccct gttatcccag 600
atgacattac cctgttatcc ctagatacat taccctgtta tcccagatga cataccctgt 660
tatccctaga tgacattacc ctgttatccc agataaactc aatgatgatg atgatgatgg 720
tcgagactca gcggccgcgg tgccagggcg tgcccttggg ctccccgggc gcgactagtg 780
aattcagatc cccatgtacc aatgttgcag taaatccagg tgattgtcca ccattagagt 840
taataaacac agttattcag gatggtgata tggttgatac tggctttggt gctatggact 900
ttactacatt acaggctaac aaaagtgaag ttccactgga tatttgtaca tctatttgca 960
aatatccaga ttatattaaa atggtgtcag aaccatatgg cgacagctta tttttttatt 1020
tacgaaggga acaaatgttt gttagacatt tatttaatag ggctggtgct gttggtgaaa 1080
atgtaccaga cgatttatac attaaaggct ctgggtctac tgcaaattta gccagttcaa 1140
attattttcc tacacctagt ggttctatgg ttacctctga tgcccaaata ttcaataaac 1200
cttattggtt acaacgagca cagggccaca ataatggcat ttgttggggt aaccaactat 1260
ttgttactgt tgttgatact acacgcagta caaatatgtc attatgtgct gccatatcta 1320
cttcagaaac tacatataaa aatactaact ttaaggagta cctacgacat ggggaggaat 1380
atgatttaca gtttattttt caactgtgca aaataacctt aactgcagac gttatgacat 1440
acatacattc tatgaattcc actattttgg aggactggaa ttttggtcta caacctcccc 1500
caggaggcac actagaagat acttataggt ttgtaacatc ccaggcaatt gcttgtcaaa 1560
aacatacacc tccagcacct aaagaagatc cccttaaaaa atacactttt tgggaagtaa 1620
atttaaagga aaagttttct gcagacctag atcagtttcc tttaggacgc aaatttttac 1680
tacaagcagg attgaaggcc aaaccaaaat ttacattagg aaaacgaaaa gctacaccca 1740
ccacctcatc tacctctaca actgctaaac gcaaaaaacg taagctgtaa gtattgtatg 1800

-continued

```
tatgttgaat tagtgttgtt tgttgtttat atgtttgtat gtgcttgtat gtgcttgtaa   1860
atattaagtt gtatgtgtgt ttgtatgtat ggtataataa acacgtgtgt atgtgttttt   1920
aaatgcttgt gtaactattg tgtcatgcaa cataaataaa cttattgttt caacacctac   1980
taattgtgtt gtggttattc attgtatata aactatattt gctacatcct gtttttgttt   2040
tatatatact aaattttgta gcgccagcgg ccattttgta gcttcaaccg aattcggttg   2100
catgcttttt ggcacaaaat gtgttttttt aaatagttct atgtcagcaa ctatagttta   2160
aacttgtacg tttcctgctt gccatgcgtg ccaaatccct gttttcctga cctgcactgc   2220
ttgccaacca ttccattgtt ttttacactg cactatgtgc aactactgaa tcactatgta   2280
cattgtgtca tataaaataa atcactatgc gccaacgcct tacataccgc tgttaggcac   2340
atatttttgg cttgttttaa ctaacctaat tgcatatttg gcataaggtt taaacttcta   2400
aggccaacta aatgtcaccc tagttcatac atgaactgtg taaaggttag tcatacattg   2460
ttcatttgta aaactgcaca tgggtgtgtg caaaccgttt tgggttacac atttacaagc   2520
aacttatata ataatactaa actacaataa ttcatgtata aaactaaggg cgtaaccgaa   2580
atcggttgaa ccgaaaccgg ttagtataaa agcagacatt ttatgcacca aaagagaact   2640
gcaatgtttc aggacccaca ggagcgaccc agaaagttac cacagttatg cacagagctg   2700
caaacaacta tacatgatat aatattagaa tgtgtgtact gcaagcaaca gttactgcga   2760
cgtgaggtat atgactttgc ttttcgggat ttatgtatag tatatagaga tgggaatcca   2820
tatgctgtat gtgataaatg tttaaagttt tattctaaaa ttagtgagta tagacattat   2880
tgttatagtg tgtatggaac aacattagaa cagcaataca acaaaccgtt gtgtgatttg   2940
ttaattaggt gtattaactg tcaaaagcca ctgtgtcctg aagaaaagca aagacatctg   3000
gacaaaaagc aaagattcca taatataagg ggtcggtgga ccggtcgatg tatgtcttgt   3060
tgcagatcat caagaacacg tagagaaacc cagctgtaat catgcatgga gatacaccta   3120
cattgcatga atatatgtta gatttgcaac cagagacaac tgatctctac tgttatgagc   3180
aattaaatga cagctcagag gaggaggatg aaatagatgg tccagctgga caagcagaac   3240
cggacagagc ccattacaat attgtaacct tttgttgcaa gtgtgactct acgcttcggt   3300
tgtgcgtaca aagcacacac gtagacattc gtactttgga agacctgtta atgggcacac   3360
taggaattgt gtgccccatc tgttctcaga aaccataatc taccatggct gatcctgcag   3420
gtaccaatgg ggaagagggt acgggatgta atggatggtt ttatgtagag gctgtagtgg   3480
aaaaaaaaac aggggatgct atatcagatg acgagaacga aaatgacagt gatacaggtg   3540
aagatttggt agattttata gtaaatgata atgattattt aacacaggca gaaacagaga   3600
cagcacatgc gttgtttact gcacaggaag caaaacaaca tagagatgca gtacaggttc   3660
taaaacgaaa gtatttgggt agtccactta gtgatattag tggatgtgta gacaataata   3720
ttagtcctag attaaaagct atatgtatag aaaaacaaag tagagctgca aaaaggagat   3780
tatttgaaag cgaagacagc gggtatggca atactgaagt ggaaactcag cagatgttac   3840
aggtagaagg gcgccatgag actgaaacac catgtagtca gtatagtggt ggaagtgggg   3900
gtggttgcag tcagtacagt agtggaagtg ggggagaggg tgttagtgaa agacacacta   3960
tatgccaaac accacttaca aatattttaa atgtactaaa aactagtaat gcaaaggcag   4020
caatgttagc aaaatttaaa gagttatacg gggtgagttt ttcagaatta gtaagaccat   4080
ttaaaagtaa taaatcaacg tgttgcgatt ggtgtattgc tgcatttgga cttacaccca   4140
gtatagctga cagtataaaa acactattac aacaatattg tttatattta cacattcaaa   4200
```

-continued gtttagcatg ttcatgggga atggttgtgt tactattagt aagatataaa tgtggaaaaa 4260
atagagaaac aattgaaaaa ttgctgtcta aactattatg tgtgtctcca atgtgtatga 4320
tgatagagcc tccaaaattg cgtagtacag cagcagcatt atattggtat aaaacaggta 4380
tatcaaatat tagtgaagtg tatggagaca cgccagaatg gatacaaaga caaacagtat 4440
tacaacatag ttttaatgat tgtacatttg aattatcaca gatggtacaa tgggcctacg 4500
ataatgacat agtagacgat agtgaaattg catataaata tgcacaattg gcagacacta 4560
atagtaatgc aagtgccttt ctaaaaagta attcacaggc aaaaattgta aaggattgtg 4620
caacaatgtg tagacattat aaacgagcag aaaaaaaaca aatgagtatg agtcaatgga 4680
taaaatatag atgtgatagg gtagatgatg gaggtgattg gaagcaaatt gttatgtttt 4740
taaggtatca aggtgtagag tttatgtcat ttttaactgc attaaaaaga tttttgcaag 4800
gcatacctaa aaaaaattgc atattactat atggtgcagc taacacaggt aaatcattat 4860
ttggtatgag tttaatgaaa tttctgcaag ggtctgtaat atgttttgta aattctaaaa 4920
gccatttttg gttacaacca ttagcagatg ccaaaatagg tatgttagat gatgctacag 4980
tgccctgttg gaactacata gatgacaatt taagaaatgc attggatgga aatttagttt 5040
ctatggatgt aaagcataga ccattggtac aactaaaatg ccctccatta ttaattacat 5100
ctaacattaa tgctggtaca gattctaggt ggccttattt acataataga ttggtggtgt 5160
ttacatttcc taatgagttt ccatttgacg aaaacggaaa tccagtgtat gagcttaatg 5220
ataagaactg gaaatccttt ttctcaagga cgtggtccag attaagtttg cacgaggacg 5280
aggacaagga aaacgatgga gactctttgc caacgtttaa atgtgtgtca ggacaaaata 5340
ctaacacatt atgaagctac ttcgaaagtt tatgatccag aacaaaggaa acggatgata 5400
actggtccgc agtggtgggc cagatgtaaa caaatgaatg ttcttgattc atttattaat 5460
tattatgatt cagaaaaaca tgcagaaaat gctgttattt ttttacatgg taacgcggcc 5520
tcttcttatt tatggcgaca tgttgtgcca catattgagc cagtagcgcg gtgtattata 5580
ccagacctta ttggtatggg caaatcaggc aaatctggta atggttctta taggttactt 5640
gatcattaca aatatcttac tgcatggttt gaacttctta atttaccaaa gaagatcatt 5700
tttgtcggcc atgattgggg tgcttgtttg gcatttcatt atagctatga gcatcaagat 5760
aagatcaaag caatagttca cgctgaaagt gtagtagatg tgattgaatc atgggatgaa 5820
tggcctgata ttgaagaaga tattgcgttg atcaaatctg aagaaggaga aaaaatggtt 5880
ttggagaata acttcttcgt ggaaaccatg ttgccatcaa aaatcatgag aaagttagaa 5940
ccagaagaat ttgcagcata tcttgaacca ttcaaagaga aaggtgaagt tcgtcgtcca 6000
acattatcat ggcctcgtga aatcccgtta gtaaaaggtg gtaaacctga cgttgtacaa 6060
attgttagga attataatgc ttatctacgt gcaagtgatg atttaccaaa aatgtttatt 6120
gaatcggacc caggattctt ttccaatgct attgttgaag gtgccaagaa gtttcctaat 6180
actgaatttg tcaaagtaaa aggtcttcat ttttcgcaag aagatgcacc tgatgaaatg 6240
ggaaaatata tcaaatcgtt cgttgagcga gttctcaaaa atgaacaagc accggtgaaa 6300
cagactttga attttgacct tctcaagttg gcgggagacg tggagtccaa ccctgggccc 6360
atggagactc tttgccaacg tttaaatgtg tgtcaggaca aaatactaac acattatgaa 6420
aatgatagta cagacctacg tgaccatata gactattgga aacacatgcg cctagaatgt 6480
gctatttatt acaaggccag agaaatggga tttaaacata ttaaccacca ggtggtgcca 6540

-continued

```
acactggctg tatcaaagaa taaagcatta caagcaattg aactgcaact aacgttagaa   6600
acaatatata actcacaata tagtaatgaa aagtggacat tacaagacgt tagccttgaa   6660
gtgtatttaa ctgcaccaac aggatgtata aaaaaacatg gatatacagt ggaagtgcag   6720
tttgatggag acatatgcaa tacaatgcat tatacaaact ggacacatat atatatttgt   6780
gaagaagcat cagtaactgt ggtagagggt caagttgact attatggttt atattatgtt   6840
catgaaggaa tacgaacata ttttgtgcag tttaaagatg atgcagaaaa atatagtaaa   6900
aataaagtat gggaagttca tgcgggtggt caggtaatat tatgtcctac atctgtgttt   6960
agcagcaacg aagtatcctc tcctgaaatt attaggcagc acttggccaa ccactccgcc   7020
gcgacccata ccaaagccgt cgccttgggc accgaagaaa cacagacgac tatccagcga   7080
ccaagatcag agccagacac cggaaacccc tgccacacca ctaagttgtt gcacagagac   7140
tcagtggaca gtgctccaat cctcactgca tttaacagct cacacaaagg acggattaac   7200
tgtaatagta acactacacc catagtacat ttaaaaggtg atgctaatac tttaaaatgt   7260
ttaagatata gatttaaaaa gcattgtaca ttgtatactg cagtgtcgtc tacatggcat   7320
tggacaggac ataatgtaaa acataaaagt gcaattgtta cacttacata tgatagtgaa   7380
tggcaacgtg accaattttt gtctcaagtt aaaataccaa aaactattac agtgtctact   7440
ggatttatgt ctatatgaca aatcttgata ctgcatccac aacattactg gcgtgctttt   7500
tgctttgctt ttgtgtgctt ttgtgtgtct gcctattaat acgtccgctg cttttgtctg   7560
tgtctacata cacatcatta atactattgg tattactatt gtggataaca gcagcctctg   7620
cgtttaggtg ttttattgta tatattgtat ttgtttatat accattattt ttaatacata   7680
cacatgcacg ctttttaatt acataatgta tatgtacaaa atgtaattgt tacatataat   7740
tgttgtatac cataacttac tatttttttct tttttatttt catatatatt ttttttttgt   7800
ttgtttgttt gttttttaat aaactgttat cacttaacaa tgcgacacaa acgttctgca   7860
aaacgcacaa aacgtgcatc ggctacccaa ctttataaaa catgcaaaca ggcaggtaca   7920
tgtccacctg acattatacc taaggttgaa ggcaaaacta ttgctgatca aatattacaa   7980
tatggaagta tgggtgtatt ttttggtggg ttaggaattg gaacagggtc gggtacaggc   8040
ggacgcactg ggtatattcc attgggaaca aggcctccca cagctacaga tacacttgct   8100
cctgtaagac cccctttaac agtagatcct gtgggccctt ccgatccttc tatagtttct   8160
ttagtggaag aaactagttt tattgatgct ggtgcaccaa catctgtacc ttccattccc   8220
ccagatgtat caggatttag tattactact tcaactgata ccacacctgc tatattagat   8280
attaataata ctgttactac tgttactaca cataataatc ccactttcac tgacccatct   8340
gtattgcagc ctccaacacc tgcagaaact ggagggcatt ttacactttc atcatccact   8400
attagtacac ataattatga agaaattcct atggatacat ttattgttag cacaaaccct   8460
aacacagtaa ctagtagcac acccatacca gggtctcgcc cagtggcacg cctaggatta   8520
tatagtcgca caacacaaca agttaaagtt gtagaccctg cttttataac cactcccact   8580
aaacttatta catatgataa tcctgcatat gaaggtatag atgtggataa tacattatat   8640
ttttctagta atgataatag tattaatata gctccagatc ctgacttttt ggatatagtt   8700
gctttacata ggccagcatt aacctctagg cgtactggca ttaggtacag tagaattggt   8760
aataaacaaa cactacgtac tcgtagtgga aaatctatag gtgctaaggt acattattat   8820
tatgatttta gtactattga ttctgcagaa gaaatagaat tacaaactat aacaccttct   8880
acatatacta ccacttcaca tgcagcctta cctacttcta ttaataatgg attatatgat   8940
```

```
atttatgcag atgactttat tacagatact tctacaaccc cggtaccatc tgtaccctct   9000
acatctttat caggttatat tcctgcaaat acaacaattc cttttggtgg tgcatacaat   9060
attcctttag tatcaggtcc tgatataccc attaatataa ctgaccaagc tccttcatta   9120
attcctatag ttccagggtc tccacaatat acaattattg ctgatgcagg tgacttttat   9180
ttacatccta gttattacat gttacgaaaa cgacgtaaac gtttaccata ttttttttca   9240
gatgtctctt tggctgccta gtgaggccac tgtctacttg cctcctgtcc cagtatctaa   9300
ggttgtaagc acggatgaat atgttgcacg cacaaacata tattatcatg caggaacatc   9360
cagactactt gcagttggac atccctattt tcctattaaa aaacctaaca ataacaaaat   9420
attagttcct aaagtatcag gattacaata cagggtattt agaatacatt tacctgaccc   9480
caataagttt ggttttcctg acacctcatt ttataatcca gatacacagc ggctggtttg   9540
ggcctgtgta ggtgttgagg taggccgtgg tcagccatta ggtgtgggca ttagtggcca   9600
tcctttatta aataaattgg atgacacaga aaatgctagt gcttatgcag caaatgcagg   9660
tgtggataat agagaatgta tatctatgga ttacaaacaa acacaattgt gtttaattgg   9720
ttgcaaacca cctatagggg aacactgggg caaaggatct gatatctcta gagtcgaccc   9780
atgggggccc gccccaactg gggtaacctt tgagttctct cagttggggg taatcagcat   9840
catgatgtgg taccacatca tgatgctgat tataagaatg cggccgccac actctagtgg   9900
atctcgagtt aataattcag aagaactcgt caagaaggcg atagaaggcg atgcgctgcg   9960
aatcgggagc ggcgataccg taaagcacga ggaagcggtc agcccattcg ccgccaagct  10020
cttcagcaat atcacgggta gccaacgcta tgtcctgata gcggtccgcc acacccagcc  10080
ggccacagtc gatgaatcca gaaaagcggc cattttccac catgatattc ggcaagcagg  10140
catcgccatg ggtcacgacg agatcctcgc cgtcgggcat gctcgccttg agcctggcga  10200
acagttcggc tggcgcgagc ccctgatgct cttcgtccag atcatcctga tcgacaagac  10260
cggcttccat ccgagtacgt gctcgctcga tgcgatgttt cgcttggtgg tcgaatgggc  10320
aggtagccgg atcaagcgta tgcagccgcc gcattgcatc agccatgatg gatactttct  10380
cggcaggagc aaggtgtaga tgacatggag atcctgcccc ggcacttcgc ccaatagcag  10440
ccagtccctt cccgcttcag tgacaacgtc gagcacagct gcgcaaggaa cgcccgtcgt  10500
ggccagccac gatagccgcg ctgcctcgtc ttgcagttca ttcagggcac cggacaggtc  10560
ggtcttgaca aaaagaaccg ggcgcccctg cgctgacagc cggaacacgg cggcatcaga  10620
gcagccgatt gtctgttgtg cccagtcata gccgaatagc ctctccaccc aagcggccgg  10680
agaacctgcg tgcaatccat cttgttcaat catgcgaaac gatcctcatc ctgtctcttg  10740
atcagagctt gatcccctgc gccatcagat ccttggcggc gagaaagcca tccagtttac  10800
tttgcagggc ttcccaacct taccagaggg cgccccagct ggcaattccg gttcgcttgc  10860
tgtccataaa accgcccagt ctagctatcg ccatgtaagc ccactgcaag ctacctgctt  10920
tctctttgcg cttgcgtttt cccttgtcca gatagcccag tagctgacat tcatccgggg  10980
tcagcaccgt ttctgcggac tggctttcta cgtgctcgag gggggccaaa cggtctccag  11040
cttggctgtt ttggcggatg agagaagatt ttcagcctga tacagattaa atcagaacgc  11100
agaagcggtc tgataaaaca gaatttgcct ggcggcagta gcgcggtggt cccacctgac  11160
cccatgccga actcagaagt gaaacgccgt agcgccgatg gtagtgtggg gtctccccat  11220
gcgagagtag ggaactgcca ggcatcaaat aaaacgaaag gctcagtcga aagactgggc  11280
```

```
ctttcgtttt atctgttgtt tgtcggtgaa cgctctcctg agtaggacaa atccgccggg  11340

agcggatttg aacgttgcga agcaacggcc cggagggtgg cgggcaggac gcccgccata  11400

aactgccagg catcaaatta agcagaaggc catcctgacg gatggccttt ttgcgtttct  11460

acaaactctt ttgtttattt ttctaaatac attcaaatat gtatccgctc atgaccaaaa  11520

tcccttaacg tgagttttcg ttccactgag cgtcagaccc cgtagaaaag atcaaaggat  11580

cttcttgaga tccttttttt ctgcgcgtaa tctgctgctt gcaaacaaaa aaaccaccgc  11640

taccagcggt ggtttgtttg ccggatcaag agctaccaac tctttttccg aaggtaactg  11700

gcttcagcag agcgcagata ccaaatactg tccttctagt gtagccgtag ttaggccacc  11760

acttcaagaa ctctgtagca ccgcctacat acctcgctct gctaatcctg ttaccagtgg  11820

ctgctgccag tggcgataag tcgtgtctta ccgggttgga ctcaagacga tagttaccgg  11880

ataaggcgca gcggtcgggc tgaacggggg gttcgtgcac acagcccagc ttggagcgaa  11940

cgacctacac cgaactgaga tacctacagc gtgagctatg agaaagcgcc acgcttcccg  12000

aagggagaaa ggcggacagg tatccggtaa gcggcagggt cggaacagga gagcgcacga  12060

gggagcttcc agggggaaac gcctggtatc tttatagtcc tgtcgggttt cgccacctct  12120

gacttgagcg tcgatttttg tgatgctcgt caggggggcg gagcctatgg aaaaacgcca  12180

gcaacgcggc ctttttacgg ttcctggcct tttgctggcc ttttgctcac atgttctttc  12240

ctgcgttatc ccctgattct gtggataacc gtattaccgc ctttgagtga gctgataccg  12300

ctcgccgcag ccgaacgacc gagcgcagcg agtcagtgag cgaggaagcg gaagagcgcc  12360

tgatgcggta ttttctcctt acgcatctgt gcggtatttc acaccgcata tggtgcactc  12420

tcagtacaat ctgctctgat gccgcatagt taagccagta tacactccgc tatcgctacg  12480

tgactgggtc atggctgcgc cccgacaccc gccaacaccc gctgacgcgc cctgacgggc  12540

ttgtctgctc ccggcatccg cttacagaca agctgtgacc gtctccggga gctgcatgtg  12600

tcagaggttt tcaccgtcat caccgaaacg cgcgaggcag cagatcaatt cgcgcgcgaa  12660

ggcgaagcgg catgcataat gtgcctgtca aatggacgaa gcagggattc tgcaaaccct  12720

atgctactcc gtcaagccgt caattgtctg attcgttacc aattatgaca acttgacggc  12780

tacatcattc actttttctt cacaaccggc acggaactcg ctcgggctgg ccccggtgca  12840

tttttaaat acccgcgaga aatagagttg atcgtcaaaa ccaacattgc gaccgacggt  12900

ggcgataggc atccgggtgg tgctcaaaag cagcttcgcc tggctgatac gttggtcctc  12960

gcgccagctt aagacgctaa tccctaactg ctggcggaaa agatgtgaca gacgcgacgg  13020

cgacaagcaa acatgctgtg cgacgctggc gat                                13053
```

<210> SEQ ID NO 43
<211> LENGTH: 9149
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(9149)
<223> OTHER INFORMATION: HPV16-RlucE2 marker genome

<400> SEQUENCE: 43

```
ggccgcggtg ccagggcgtg cccttgggct ccccgggcgc gactagtgaa ttcagatccc     60

catgtaccaa tgttgcagta aatccaggtg attgtccacc attagagtta ataaacacag    120

ttattcagga tggtgatatg gttgatactg gctttggtgc tatggacttt actacattac    180
```

```
aggctaacaa aagtgaagtt ccactggata tttgtacatc tatttgcaaa tatccagatt    240
atattaaaat ggtgtcagaa ccatatggcg acagcttatt tttttattta cgaagggaac    300
aaatgtttgt tagacattta tttaataggg ctggtgctgt tggtgaaaat gtaccagacg    360
atttatacat taaaggctct gggtctactg caaatttagc cagttcaaat tattttccta    420
cacctagtgg ttctatggtt acctctgatg cccaaatatt caataaacct tattggttac    480
aacgagcaca gggccacaat aatggcattt gttggggtaa ccaactattt gttactgttg    540
ttgatactac acgcagtaca aatatgtcat tatgtgctgc catatctact tcagaaacta    600
catataaaaa tactaacttt aaggagtacc tacgacatgg ggaggaatat gatttacagt    660
ttatttttca actgtgcaaa ataaccttaa ctgcagacgt tatgacatac atacattcta    720
tgaattccac tattttggag gactggaatt ttggtctaca acctccccca ggaggcacac    780
tagaagatac ttataggttt gtaacatccc aggcaattgc ttgtcaaaaa catacacctc    840
cagcacctaa agaagatccc cttaaaaaat acactttttg ggaagtaaat ttaaaggaaa    900
agttttctgc agacctagat cagtttcctt taggacgcaa atttttacta caagcaggat    960
tgaaggccaa accaaaattt acattaggaa aacgaaaagc tacacccacc acctcatcta   1020
cctctacaac tgctaaacgc aaaaaacgta agctgtaagt attgtatgta tgttgaatta   1080
gtgttgtttg ttgtttatat gtttgtatgt gcttgtatgt gcttgtaaat attaagttgt   1140
atgtgtgttt gtatgtatgg tataataaac acgtgtgtat gtgtttttaa atgcttgtgt   1200
aactattgtg tcatgcaaca taaataaact tattgtttca acacctacta attgtgttgt   1260
ggttattcat tgtatataaa ctatatttgc tacatcctgt tttgtttta tatatactaa    1320
attttgtagc gccagcggcc attttgtagc ttcaaccgaa ttcggttgca tgctttttgg   1380
cacaaaatgt gtttttttaa atagttctat gtcagcaact atagtttaaa cttgtacgtt   1440
tcctgcttgc catgcgtgcc aaatccctgt tttcctgacc tgcactgctt gccaaccatt   1500
ccattgtttt ttacactgca ctatgtgcaa ctactgaatc actatgtaca ttgtgtcata   1560
taaaataaat cactatgcgc caacgcctta cataccgctg ttaggcacat atttttggct   1620
tgttttaact aacctaattg catatttggc ataaggttta aacttctaag gccaactaaa   1680
tgtcacccta gttcatacat gaactgtgta aaggttagtc atacattgtt catttgtaaa   1740
actgcacatg ggtgtgtgca aaccgttttg ggttacacat ttacaagcaa cttatataat   1800
aatactaaac tacaataatt catgtataaa actaagggcg taaccgaaat cggttgaacc   1860
gaaaccggtt agtataaaag cagacatttt atgcaccaaa agagaactgc aatgtttcag   1920
gacccacagg agcgacccag aaagttacca cagttatgca cagagctgca aacaactata   1980
catgatataa tattagaatg tgtgtactgc aagcaacagt tactgcgacg tgaggtatat   2040
gactttgctt ttcgggattt atgtatagta tatagagatg ggaatccata tgctgtatgt   2100
gataaatgtt taaagtttta ttctaaaatt agtgagtata gacattattg ttatagtgtg   2160
tatggaacaa cattagaaca gcaatacaac aaaccgttgt gtgatttgtt aattaggtgt   2220
attaactgtc aaaagccact gtgtcctgaa gaaaagcaaa gacatctgga caaaaagcaa   2280
agattccata atataagggg tcggtggacc ggtcgatgta tgtcttgttg cagatcatca   2340
agaacacgta gagaaaccca gctgtaatca tgcatggaga tacacctaca ttgcatgaat   2400
atatgttaga tttgcaacca gagacaactg atctctactg ttatgagcaa ttaaatgaca   2460
gctcagagga ggaggatgaa atagatggtc cagctggaca agcagaaccg gacagagccc   2520
```

-continued

```
attacaatat tgtaaccttt tgttgcaagt gtgactctac gcttcggttg tgcgtacaaa   2580
gcacacacgt agacattcgt actttggaag acctgttaat gggcacacta ggaattgtgt   2640
gccccatctg ttctcagaaa ccataatcta ccatggctga tcctgcaggt accaatgggg   2700
aagagggtac gggatgtaat ggatggtttt atgtagaggc tgtagtggaa aaaaaaacag   2760
gggatgctat atcagatgac gagaacgaaa atgacagtga tacaggtgaa gatttggtag   2820
attttatagt aaatgataat gattatttaa cacaggcaga aacagagaca gcacatgcgt   2880
tgtttactgc acaggaagca aaacaacata gagatgcagt acaggttcta aaacgaaagt   2940
atttgggtag tccacttagt gatattagtg gatgtgtaga caataatatt agtcctagat   3000
taaaagctat atgtatagaa aaacaaagta gagctgcaaa aaggagatta tttgaaagcg   3060
aagacagcgg gtatggcaat actgaagtgg aaactcagca gatgttacag gtagaagggc   3120
gccatgagac tgaaacacca tgtagtcagt atagtggtgg aagtgggggt ggttgcagtc   3180
agtacagtag tggaagtggg ggagagggtg ttagtgaaag acacactata tgccaaacac   3240
cacttacaaa tattttaaat gtactaaaaa ctagtaatgc aaaggcagca atgttagcaa   3300
aatttaaaga gttatacggg gtgagttttt cagaattagt aagaccattt aaaagtaata   3360
aatcaacgtg ttgcgattgg tgtattgctg catttggact tacacccagt atagctgaca   3420
gtataaaaac actattacaa caatattgtt tatatttaca cattcaaagt ttagcatgtt   3480
catggggaat ggttgtgtta ctattagtaa gatataaatg tggaaaaaat agagaaacaa   3540
ttgaaaaatt gctgtctaaa ctattatgtg tgtctccaat gtgtatgatg atagagcctc   3600
caaaattgcg tagtacagca gcagcattat attggtataa aacaggtata tcaaatatta   3660
gtgaagtgta tggagacacg ccagaatgga tacaaagaca aacagtatta caacatagtt   3720
ttaatgattg tacatttgaa ttatcacaga tggtacaatg ggcctacgat aatgacatag   3780
tagacgatag tgaaattgca tataaatatg cacaattggc agacactaat agtaatgcaa   3840
gtgcctttct aaaaagtaat tcacaggcaa aaattgtaaa ggattgtgca acaatgtgta   3900
gacattataa acgagcagaa aaaaaacaaa tgagtatgag tcaatggata aaatatagat   3960
gtgatagggt agatgatgga ggtgattgga agcaaattgt tatgttttta aggtatcaag   4020
gtgtagagtt tatgtcattt ttaactgcat taaaaagatt tttgcaaggc atacctaaaa   4080
aaaattgcat attactatat ggtgcagcta acacaggtaa atcattattt ggtatgagtt   4140
taatgaaatt tctgcaaggg tctgtaatat gttttgtaaa ttctaaaagc catttttggt   4200
tacaaccatt agcagatgcc aaaataggta tgttagatga tgctacagtg ccctgttgga   4260
actacataga tgacaattta agaaatgcat tggatggaaa tttagtttct atggatgtaa   4320
agcatagacc attggtacaa ctaaaatgcc ctccattatt aattacatct aacattaatg   4380
ctggtacaga ttctaggtgg ccttatttac ataatagatt ggtggtgttt acatttccta   4440
atgagtttcc atttgacgaa aacggaaatc cagtgtatga gcttaatgat aagaactgga   4500
aatccttttt ctcaaggacg tggtccagat taagtttgca cgaggacgag gacaaggaaa   4560
acgatggaga ctctttgcca acgtttaaat gtgtgtcagg acaaaatact aacacattat   4620
gaagctactt cgaaagttta tgatccagaa caaaggaaac ggatgataac tggtccgcag   4680
tggtgggcca gatgtaaaca aatgaatgtt cttgattcat ttattaatta ttatgattca   4740
gaaaaacatg cagaaaatgc tgttattttt ttacatggta acgcggcctc ttcttattta   4800
tggcgacatg ttgtgccaca tattgagcca gtagcgcggt gtattatacc agaccttatt   4860
ggtatgggca aatcaggcaa atctggtaat ggttcttata ggttacttga tcattacaaa   4920
```

tatcttactg catggtttga acttcttaat ttaccaaaga agatcatttt tgtcggccat 4980
gattggggtg cttgtttggc atttcattat agctatgagc atcaagataa gatcaaagca 5040
atagttcacg ctgaaagtgt agtagatgtg attgaatcat gggatgaatg gcctgatatt 5100
gaagaagata ttgcgttgat caaatctgaa gaaggagaaa aaatggtttt ggagaataac 5160
ttcttcgtgg aaaccatgtt gccatcaaaa atcatgagaa agttagaacc agaagaattt 5220
gcagcatatc ttgaaccatt caaagagaaa ggtgaagttc gtcgtccaac attatcatgg 5280
cctcgtgaaa tcccgttagt aaaaggtggt aaacctgacg ttgtacaaat tgttaggaat 5340
tataatgctt atctacgtgc aagtgatgat ttaccaaaaa tgtttattga atcggaccca 5400
ggattctttt ccaatgctat tgttgaaggt gccaagaagt ttcctaatac tgaatttgtc 5460
aaagtaaaag gtcttcattt ttcgcaagaa gatgcacctg atgaaatggg aaaatatatc 5520
aaatcgttcg ttgagcgagt tctcaaaaat gaacaagcac cggtgaaaca gactttgaat 5580
tttgaccttc tcaagttggc gggagacgtg gagtccaacc ctgggcccat ggagactctt 5640
tgccaacgtt taaatgtgtg tcaggacaaa atactaacac attatgaaaa tgatagtaca 5700
gacctacgtg accatataga ctattggaaa cacatgcgcc tagaatgtgc tatttattac 5760
aaggccagag aaatgggatt taaacatatt aaccaccagg tggtgccaac actggctgta 5820
tcaaagaata aagcattaca agcaattgaa ctgcaactaa cgttagaaac aatatataac 5880
tcacaatata gtaatgaaaa gtggacatta caagacgtta gccttgaagt gtatttaact 5940
gcaccaacag gatgtataaa aaaacatgga tatacagtgg aagtgcagtt tgatggagac 6000
atatgcaata caatgcatta tacaaactgg acacatatat atatttgtga agaagcatca 6060
gtaactgtgg tagagggtca agttgactat tatggtttat attatgttca tgaaggaata 6120
cgaacatatt ttgtgcagtt taaagatgat gcagaaaaat atagtaaaaa taaagtatgg 6180
gaagttcatg cgggtggtca ggtaatatta tgtcctacat ctgtgtttag cagcaacgaa 6240
gtatcctctc ctgaaattat taggcagcac ttggccaacc actccgccgc gacccatacc 6300
aaagccgtcg ccttgggcac cgaagaaaca cagacgacta tccagcgacc aagatcagag 6360
ccagacaccg gaaacccctg ccacaccact aagttgttgc acagagactc agtggacagt 6420
gctccaatcc tcactgcatt taacagctca cacaaaggac ggattaactg taatagtaac 6480
actacaccca tagtacattt aaaaggtgat gctaatactt taaaatgttt aagatataga 6540
tttaaaaagc attgtacatt gtatactgca gtgtcgtcta catggcattg gacaggacat 6600
aatgtaaaac ataaaagtgc aattgttaca cttacatatg atagtgaatg gcaacgtgac 6660
caatttttgt ctcaagttaa aataccaaaa actattacag tgtctactgg atttatgtct 6720
atatgacaaa tcttgatact gcatccacaa cattactggc gtgctttttg ctttgctttt 6780
gtgtgctttt gtgtgtctgc ctattaatac gtccgctgct tttgtctgtg tctacataca 6840
catcattaat actattggta ttactattgt ggataacagc agcctctgcg tttaggtgtt 6900
ttattgtata tattgtattt gtttatatac cattattttt aatacataca catgcacgct 6960
ttttaattac ataatgtata tgtacaaaat gtaattgtta catataattg ttgtatacca 7020
taacttacta ttttttcttt tttattttca tatatatttt ttttttgttt gtttgtttgt 7080
tttttaataa actgttatca cttaacaatg cgacacaaac gttctgcaaa acgcacaaaa 7140
cgtgcatcgg ctacccaact ttataaaaca tgcaaacagg caggtacatg tccacctgac 7200
attataccta aggttgaagg caaaactatt gctgatcaaa tattacaata tggaagtatg 7260

-continued ggtgtatttt ttggtgggtt aggaattgga acagggtcgg gtacaggcgg acgcactggg 7320
tatattccat tgggaacaag gcctcccaca gctacagata cacttgctcc tgtaagaccc 7380
cctttaacag tagatcctgt gggcccttcc gatccttcta tagtttcttt agtggaagaa 7440
actagtttta ttgatgctgg tgcaccaaca tctgtacctt ccattccccc agatgtatca 7500
ggatttagta ttactacttc aactgatacc acacctgcta tattagatat taataatact 7560
gttactactg ttactacaca taataatccc actttcactg acccatctgt attgcagcct 7620
ccaacacctg cagaaactgg agggcatttt acactttcat catccactat tagtacacat 7680
aattatgaag aaattcctat ggatacattt attgttagca caaaccctaa cacagtaact 7740
agtagcacac ccataccagg gtctcgccca gtggcacgcc taggattata tagtcgcaca 7800
acacaacaag ttaaagttgt agaccctgct tttataacca ctcccactaa acttattaca 7860
tatgataatc ctgcatatga aggtatagat gtggataata cattatattt ttctagtaat 7920
gataatagta ttaatatagc tccagatcct gactttttgg atatagttgc tttacatagg 7980
ccagcattaa cctctaggcg tactggcatt aggtacagta gaattggtaa taaacaaaca 8040
ctacgtactc gtagtggaaa atctataggt gctaaggtac attattatta tgattttagt 8100
actattgatt ctgcagaaga aatagaatta caaactataa caccttctac atatactacc 8160
acttcacatg cagccttacc tacttctatt aataatggat tatatgatat ttatgcagat 8220
gactttatta cagatacttc tacaaccccg gtaccatctg taccctctac atctttatca 8280
ggttatattc ctgcaaatac aacaattcct tttggtggtg catacaatat tcctttagta 8340
tcaggtcctg atatacccat taatataact gaccaagctc cttcattaat tcctatagtt 8400
ccagggtctc cacaatatac aattattgct gatgcaggtg acttttattt acatcctagt 8460
tattacatgt tacgaaaacg acgtaaacgt ttaccatatt ttttttcaga tgtctctttg 8520
gctgcctagt gaggccactg tctacttgcc tcctgtccca gtatctaagg ttgtaagcac 8580
ggatgaatat gttgcacgca caaacatata ttatcatgca ggaacatcca gactacttgc 8640
agttggacat ccctattttc ctattaaaaa acctaacaat aacaaaatat tagttcctaa 8700
agtatcagga ttacaataca gggtatttag aatacattta cctgacccca ataagtttgg 8760
ttttcctgac acctcatttt ataatccaga tacacagcgg ctggtttggg cctgtgtagg 8820
tgttgaggta ggccgtggtc agccattagg tgtgggcatt agtggccatc ctttattaaa 8880
taaattggat gacacagaaa atgctagtgc ttatgcagca aatgcaggtg tggataatag 8940
agaatgtata tctatggatt acaaacaaac acaattgtgt ttaattggtt gcaaaccacc 9000
tataggggaa cactggggca aaggatctga tatctctaga gtcgacccat gggggcccgc 9060
cccaactggg gtaacctttg agttctctca gttgggggta atcagcatca tgatgtggta 9120
ccacatcatg atgctgatta taagaatgc 9149

ASSAY SYSTEM TO IDENTIFY HPV REPLICATION INHIBITORS IN HT-SCREEN

PRIORITY CLAIM

This application is a U.S. national application of the international application number PCT/EP2016/057898 filed on Apr. 1, 2016 and claiming priority of U.S. provisional application No. 62/145,243 filed on Apr. 9, 2015, the contents of both of which are incorporated herein by reference.

SEQUENCE LISTING

This application contains sequence data provided in computer readable format.

TECHNICAL FIELD OF THE INVENTION

The present invention relates to the fields of virology, cell biology, cell culturing, and drug development. More particularly the invention provides a method for screening for anti-HPV substances and a kit for screening for anti-HPV substances. The invention also provides plasmids for transfecting cell lines and cell lines capable of supporting all replication phases of Human Papillomavirus.

BACKGROUND OF THE INVENTION

Human Papillomaviruses (HPVs) are widely spread small, double-stranded DNA viruses that infect epithelium of skin and mucosa. To date more than 200 different HPV types have been characterized. HPVs induce benign and malignant lesions in the epithelia, most infections are cleared by immune system. Small fraction of infections however become persistent and may give a way for development of invasive cancers. Vast majority of HPV-associated cancer cases are related to oncogenic mucosal high-risk HPVs from genus alpha (types 16, 18, 31, 33, 35, 39, 45, 51, 52, 56, 58, 59, and 68). Types 16 and 18 are most commonly associated with cervical cancers. Cervical cancer was the fourth most common cancer among women in the year 2012: there were an estimated 528,000 new cases, of which 80% are in developing countries, and 266,000 deaths. In the United States alone, 6 million new HPV cases are diagnosed every year. HPVs main oncoproteins E6 and E7 are responsible for development of malignant tumors by interfering with p53 and Rb pathways, respectively. Recently it was suggested that cutaneous HPVs infecting skin can also be associated with tumor formation, specifically non-melanoma skin cancers.

Although quite thoroughly studied, there is still no effective drug against HPV infection. Cryotherapy could be used but it has to be done several times and it is invasive. Immune system stimulants (Aldara for example) have shown moderate success rate. In addition to therapies, there are two vaccines available: Gardasil (against subtypes 6, 11, 16 and 18) and Cevarix (against subtypes 16 and 18). There are several problems with these vaccines however: they are only prophylactic and restricted to certain subtypes. Moreover, they are not available widely enough in developing countries.

HPVs infect the proliferating cells in the basal layer of epithelia and rapidly replicate their genome to an approximately 200 copies per cell upon infection. As the infected cells start to differentiate, stable maintenance phase of the replication is turned on. During this stage, viral copy number remains constant and it is replicated once per cell cycle. As the cells differentiate and reach upper levels of epithelia, vegetative HPV genome amplification occurs, during which viral copy number reaches to a few thousand copies per cell. To replicate its genome, HPVs largely depend on cellular proteins. HPVs themselves encode only two proteins essential for viral replication: E1 and E2. E1 is a DNA helicase and E2 is multifunctional protein which is, besides replication, necessary for efficient segregation of the viral genome and regulation of HPV transcription. E2 forms a complex with E1 and directs it to the site of viral replication origin.

In the recent years it has become clear that different viruses activate DNA Damage Response (DDR) to efficiently replicate their genomes. DDR is a complex cellular response to both endogenous and exogenous DNA damage, during the activation of which a large number of replication and repair proteins are located to sites of DNA damage. It has been shown that HPV activates DDR and this activation is dependent on E1 protein and replication. The exact mechanism and role of DDR in HPV replication is still unclear, however, HPV could use DDR to effectively replicate its genome. It has been shown that both ATM (Ataxia telangiectasia mutated) and ATR (ataxia telangiectasia and Rad3-related protein) pathways could be involved in different stages of HPV replication. HPV genomes go through rapid Homologous Recombination (HR; major pathway used to eliminate DNA breaks and maintain genome integrity) dependent oligomerization upon transient replication, showing that DDR is directly involved in viral genome replication. Targeting the relations between DDR and HPV is considered a promising target for developing new HPV inhibitors.

However, for targeting relations between DDR and HPV would require a model system maintaining viral replication. Since HPV replication is dependent on keratinocyte differentiation, it has been difficult to create model systems suitable for high-throughput analyses of virus replication and therefore screening chemical libraries for potential novel drug molecules. Fradet-Turcotte et al. have developed a model system where exogenous E1 and E2 expression vectors are used and the replication of HPV origin containing plasmid is monitored. This system uses luciferase as a reporter. However, this system only provides a tool to study the E1 and E2 dependent initiation of replication of the plasmid containing HPV replication origin. It does not allow monitoring of three stages of HPV genome replication. Furthermore, in this system luciferase expression is not controlled by viral promoters, and therefore it may not reflect the actual changes in the replication accurately enough.

Similar luciferase-based system useful for screening potential compounds against HPV16 E6 and E7 expression regulation and control has been also developed by Lembo et al., however it does not measure the replication of the viral genome. In addition, two other model systems have been developed based on HaCat cell line which allow to identify HPV inhibitors. One of these systems is based on the transfection of HPV11 genomes into HaCat cell line. However, HPV replication could be monitored only for a limited number of passages. Moreover, this system developed by Wang et al. lacks the high-throughput capability because it requires DNA extraction and quantitative PCR analyses The other system disclosed by Huang et al. is based on HPV VLPs that express different reporter genes. HaCat cells are infected with these VLPs and reporter gene expression could be monitored. This system, however is suitable only for identifying compounds that inhibit very early stages of HPV infection. Infection with VLPs mimics the stage of viral entry to host cell. However, no viral replication or transcription follows, therefore this system is not suitable for identifying drugs that inhibit the already established infection.

To study the replication of mucosal and cutaneous HPVs in cell culture, a U2OS based model system was developed. U.S. patent application Ser. No. 13/680,618 the contents of which is incorporated herein by reference discloses such model system. This model system is suitable for studying the initial amplification as well as stable maintenance of different HPVs. In confluent U2OS culture HPV vegetative amplification occurs as well. However, it was found that the viral replication capacity in this previously described system was lower than wt HPV genome, making the analyses difficult. Accordingly, there is a need for an improved system where the replication capability can be maintained.

SUMMARY OF THE INVENTION

A novel model system suitable for rapidly and quantitatively measure initial amplification, stable maintenance, and vegetative amplification phase of both alpha and beta papillomaviruses is provided herein. Since the system uses luciferases as reporter genes, it is suitable for high-throughput drug screening. This system is based on the U2OS cells which are suitable for studying replication of Human papillomaviruses from different phylogenetic genera. Moreover, U2OS cells can be easily and cost-effectively grown in cell culture. The gene expression of both alpha and beta papillomaviruses is very similar to that described in keratinocytes.

Provided are modified U2OS cell line (DMSZ deposit number ACC3259) that stably expresses Firefly luciferase and GFP2 proteins. These reporter genes allow to measure cell growth as well as evaluate the toxic effects of the compounds of interest. Insertion of Firefly luciferase and GFP2 do not alter the replication efficiency of HPVs in these cells.

Provided are marker genome plasmids for HPV18 (DMSZ deposit number DSM29865) and HPV5 (DMSZ deposit number DSM 29864) and HPV16. Coding sequence of *Renilla* luciferase is inserted into the ORF of E2 protein so that the expression of *Renilla* is regulated by the modulation of viral promoters. Replication abilities of these marker genomes are almost identical to the respective wt viral genomes. The expression of *Renilla* resembles the changes in the viral copy number during HPV genome replication as well. Moreover, no changes were detected in the expression of HPV18 early genes due to the insertions of *Renilla* luciferase into the ORF of E2 protein.

Accordingly, provided is a system where measuring the expression of *Renilla* luciferase can be used to evaluate the replication of HPV alpha genus (HPV18 and HPV16 as an examples) and HPV beta genus (HPV5 as an example) genome. The U2OS cells provided allow to study not only the initial amplification of various HPVs but also the stable maintenance phase and the vegetative phase.

Provided are monoclonal cell lines that stably replicate HPV18-Rluc-E2 marker genomes in an episomal form, bearing either 200 or 70 copies of viral genome per cell (DMSZ deposit numbers ACC3258, ACC3260, respectively).

Collectively, a U2OS based improved model system that uses the expression of luciferases to measure the initial amplification and stable maintenance of viral genome of alpha and beta papillomaviruses in U2OS cells is provided. This system is capable of being used to screen chemical libraries for compounds that inhibit either the initial amplification, stable maintenance, or vegetative amplification of various HPVs. The novelty of this system over any previously disclosed system lies in the fact that this system uses full-length completely functional HPV-genome. This system is capable of maintaining all the viral replication phases without fading of the replication capacity over the time.

It is an object of this invention to provide a method to screen compounds capable of inhibiting initial amplification, stable maintenance or vegetative amplification phase of Human Papillomavirus.

It is an object of this invention to provide modified U2OS cell lines capable of stable expression of HPV marker genomes in episomal form.

It is another object of this invention to provide HPV marker genomes where coding sequence of a marker gene is inserted into the ORF of E2 protein and where the expression of the marker gene is regulated by the modulation of viral promoters. The HPV virus may belong to HPV alpha group or HPV beta group. HPV 18 and HPV16 exemplifies alpha group, while HPV5 exemplifies beta group. The marker gene may be any detectable marker gene a skilled artisan would know. Such markers may be various luciferases, secreted alkaline phosphatase or various fluorescent proteins. Preferable marker gene is *Renilla* luciferase gene.

It is another object of this invention to provide novel U2OS cell lines deposited with DMSZ accession numbers DSM ACC3258, DSM ACC 3259 and DSM ACC3260.

It is yet another object of this invention to provide HPV marker genome plasmids deposited with DMSZ with deposit numbers DSM 29864 and DSM 29865 and having the nucleic acid sequence according to SEQ ID NO:1 and SEQ ID NO:3; respectively.

In one aspect of the invention it is disclosed an extrachromosomally maintainable plasmid for transfecting human osteosarcoma cell lines supporting all phases of HPV DNA replication, said plasmid comprising a complete or partial coding sequence of a marker gene inserted into the ORF of E2 protein whereby the expression of marker gene is regulated by the modulation of viral promoters.

In another aspect of the invention it is disclosed an extrachromosomally maintainable plasmid for transfecting human osteosarcoma cell lines supporting all phases of HPV DNA replication, said plasmid comprising a complete or partial coding sequence of *Renilla* luciferase gene inserted into the ORF of E2 protein whereby the expression of marker gene is regulated by the modulation of viral promoters.

In one aspect of the invention it is disclosed an extrachromosomally maintainable plasmid for transfecting human osteosarcoma cell lines supporting all phases of HPV DNA replication, said plasmid comprising a complete or partial coding sequence of *Renilla* luciferase gene inserted into the ORF of E2 protein of a HPV belonging to alpha group or beta group, whereby the expression of marker gene is regulated by the modulation of viral promoters.

In one aspect of the invention it is disclosed an extrachromosomally maintainable plasmid for transfecting human osteosarcoma cell lines supporting all phases of HPV DNA replication, said plasmid comprising a complete or partial coding sequence of *Renilla* luciferase gene inserted into the ORF of E2 protein of a HPV5, HPV16 or HPV 18, whereby the expression of marker gene is regulated by the modulation of viral promoters.

In one aspect of the invention a plasmid having nucleic acid sequence SEQ ID NO:1, SEQ ID NO3, or 42 is disclosed.

In one aspect of the invention is a HPV marker genome according to SEQ ID NO:4, SEQ ID NO:2 or SEQ ID NO:43.

In one aspect of the invention is a detectable fusion peptide comprising SEQ ID NO:16, SEQ ID NO:17 or SEQ ID NO:35.

In one aspect a monoclonal human osteosarcoma cell line DSM ACC3258 enabling initial replication, stable maintenance and vegetative amplificational replication of HPV DNA is disclosed.

One aspect of the invention is a monoclonal human osteosarcoma cell line DSM ACC3258 transfected with a plasmid having nucleotide sequence according to SEQ ID NO: 1, SEQ ID NO: 3, or SEQ ID NO:42.

Another aspect of the invention is a monoclonal human osteosarcoma cell line with deposit number DSM ACC 3260 or DSM ACC 3259.

One aspect of the invention is a method for identifying compounds capable of inhibiting Human Papilloma Virus replication at initial replication phase, stable maintenance phase or at vegetative amplification phase, said method comprising the steps of: a) Providing the cell line with accession number ACC 3258; b) Transfecting the cell line with the extra chromosomally maintainable plasmid comprising a complete or partial coding sequence of a marker gene inserted into the ORF of E2 protein whereby the expression of the marker gene is regulated by modulation of viral promoters) Obtaining a stable cell line expressing an HPV marker genome comprising marker gene and HPV genome; d) Providing a monolayer cultivation of the obtained cell; e) Applying a compound under investigation on the monolayer of step d); f) assessing a presence or an absence of inhibitory effect of the compound on viral DNA maintenance or amplification in the cells; wherein presence of inhibitory effect of the compound results in classification of the compound as a replication inhibitor candidate.

Another aspect of the invention is a method for identifying compounds capable of inhibiting Human Papilloma Virus (HPV) replication at initial replication phase, stable maintenance phase or at vegetative amplification phase, said method comprising the steps of: a) Providing a monolayer cultivation of stable U2SO cell line ACC 3260 or ACC 3259 enabling initial replication, stable maintenance and vegetative amplificational replication of the HPV DNA; b) applying a compound under investigation to the monolayer of step a); c) assessing a presence or an absence of inhibitory effect of the compound on viral DNA maintenance or amplification in the cells; wherein presence of inhibitory effect of the compound results in classification of the compound as a replication inhibitor candidate.

One aspect of the invention is a kit for identifying compounds capable of inhibiting HPV replication at initial replication, stable maintenance or vegetative amplificational phase, said kit comprising: a) Human osteosarcoma cell line having accession number ACC3258, b) An extra chromosomally maintainable plasmid comprising, a complete or partial coding sequence of a marker gene inserted into the ORF of E2 protein, whereby the expression of the marker gene is regulated by the modulation of viral promoters, c) Instructions to transfect the cell line of step a) with plasmid of step b); d) a compound or a library of compounds to be screened for anti-HPV activity; and f) a means, for quantitative assessment of replicational, transcriptional or translational activity of HPV DNA in the cells.

One aspect of the invention is a kit for identifying compounds capable of inhibiting HPV replication at initial replication, stable maintenance or vegetative amplificational phase, said kit comprising: a) human osteosarcoma cell line U2OS having accession number ACC3260, or DSM ACC 3259; b) a compound or a library of compounds to be screened for anti-HPV activity; and c) a means for quantitative assessment of replicational, transcriptional or translational activity of HPV DNA in the cells.

#10.15 cells were transfected with 2 ug of HPV18 wt, HPV18-Rluc-E2 genomes. The low-molecular-weight DNA was extracted 48, 72 and 96 hours after the transfection, linearized and bacterially produced input DNA was digested with DpnI. The Southern Blot analyses were carried out to measure replication properties of HPV18 wt (lanes 1-3) and HPV18-Rluc-E2 (lanes 4-6). Replicated HPV18 DNA is shown by arrow. Lane 7 serves as size marker.

Figure 7:
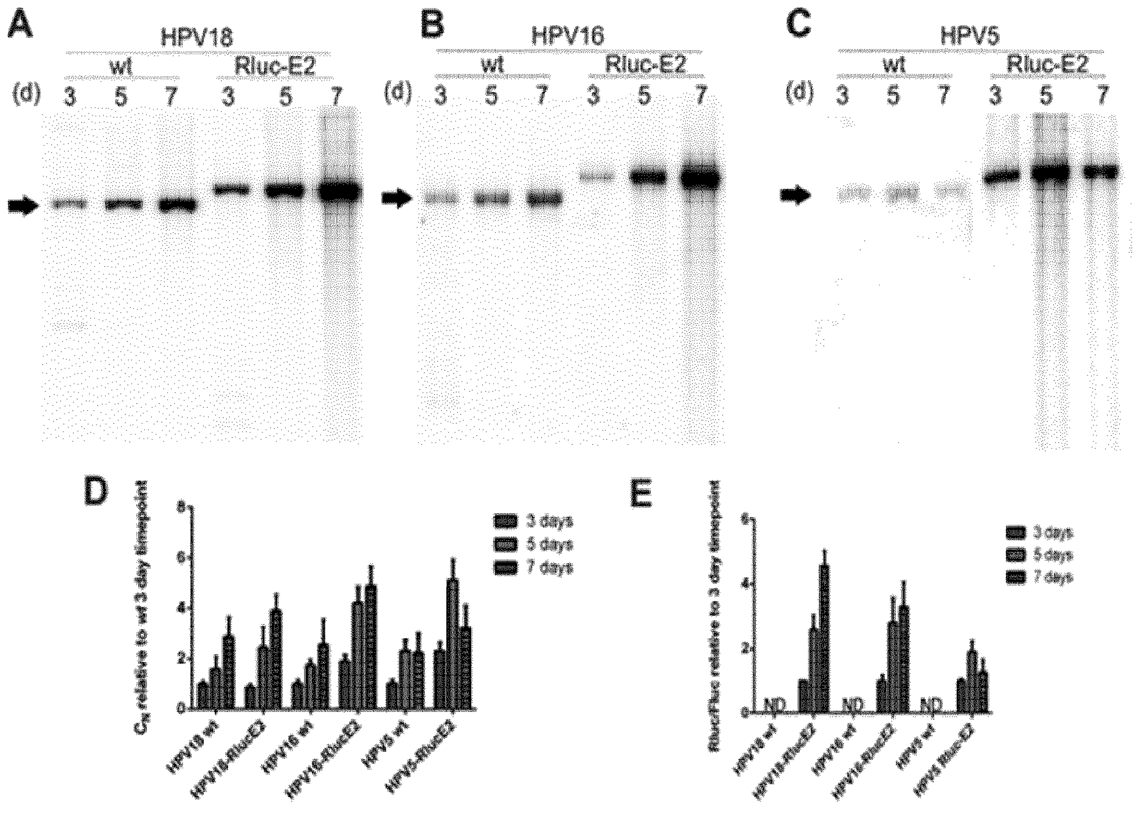

FIG. 7. Analysis of the transient replication of HPV18, HPV5 and HPV16 marker genome in U2OS GFP2-Fluc #10.15 cell line. U2OS #10.15 cells were transfected with 2 ug of HPV18 wt, HPV18-Rluc-E2, HPV5 wt, HPV5 Rluc-E2, HPV16 wt and HPV16-RlucE2 genomes. A-C: The genomic DNA was extracted 3, 5 and 7 days after the transfection, linearized and bacterially produced input DNA was digested with DpnI. Replication signals were visualized by Southern Blot analyses. D: The replication signals from the same experiments were quantified by qPCR analyses and are expressed relative to the signals obtained from either HPV18, HPV16 or HPV5 wt 3 day time point. E: Both *Renilla* (from HPV marker genomes) and Firefly (from U2OS genome) was measured in dual-luciferase assay and is expressed as Rluc/Fluc ratio. Signals are expressed relative to the values obtained from either HPV18-RlucE2, HPV16-RlucE2 or HPV5-RlucE2 3 day time point. HPV18, HPV16 and HPV5 wt serve as negative controls for *Renilla* expression. In both panels D and E, average values with standard deviations from two independent experiments are shown.

Figure 8:
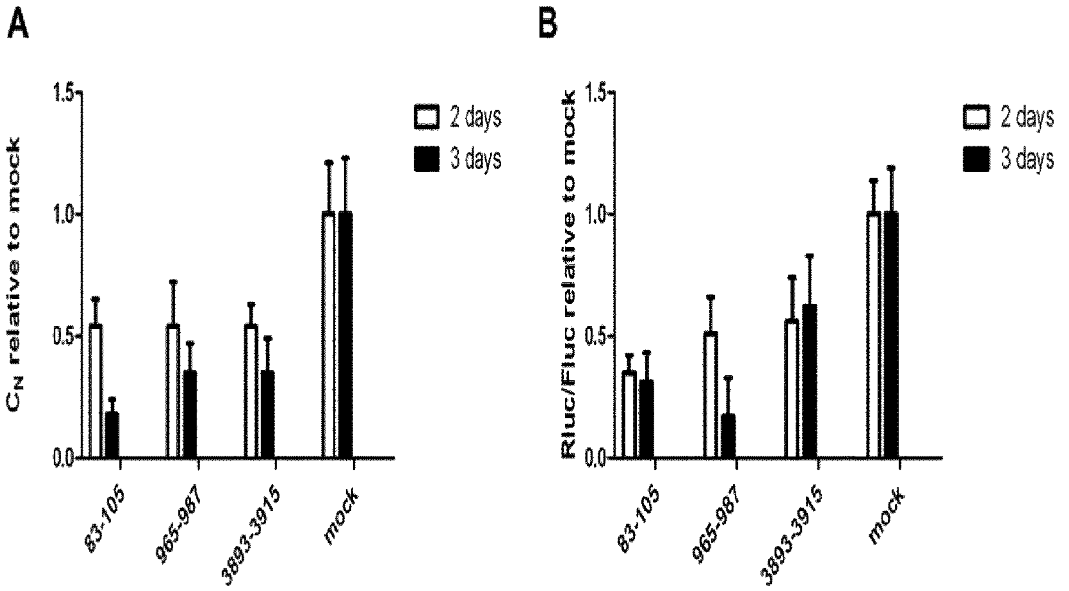

FIG. 8. The expression of *Renilla* luciferase from HPV18-Rluc-E2 genome resembles the changes in the viral copy number. U2OS #10.15 cells were co-transfected with 2 ug of HPV18-Rluc-E2 marker genome and 500 pmol of different siRNAs. A: The genomic DNA was extracted 3 and 5 days after the transfection, linearized and bacterially produced input DNA was digested with DpnI. Replication signals were quantitated by qPCR. The relative numbers are obtained by normalizing the data points to the same time-point data of of HPV18-RlucE2 marker genome transfected alone (mock). B: Both *Renilla* (from HPV marker genome) and Firefly (from U2OS genome) were measured in dual-luciferase assay and is expressed as Rluc/Fluc ratio. The relative numbers are obtained by normalizing the data points to the same time-point data of HPV18-RlucE2 marker genome transfected alone (mock). In both panels average values with standard deviations from two independent experiments are shown.

Figure 9:
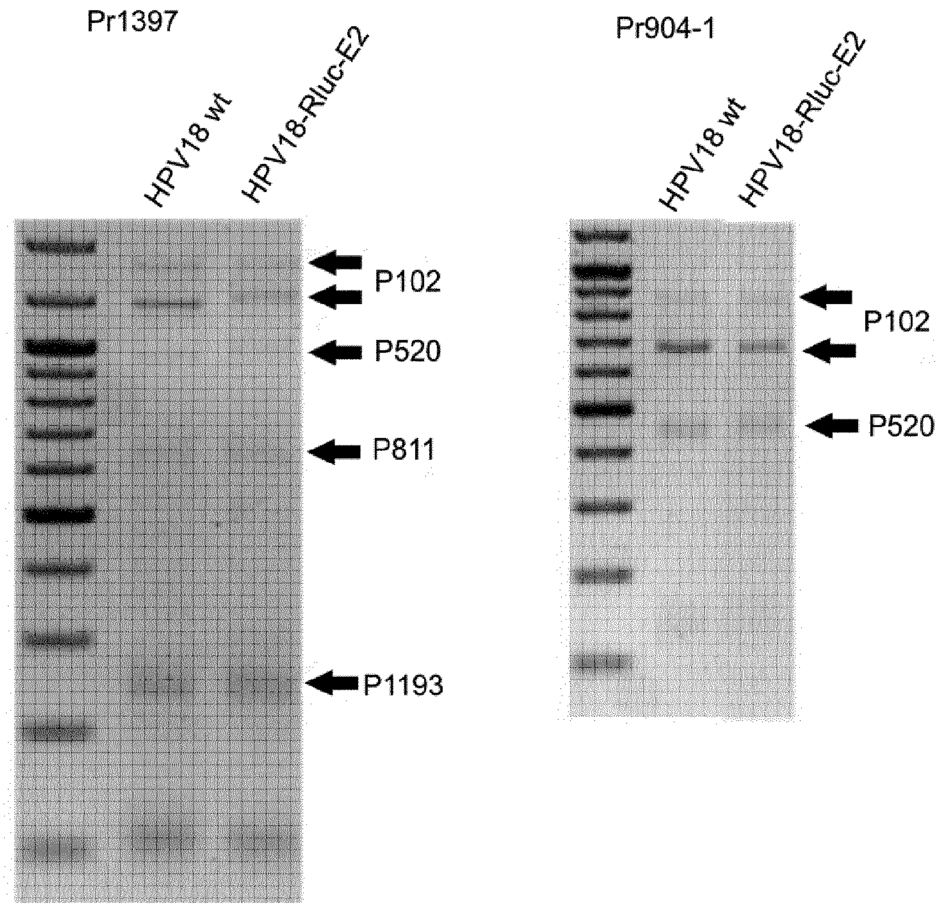

FIG. 9. Comparative transcription map analysis of the HPV18-RlucE2 and wt HPV18 in U2OS cells. PolyA+ RNA templates were extracted from U2OS cells that had been transfected with 500 ng of the wt HPV18 genome or with the HPV18-RlucE2 (72 h time-point). 500 ng of the polyA+ RNA was used as a template 5'RACE with HPV18-specific primers Pr1397 (binds to E1 ORF) and Pr904-1 (binds to E7 ORF). Promoter regions, from which the detected transcripts arisen, are indicated by arrows on the right.

Figure 10:
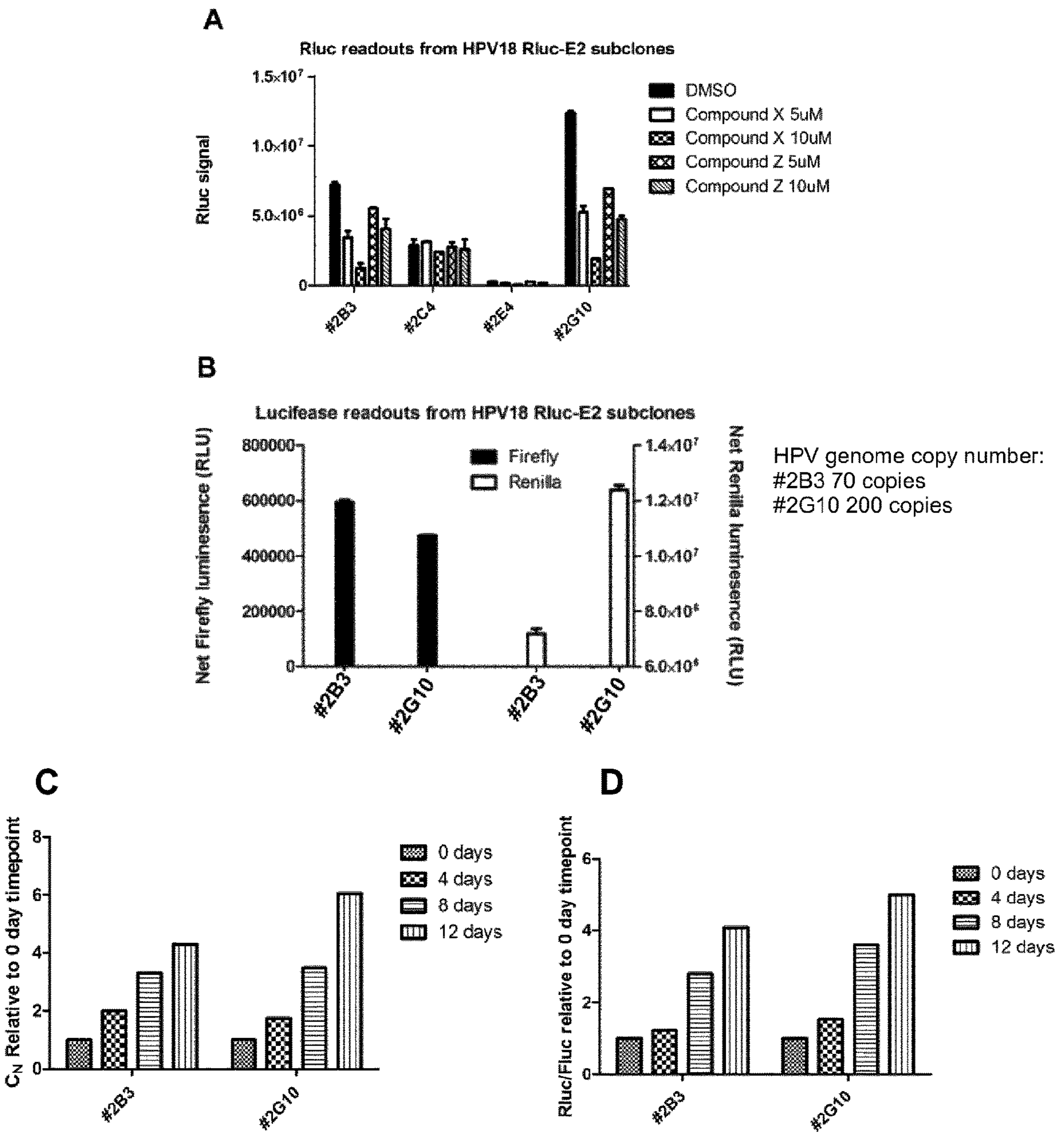

FIG. 10. Analyses of monoclonal U2OS #10.15 cell lines stably maintaining HPV18-Rluc-E2 marker genome. A. Cell lines #2B3, #2C4, #2E4 ad #2G10 were grown in subconfluent conditions in the presence of two HPV-specific inhibitors (compound X and compound Z) for 6 days. DMSO serves as vehicle control. *Renilla* luciferase readouts were measured to evaluate changes in the viral copy number in the monoclonal cell liness. B: The expression of *Renilla* and Firefly luciferases from two clones of U2OS #10.15 cells stably replicating HPV18-Rluc-E2-genome: #2B3 (deposited with DMSZ deposit number ACC3259) and #2G10 (deposited with DMSZ deposit number ACC3260). The expression of *Renilla* (right axis) and Firefly (left axis) luciferases from two clones of U2OS #10.15 cells stably maintaining episomal HPV18-Rluc-E2 genome: #2B3 and #2G10, measured on two different days. *Renilla* expression resembles differences in HPV18-Rluc-E2 copy number in these cell lines. Firefly expression resembles the growth of cells. Viral copy numbers are indicated. C and D: To measure the late amplification, the cells were seeded onto 6-well plates and grown for indicated days without splitting. C: To measure viral replication the genomic DNA was extracted 0, 4, 8 and 12 days after seeding the cells, linearized and quantitated by qPCR. Replication signals obtained from either subclones are expressed relative to the signals obtained from the respective 0 day time point. D: Both *Renilla* (from HPV18 marker genome) and Firefly (from U2OS genome) levels from the same experiment were measured in dual-luciferase assay and the values obtained from either subclones are expressed relative to the signals obtained from the respective 0 day time point.

DETAILED DESCRIPTION OF THE INVENTION

Definitions

Initial replication or transient replication refers to HPV DNA replication at establishment of the infection.

Stable maintenance or latent maintenance refers to the latent stage of viral replication cycle where viral DNA is stably maintained at an almost constant copy number in dividing host cells.

Vegetative amplificational replication or late amplificational replication refers to exponential viral DNA amplification when epithelial cells detach the basement membrane.

Marker genome refers to full or partial HPV genome which in addition to all viral proteins expresses easily detectable and quantifiable marker gene.

The present invention provides a method for identifying compounds capable of inhibiting Human Papillomavirus (HPV) DNA replication as well as plasmids for transfecting cells, cell lines capable of supporting all phases of HPV DNA replication and a kit for identifying the compounds capable of inhibiting HPV DNA replication.

An improved method for HT-screening is disclosed. Also improved plasmids suitable for the screening system, as well as monoclonal cell lines suitable for maintaining the viral replication in all the replication phases are disclosed here.

An improved model system is disclosed that can be used for high-throughput screening for anti-HPV compounds for HPV initial amplification, stable maintenance and vegetative amplification. The system uses U2OS cells expressing GFP2 and Firefly luciferase (U2OS-GFP2-Fluc #10.15) to assess the toxicity of the compound and mucosal HPV18 or cutaneous HPV5 genomes expressing *Renilla* luciferase to measure the changes in the viral copy number. *Renilla* luciferase is inserted into the open reading-frame of E2 protein and it is expressed using viral promoters. This marker genome replicates similarly to the wt HPV genome and therefore can be used, together with U2OS-Fluc cell line, for high-throughput screening for potential HPV replication inhibitors. In addition, generated monoclonal cell lines based on U2OS-GFP2-Fluc #10.15 are disclosed stably replicating episomal HPV18Rluc-E2 genome with various copy numbers. These cell lines are suitable for screening compounds inhibiting HPV stable replication.

Designing Principles of HPV Marker Genomes M-E2

The development of effective anti-HPV drugs has been strongly hampered by very limited availability of appropriate cell-based assay systems. In the U.S. patent application Ser. No. 13/680,618 we disclosed a cell-based assay for selection of anti-HPV drugs using U2OS cells In developing the assay the goal was to have an assay that would:

i) allow for modelling of different stages of viral replication;

ii) support the replication of many different types of HPVs (mucosal and cutaneous);

iii) may be immortalised and cultivated in conditions suitable for automated high-throughput screening of chemical compound libraries.

Figure 1:
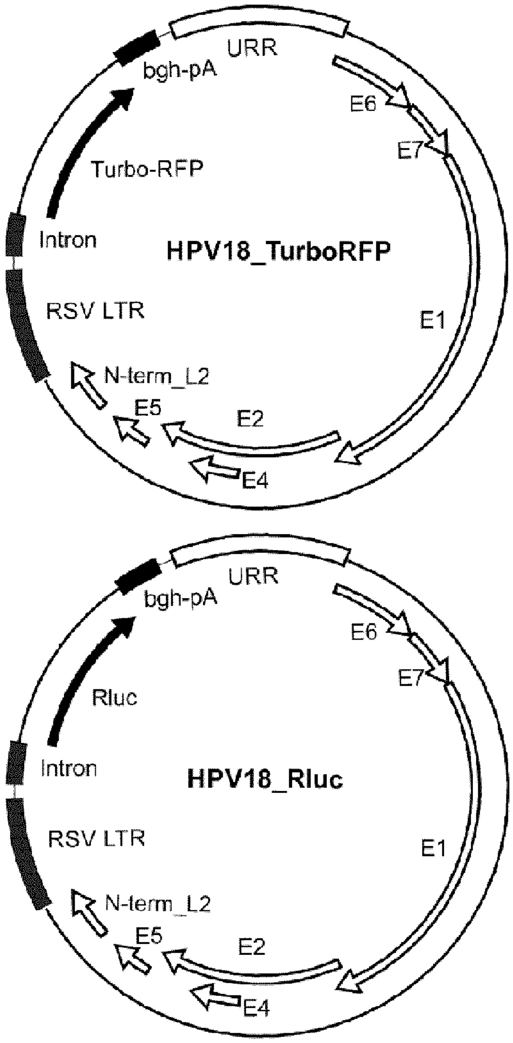
FIG. 1. Schematic map of a first generation marker genome. Non-HPV regions are marked in black. The sequences of the plasmids are according to SEQ ID NO: 5 for HPV18_TurboRFP; SEQ ID NO: 6 for HPV18_RFP; SEQ ID NO:7 for HPV18_Rluc and SEQ ID NO:8 for HPV18_Gluc.
Figure 2:
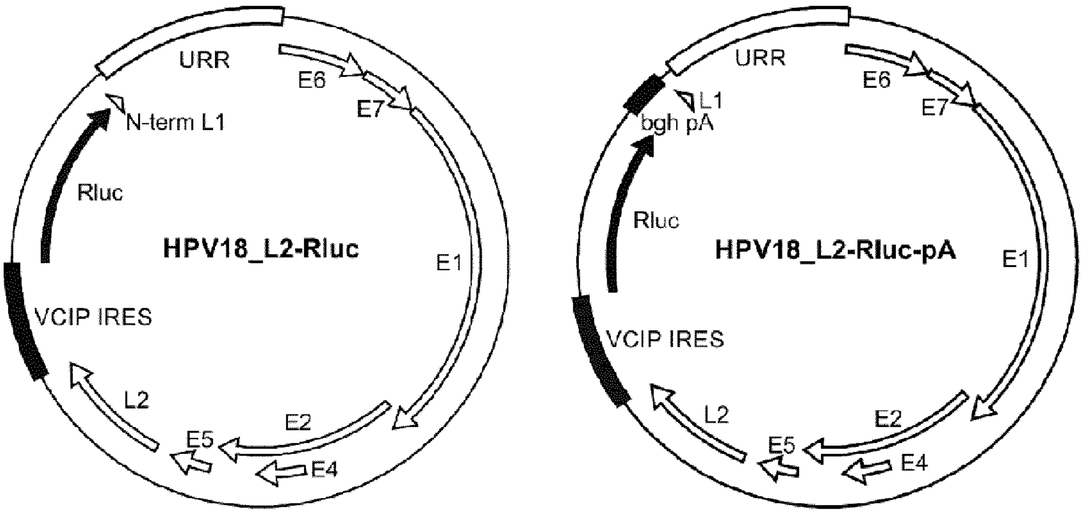
FIG. 2. Schematic maps of the $2^{nd}$ generation marker genomes (disclosed in U.S. Ser. No. 13/680,618). The sequences of the plasmids are according to SEQ ID NO: 9 for HPV18_L2-Rluc and SEQ ID NO:10 for HPV18_L2-Rluc-pA.

Thus, for automated, high-throughput measurement of the changes in viral genome copy number (replication), the goal was to introduce suitable detectable marker genes into the HPV genomes (for making marker genomes) without compromising their ability to replicate. Based on literature data, initial attempts were related to replacement or adding marker genomes into the late region (capsid protein genes) of the HPV genome as the region is not needed for replication. These first and second generation marker genomes are shown in FIGS. 1 and 2 and described below:

Design and Construction of the $1^{st}$ Generation Marker Genomes by Replacing HPV18 Late L1 and L2 Encoding Region with RSV LTR Driven Marker Genes It has been demonstrated that subgenomic ("early") fragment of HPV-18 lacking part of the genome encoding the L1 and L2 has full replication capacity in U2OS cells. Thus, initially the viral marker genomes (1" generation) were designed by replacing late L1 and L2 encoding region with different expression marker genes (*Renilla* luciferase, Rluc; *Gaussia* luciferase, Gluc; Red Fluorescent Protein, RFP; and destabilised RFP, TurboRFP-dest1) driven by the Rous Sarcoma Virus (RSV) LTR promoter (FIG. 1) The plasmids were constructed using pMC backbone so that marker genomes without bacterial backbone can be produced as minicircle plasmids during propagation in *E. coli* cells. Plasmids are schematically shown in FIG. 1 and have nucleotide sequences SEQ ID NO: 5, 6, 7 and 8.

Figure 3:
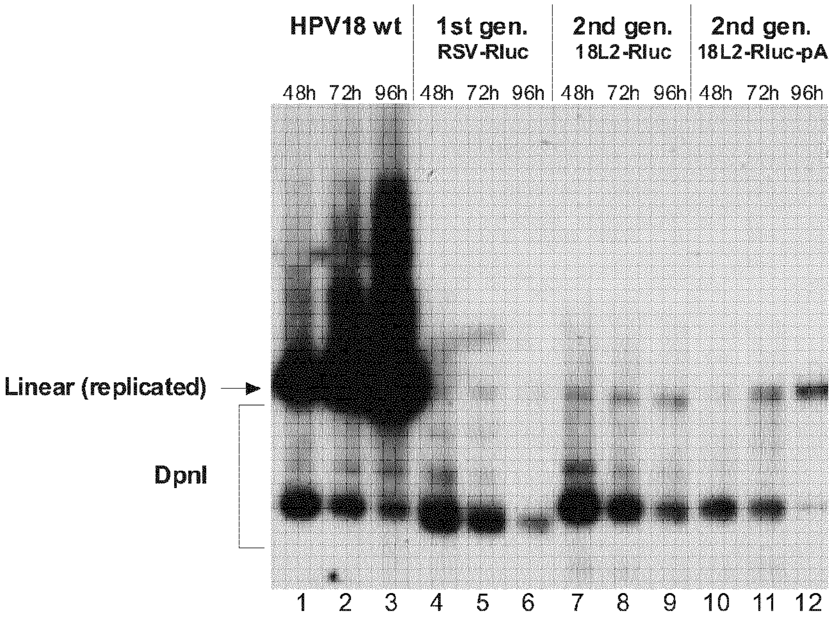
FIG. 3 Analysis of the replication properties of the first and second generation marker genomes in U2OS-GFP2-Fluc #10.15 cells. The cells were transfected with 1 μg of wt HPV18 genome or with 1 μg of marker genomes as indicated on the top. The replication signals were analysed from low-molecular weight DNA at 48, 72 and 96 hours after transfection using. DpnI digestion and Southern blotting with HPV18 early region specific probe.

Analysis of the replication properties of the $1^{st}$ generation marker genomes For analysis of the replication properties the marker genomes were transfected into U2OS-EGFP-Fluc #10.15 cells and low molecular weight DNA was collected from the cells (time-points 48, 72 and 96 hours), digested with the restriction endonuclease linearizing the HPV18 genome and with DpnI (destroys the unreplicated input plasmid). The digested DNA samples were analysed by Southern blotting using early region of the HPV18 genome as the probe. The results shown on the FIG. 3 demonstrate the loss of replication capability of the 1st generation marker genome (lanes 4-6) compared to wt HPV18 genome (lanes 1-3). Similar phenomenon was observed using marker genomes expressing Gluc or red fluorescent proteins and also in wt U2OS cells.

Design and Construction of the $2^{nd}$ Generation Marker Genomes by Replacing Part of the Late Region with VCIP IRES Driven Marker Gene Based on the weakened replication capacities of the $1^{st}$ generation marker genomes we designed and constructed the $2^{nd}$ generation marker genome expressing the Rluc. The plasmids are schematically shown in FIG. 2 and have nucleotide sequences SEQ ID NO: 9 and SEQ ID NO: 10, respectively. This design was based on a fact that early fragment of the HPV18 genome can replicate as complete genome and on the knowledge that 1" generation marker genomes lost their replication capability by expression cassette insertion into the late region. In addition, HPV transcription map in U2OS cells was constructed by RACE analysis and it showed very complex transcription/splicing processes of the viral genome. Therefore, it was hypothesized that including transcription regulatory elements (like RSV LTR) into the HPV genome may interfere the viral transcription events and thereby supress the replication. The mapping of the viral transcriptome also indicated that late region (especially L2 ORF) including transcripts are present in all phases of the viral replication. Moreover, the level of the L2 transcript well correlates with the viral copy number in the host cells. Thus, we designed the $2"^{d}$ generation marker genomes by introducing the marker gene into the L2 ORF so that elements necessary for correct polyadenylation of the early transcripts (native polyadenylation signal in the beginning of the E2 ORF and ~680 nt downstream from this) remain intact. Full length VCIP IRES element that has been demonstrated being active in U2OS cells, was added in front of the Rluc marker gene to promote its translation. Two variants of the $2^{nd}$ generation marker genome were constructed that differ in the absence or presence of the heterologous polyadenylation region after Rluc coding sequence (18L2-Rluc, 18L2-Rluc-pA, are shown in FIG. 2).

Analysis of the Replication Properties of the $2^{nd}$ Generation Marker Genomes The properties of the $2^{nd}$ generation marker genomes were analysed as described above in section "Analysis of the replication properties of the $1^{st}$ generation marker genomes". The results shown on FIG. 3 (lanes 7-12) demonstrate that despite the slight improvement of the replication capability of $2^{nd}$ generation marker genomes, especially 18L2-Rluc-pA (lanes 10-12) compared to the $1^{st}$ generation, the marker genomes have replication capacities still much weaker than wt HPV18 has (lanes 1-3).

The analyses showed that although the late region can be removed without significant reduction of replication, the replacements in the HPV late region eventually decreased the viral replication capability.

Due to this unexplained fading of replication capacity in the previous system there was a need to re-design the marker genomes. The new approach was to insert the marker gene into the viral early region between the E1 ORF and E2 ORF. As these ORFs are absolutely needed for replication, it was reasoned that their transcription level should reflect the viral copy number as well. The level of E1 mRNA increases during initial amplification of the HPV18 genome as well as during final vegetative amplification in U2OS cells. During HPV5, 16 and 18 genome replication, the mRNA comprising both E1 and E2 ORFs is produced and at least in HPV18, the level of the mRNA increases during initial amplification of the HPV genome as well as during final vegetative amplification of in U2OS cells.

Figure 4:
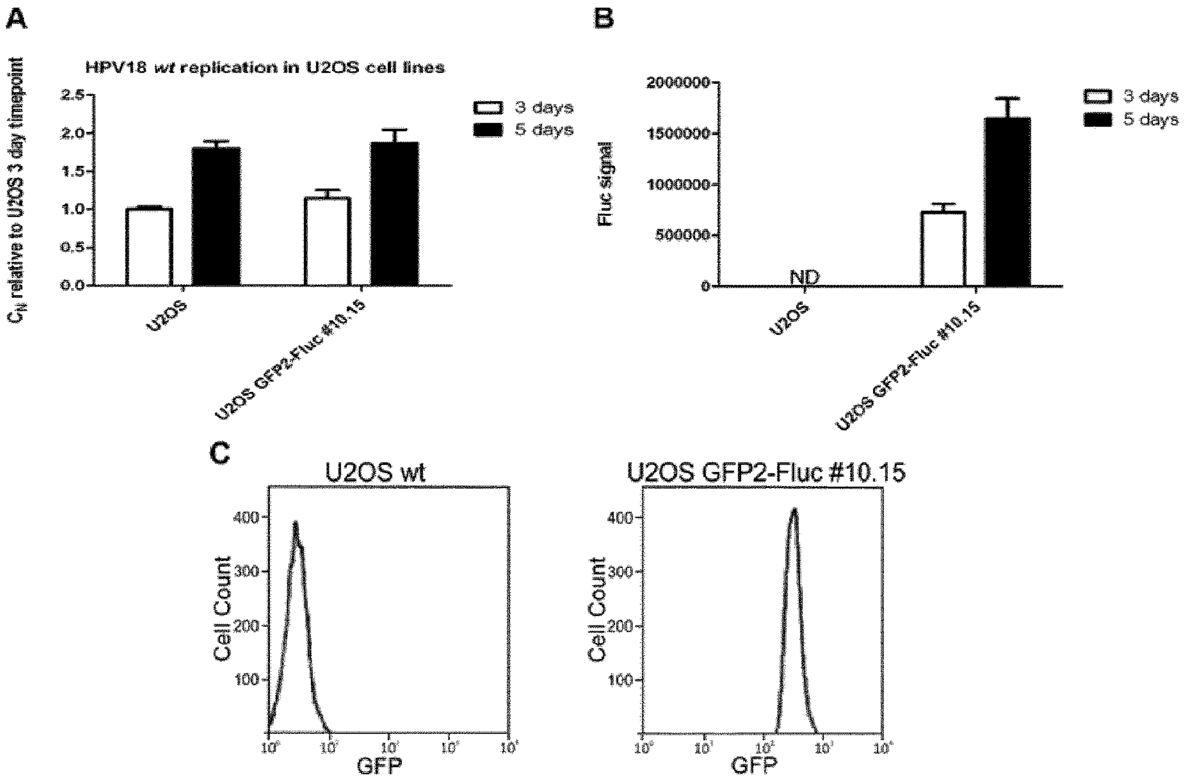
FIG. 4. Description of the modified U2OS GFP2-Fluc #10.15 cell-line. A: U2OS GFP2-Fluc #10.15 cell-line is suitable for studying the replication of HPVs. The U2OS wt or #10.15 cells were transfected with 2 μg of wt HPV18 minicircle genome. The genomic DNA was extracted 3 and 5 days after the transfection, digested with BglI to linearize HPV18 genome and with DpnI to eliminate bacterially produced input DNA. Replication signals were quantitated by qPCR and are expressed relative to U2OS 3 day timepoint as described in materials and methods section B: Firefly luciferase expressed from the U2OS GFP2-Fluc #10.15 resembles cell growth. 150 000 U2OS wt or #10.15 cells were seeded onto 6-well plates and grown for 3 and 5 days. Fluc levels were measured and are expressed relative to 3 days timepoint of #10.15 cells. U2OS wt serves as negative control. C: Flow cytometry analyses of U2OS wt and #10.15 showing homogenous and clearly detectable GFP signal for U2OS #10.15. U2OS wt serves as negative control. Error-bars indicate the standard deviations from two independent experiments. Cell growth and viability could be evaluated by the reporter genes Firefly luciferase and GFP expression.

In HPV genomes the 3' end of E1 ORF and 5' end of E2 ORFs overlap. In designing novel plasmids, the marker gene cDNA was inserted between E1 and E2 ORFs so that a fusion polypeptide expressed starts from native start codon of the E2. The resulting fusion polypeptide has N-terminal part of E2 encoded by part of E2 ORF that is overlapped with E1 ORF and it is fused with Rluc protein with C-terminal FMDV 2A peptide and full-length E2 protein starting from initiating methionine. During translation the 2A peptide induces the "skip" of ribosome (PG↓P) resulting "cleavage" of the polypeptide into two final protein products: N-terminal part of E2-marker-2A (without terminal proline) (SEQ ID NO: 17 in case of HPV5, and SEQ ID NO:16 in case of HPV18) and native E2 protein with additional proline at N-terminus (FIG. 4). The first product, E2-marker- 2A (SEQ ID NO:16 or SEQ ID NO:17), possesses detectable signal. In this configuration no replacements are made in the late region and no transcription regulatory elements are included which could interfere the normal regulation of complex transcription patterns of HPV genome.

Using the principle described above, *Renilla* luciferase (Rluc) expressing marker genomes were generated for mucosal HPV18 and for cutaneous HPV5.

The HPV marker genomes were constructed and propagated using minicircle production plasmid pMC.BESBX disclosed by Kay et al. The pMC.BESBX contains bacterial origin of replication and kanamycin resistance gene that are needed for propagation in bacterial cells. In addition, it contains additional elements that allow produce the HPV marker genomes as minicircle plasmids in *E. coli* minicircle producer strain ZYCY10P3S2T as almost no bacterial backbone present in the final product. So, the resulting plasmid successfully mimics the organisation of authentic viral genome.

Novel plasmids, cell lines and method to screening are now described below.

Cloning of HPV Marker Genomes

HPV18 Marker Genome HPV18-RlucE2

The HPV18 marker genome HPV18-RlucE2 (SEQ ID NO:4) was generated in accordance with above described principles. The length of overlapping region between 3' end of E1 ORF and 5' end of E2 ORFs in HPV18 is 71 nt (nt 2818-2887); the HPV18 numbering herein and below is from GenBank accession no. NC_001357.1). Rluc encoding cDNA (from pRL-TK, Promega) with C-terminal 2A sequence of FMDV (SEQ ID NO:11) was inserted between E1 and E2 ORFs (SEQ ID NO 12 and SEQ ID NO:14 respectively). This resulted the novel ORF of single polypeptide that starts from native start codon of the E2. The 724 aa polypeptide (SEQ ID NO:16) consists of:

(i) 24 N-terminal amino acids of HPV18 E2 encoded by part of E2 ORF that is overlapped with E1 ORF (SEQ ID NO:18)

(ii) single Ala residue (A) followed with (iii) Rluc protein starting from the second amino acid (SEQ ID NO:19) followed with (iv) FMDV 2A peptide (SEQ ID NO:20) followed with (v) full-length HPV18 E2 protein starting from initiating methionine (SEQ ID NO:21).

It is processed co-translationally into two final products:

(i) Rluc protein that fused with 24 N-terminal aa of HPV18 E2+Ala at its N-terminus and with FMDV 2A peptide at its C-terminus (SEQ ID NO:22); and (ii) full-length HPV18 E2 protein containing additional Pro at N-terminal end) (SEQ ID NO:23).

Cell Lines and Transfection

U2OS cells, which were obtained from the American Type Culture Collection (ATCC no: HTB-96), the modified U2OS GFP2-Fluc #10.15 and the HPV18 Rluc-E2-positive U2OS #10.15 subclones #2G10 and #2B3 were grown in Iscove's modified Dulbecco's medium (IMDM) supplemented with 10% fetal calf serum (FCS). U2OS cells were transfected with the indicated amounts of different HPV miniplasmids or 500 pmol of HPV18 specific siRNA-s by electroporation (220 V, 975 μF) with a Bio-Rad Gene Pulser II that was supplied with a capacitance extender (Bio-Rad Laboratories). U2OS GFP2-Fluc #10.15 cell line was generated by transfecting U2OS cells with the linearized expression vector containing both GFP2 and Firefly luciferase (Flue) ORFs as well as resistance gene of Puromycin. Individual Puromycin resistant clones were picked and analysed by GFP and Flue expression. HPV18 Rluc-E2 positive subclones were generated as described below.

Plasmids

The parental plasmid pMC-HPV18 was constructed for the production of HPV18 genome miniplasmids. A recognition site for the BglII restriction endonuclease was introduced into the HPV18 genome between nt 7473 and nt 7474 (herein, the numbering of the HPV18 genome is according to the NCBI Reference Sequence NC_001357.1). These sites were used previously without observing changes in the gene expression compared to unaltered HPV18.

The modified HPV18 genome was cloned into the minicircle production plasmid pMC.BESBX. The pMC backbone derived from pMC.BESBX permits the production of the HPV18 genome from pMC-HPV18 as a supercoiled minicircle that contains 92 bp long non-HPV sequence. Miniplasmid production was performed in *E. coli* strain ZYCY10P3S2T according to a previously published protocol. Briefly, pMC-HPV18 containing *E. coli* strain ZYCY10P3S2T was grown in Terrific Broth media (Life Technologies) at 37° C. for 16-18 h. Next, equal amount of LB media containing 0.02% L-arabinose and 20 mM NaOH was added and culture was grown at 32'C for 8 hours to induce recombination and production of supercoiled minicircles. Finally, the HPV18 genomes were purified from *E. coli* with the QIAfilter Plasmid kit (Qiagen). The HPV18 Rluc-E2 markergenome was constructed by adding the Rluc encoding cDNA (from pRL-TK, Promega) with C-terminal 2A sequence of FMDV was inserted between E1 and E2 ORFs The length of overlapping region between 3' end of E1 ORF and 5' end of E2 ORFs in HPV18 is 71 nt (nt 2818-2887). This resulted the novel ORF of single polypeptide that starts from native start codon of the E2 (SEQ ID NO:16).

The HPV5 marker genome HPV5-RlucE2 (SEQ ID NO: 2) was generated by the way similar to HPV18. The length of overlapping region between 3' end of E1 ORF and 5' end of E2 ORFs in HPV5 is 59 nt (nt 2723-2781); the HPV5 numbering herein and below is according to GenBank accession no. NC 001531.1). The Rluc encoding cDNA with C-terminal 2A sequence of FMDV (SEQ ID NO:11) was inserted between E1 and E2 ORFs. This resulted the novel ORF of fusion polypeptide that starts from native start codon of the E2 (SEQ ID NO:17).

The HPV16 marker genome HPV16-RlucE2 (SEQ ID NO: 43) was generated by the way similar to HPV18. The length of overlapping region between 3' end of E1 ORF and 5' end of E2 ORFs in HPV16 is 59 nt (nt 2723-2781); the HPV16 numbering herein and below is according to GenBank accession no. K02718.1. The Rluc encoding cDNA with C-terminal 2A sequence of FMDV (SEQ ID NO:11) was inserted between E1 and E2 ORFs. This resulted the novel ORF of fusion polypeptide that starts from native start codon of the E2 (SEQ ID NO: 35).

Transient Replication Assay, HPV Copy Number Quantitation, and Measurement of Firefly and *Renilla* Luciferases Transient replication assay: Low-molecular-weight DNA was extracted by Flirt lysis protocol. Cells were lysed in 0.8 ml HIRT lysis solution (0.5% SDS, 50 mM Tris, pH 8.0, and 10 mM EDTA) for 15 minutes at room temperature. 200 ul of 5M NaCl was added and samples were stored at 4'C overnight. Next, the samples were centrifuged at 16 000 g for 15 minutes, supernatant was transferred to a new tube and DNA was precipitated with 0.6 volumes of isopropanol. The samples were treated with proteinase K at 56 C for 30 minutes and DNA was separated with phenol-chloroform extraction. Next, the DNA was precipitated, redissolved in TE containing 20 ug/ml RNase A and incubated at 37° C. for one hour. Next, DNA was digested with BglI for linearization and DpnI to distinguish between transfected and replicated HPV18 DNA, resolved on an 0.8% agarose gel, blotted, and hybridized with an HPV18 genome sequence-specific probe labelled with [$\alpha$-$^{32}$P]dCTP using random priming (DecaLabel kit; Thermo Scientific). Specific HPV replication signals were detected by exposure to X-Ray films (AGFA).

HPV Copy Number Quantitation:

The viral genome copy number in U2OS cells during replication was analysed by quantitative real-time PCR (qPCR). Genomic DNA was extracted from U2OS cells that had been transfected with 2 μg of the HPV miniplasmids at 3, 5 and 7 days after the transfection. The samples were linearized by digestion with BglI (Thermo Scientific), and the bacterially produced input DNA was fragmented by digestion with DpnI (Thermo Scientific). For each qPCR reaction, 3 ng of DNA was used, and the reactions were performed with EvaGreen qPCR Mix Rox (Solis BioDyne) according to the manufacturer's protocol on a 7900 HT Fast Real-Time PCR System (Applied Biosystems). The HPV18 replication signal was amplified with the following oligonucleotides (300 nM of each per reaction): 5'-GCGCTTT-GAGGATCCAAC-3' (SEQ ID NO: 24) and 5'-GTTCCGTGCACAGATCAG-3' (SEQ ID NO:25). The HPV 5 replication signal was amplified with the following oligonucleotides: 5'-GGTTGCAGGAACTGTGAGGT-3' (SEQ ID NO: 26) and 5'-TCCGCGACAGTCGGGGCACAGG-3' (SEQ ID NO: 27). For HPV16 the oligonucleotides were: 5'-CC-CACAGCTACAGATACAC-3' (SEQ ID NO: 40) and 5'-GCAGGTGTGGTATCAGTTG-3' (SEQ ID NO:41). The analysis was performed according to the comparative threshold cycle ($\Delta$Ct) method. The results were calculated from the PCR cycle number in which the HPV signal exceeded the threshold value ($Ct_{HPV}$). The $Ct_{rDNA}$ was detected as a normalization standard from the ribosomal DNA gene sequence in the U2OS genome with the following oligonucleotides (300 nM of each): 5'-GCGGCGTTATTCC-CATGACC-3' (SEQ ID NO: 23) and 5'-GGTGCCCTTCCGTCAATTCC-3' (SEQ ID NO: 29). The relative value $C_N$, which reflects the average viral genome copy number per cell, was calculated from the data with the formulas $\Delta Ct = Ct_{HPV} - Ct_{rDNA}$ and $C_N = 2^{-\Delta Ct}$. Southern blot analyses was also conducted for describing the replication properties of all marker genomes Measurement of Firefly and *Renilla* Luciferases:

The cells were lysed with passive lyses buffer (Promega) by freezing and thawing. Both *Renilla* and Firefly luciferase expression was measured with Glomax 20/20 luminometer (Promega) using Dual-Luciferase reporter assay system by manufacturer's protocol (Promega).

Cell Line U2OS GFP-2 Fluc #10.15

Characterization of U2OS GFP2-Fluc #10.15 Cell Line:

A monoclonal U2OS cell line was generated stably expressing both GFP2 and Firefly luciferase (Fluc) reporter genes. To determine whether firefly luciferase allows monitoring cell growth and toxicity of the compounds, 150 000 U2OS wt (for Fluc baseline) or U2OS #10.15 cells were seeded onto 6-well plates and grown for 3 and 5 days and Firefly luciferase levels were measured. It was found (FIG. 5, panel A) that Fluc readouts increase as the cells grow and divide, making this cell line suitable for monitoring growth, as well as toxicity of the screened compounds. Flow cytometry analyses showing uniform distribution of GFP expression in cell line #10.15 was also conducted (FIG. 4 C).

Next step was to characterize the ability of cell line U2OS #10.15 to support the replication of HPVs and compare it to the unmodified U2OS cell line. Both U2OS wt and #10.15 were transfected with 2 ug of HPV18 genome. Genomic DNA was extracted 3 and 5 days after the transfection, restricted with BglI and digested with DpnI to distinguish between replicated and transfected HPV18 DNA. The replication signals were quantified using quantitative real-time PCR (qPCR) as described in Example 4. Results in FIG. 5, panel A show that the addition of GFP2 and Fluc ORFs into U2OS #10.15 cell line did not alter the initial amplification of HPV18 compared to the wt U2OS cells. The cell line U2SO #10.15 was deposited with accession number ACC3258.

Figure 5:
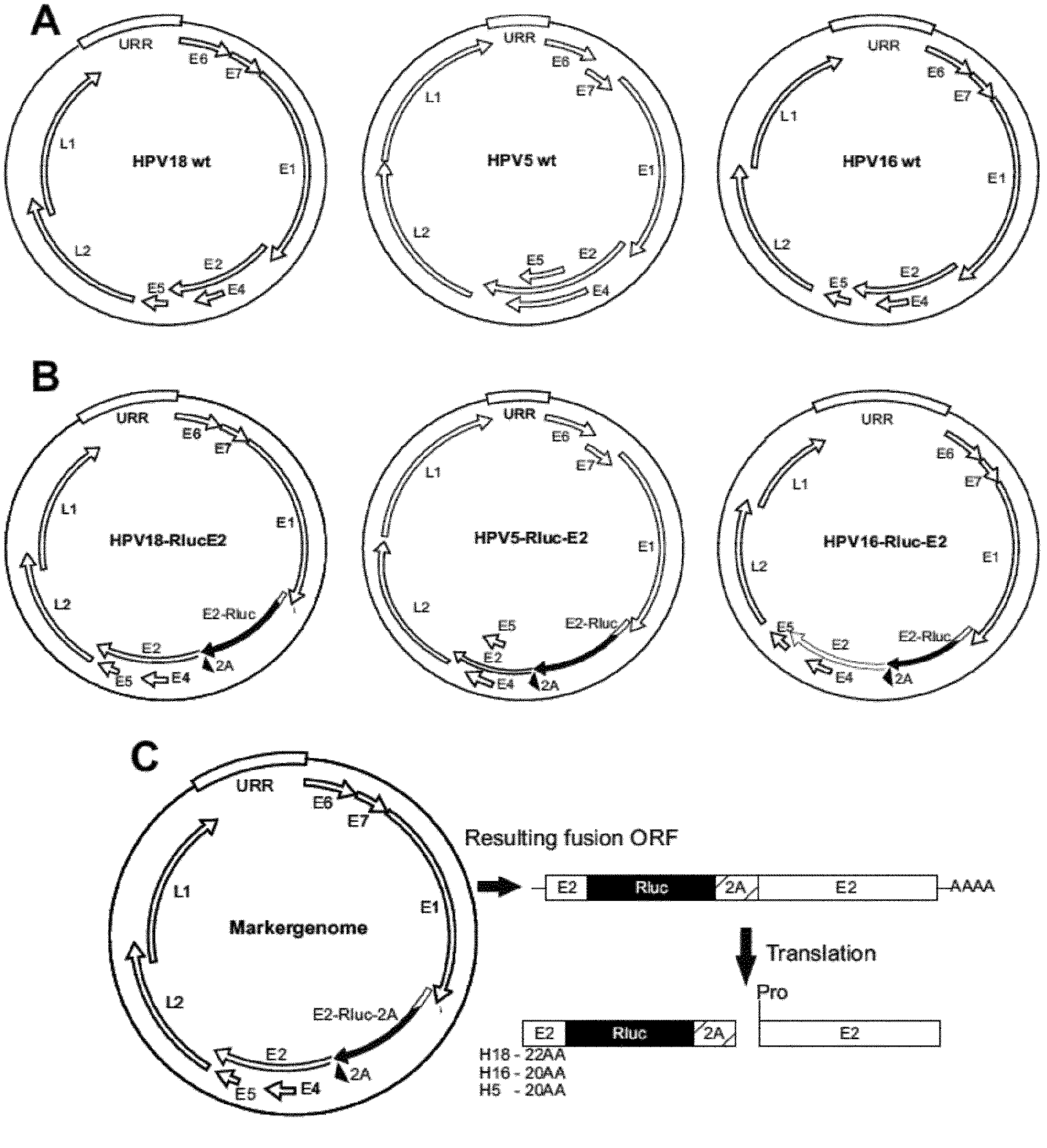
FIG. 5. Schematic map of the working principle of the *Renilla* luciferase coding marker genomes. A: Schematic maps of HPV18, 5 and 11 wt genomes. B: Schematic maps of the HPV18, 5 and 16 Rluc-E2 marker genomes. C: The coding sequences of *Renilla* luciferase and 2A peptide of FMDV are inserted in frame into E2 ORF of the HPV immediately after the overlapping region of E1 and E2. Full-length E2 gene follows the 2A sequence. The translation results in functional *Renilla* luciferase and E2 proteins separated by the "cleavage" of 2A peptide. *Renilla* luciferase protein contains additional amino acids of N-terminal E2 protein, as shown. Additional amino acid Proline is in the beginning of E2 protein. The *Renilla* luciferase expression is controlled by viral transcription. Modified regions of the viral genome are shown in black.
Figure 6:
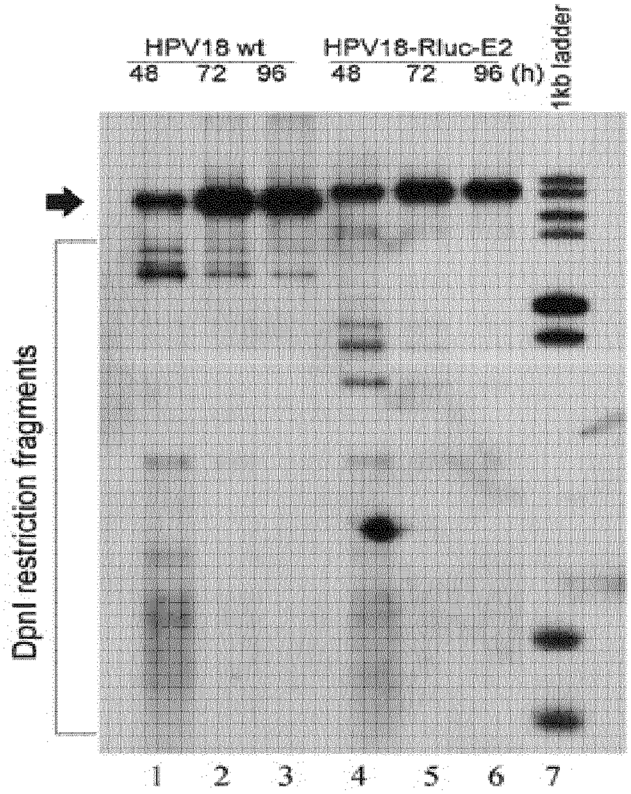
FIG. 6. Analysis of the transient replication of HPV18 marker genome in U2OS GFP2-Fluc #10.15 cell line. U2OS

Initial Amplification of HPV18-RlucE2, HPV16-RlucE2 and HPV5-RlucE2 Marker Genomes in U2OS GFP2-Fluc #10.15 Cell Line:

Schematic representations of the wt HPV18 and HPV5 genomes as well as working principles of HPV18, HPV16 and HPV5 marker genomes are shown in FIG. 5. To characterize the replication properties of HPV18-Rluc-E2 marker genome, the U2OS #10.15 cells were transfected with 2 ug of HPV18 wt and Rluc-E2 genomes. Low-molecular-weight DNA was extracted 48, 72 and 96 h after the transfection, restricted with BglI, digested with DpnI and the replication of the HPV18 genomes were analysed by Southern Blot. Results in FIG. 7, panel A show that HPV18-Rluc-E2 genome replicates similarly to wt genome (compare lanes 4, 5 and 6 with 1, 2 and 3). To further study the replication properties of HPV18, HPV16 and HPV5 marker genomes, the U2OS #10.15 cells were transfected with 2 ug of HPV18 wt, HPV18RlucE2, HPV16 wt, HPV16-RlucE2 HPV5 wt and HPV5-RlucE2. Genomic DNA was extracted 3, 5 and 7 days after the transfection, restricted with BglI (for HPV18), ScaI (for HPV16) or SacI (for HPV5) and digested with DpnI to distinguish between replicated and transfected DNA. The replication signals were quantified using quantitative real-time PCR (qPCR). Replication signal of the HPV18-RlucE2, HPV16-RlucE2 and HPV5-RlucE2 is expressed relative to the signal obtained from the respective wt at 3 day time point (FIG. 7, panel B). As can be seen, both marker genomes replicate similarly to their respective wt genomes. Both Firefly (from U2OS genome) and *Renilla* (from HPV marker genomes) luciferase expression was also measured in the same experiment and are expressed as a ratio of Rluc/Fluc measured by dual-luciferase assay described in Example 4. The results in FIG. 7, panel C show that for HPV18, HPV16 and HPV5 marker genomes, *Renilla* luciferase resembles the increase in the viral copy number shown in panel B. HPV18, HPV16 and HPV5 wt serve as negative controls for *Renilla* expression Marker Gene Expression from HPV18-RlucE2 and its Correlation with Genome Copy Number in Cells.

To measure the changes in the viral copy number and how the expression of *Renilla* luciferase resembles it, HPV18 specific siRNA-s were used. The siRNA-s were named after target sequence range in HPV18 genome: 83-105; 965-987; 3893-3915. U2OS #10.15 cells were transfected with 2 ug of HPV18-RlucE2 together with 500 pmol of siRNA-s and genomic DNA samples were collected 2 and 3 days after the transfection. Replication signals (FIG. 8 panel A) and Rluc/Fluc ratios (FIG. 8, panel B) were quantitated as described in Example 4. In these graphs the relative numbers are obtained by normalizing the data points to the same time-point data of HPV18-RlucE2 marker genome transfected alone (mock). As can be seen from FIG. 8, panel A, the siRNA-s decrease the replication of HPV18-RlucE2 to a different extent. FIG. 8, panel B shows that the *Renilla* signals decrease as well, thus showing that *Renilla* levels resemble the viral copy number in U2OS cells.

Analysis of the Viral Transcription of the HPV18-RlucE2 Marker Genome Compared to the wt HPV18.

The complex transcription map of the wt HPV18 in U2OS cells using 5' RACE analysis has been characterized previously. The map indicated the activity of five promoters and several splicing sites are responsible for generation more than 20 different viral mRNA species during viral genome replication. This data also demonstrated that HPV18 transcription in U2OS cells is very similar to transcription during productive infection in human keratinocytes as shown by Wang et al.

Here the transcription map of the HPV18-RlucE2 and wt HPV18 in U2OS cells was compared. PolyA+RNA templates were extracted from U2OS cells that had been transfected with 500 ng of the wt HPV18 genome or with the HPV18-RlucE2 (72 h time-point). Thereafter 500 ng of the polyA+RNA was used as a template 5'RACE performed with the SMARTer™ RACE cDNA Amplification Kit (Clontech) according to the manufacturer's instructions. The results shown on FIG. 9 indicate a very similar RACE PCR (with primers Pr1397 (SEQ ID NO: 26) binds to E1 ORF and Pr904-1 (SEQ ID NO:27) binds to E7 ORF) patterns for wt HPV18 and HPV18-RlucE2. It confirms that the promoter activity and splicing in viral early region of the marker genome are highly similar to wt HPV18.

Selection of Cell Lines Maintaining HPV Replication

U2OS 10.15 cells were transfected with 2 ug of HPV18-Rluc-E2 and 500 ng of linearized pBabeNeo plasmid (gives resistance to G-418). Three days after the transfection, 400 ug/ml G-418 was added to the media and cells were grown in the presence of antibiotic for two weeks. After the selection has ended cells were seeded onto tissue culture plates at low density. Colonies arisen from single cell were picked and grown further. Next colonies were analysed for *Renilla* luciferase expression. Clones expressing *Renilla* luciferase contain HPV18-Rluc-E2 markergenome. From this analyses we obtained four clones in which *Renilla* luciferase expression was detectable (data not shown): #2B3, #2G10, #2E4 and #2C4.

Analysis of the Monoclonal U2OS #10.15 (ACC3259) Cell-Lines Stably Replicating Episomal HPV18-Rluc-E2 Genome.

During normal productive infection HPV genome replicates as extrachromosomal (episomal) plasmid. However, in some circumstances integration of viral genome into host chromosomes can occur. Cell lines suitable for identification of HPV replication inhibitors have to contain viral genome in episomal form. To evaluate if these cell lines contain HPV18 marker genome in episomal form, we grew the cells in the presence of HPV18-specific inhibitors (identified by us). Idea of this experiment is that if HPV genomes are episomal, it is possible to inhibit it's replication. Results in FIG. 9, panel A show that in the clone #2C4 HPV18-Rluc-E2 is integrated into U2OS genome because *Renilla* signals are not inhibited by the addition of two compounds. In case of clone #2E4, *Renilla* expression is inhibited but its levels are relatively low, and this clone is therefore not suitable. In case of two clones, #2B3 (ACC3260) and #2G10 (ACC3258), *Renilla* level is lower in the presence of HPV18 inhibitors compared to the control sample (contains DMSO, used to dissolve compounds) which indicates that HPV18-Rluc-E2 is in episomal form. In FIG. 9, panel B both *Renilla* and Firefly luciferase signals from the clones #2B3 and #2G10 measured in two different days are shown.

Next, genomic DNA was extracted from two suitable cell lines and viral copy number was measured by qPCR analyses. #2G10 (ACC3258) has approximately 200 copies of HPV18-Rluc-E2 per cell whereas #2B3 (ACC3260) has 70. Both if these cell lines could be used to identify compounds specifically inhibiting HPV DNA replication.

For analyses of late amplification of HPV18-RlucE2 marker genome, cell lines #2G10 and #2B3 were seeded onto 100 mm plates (1 million cells per dish) and grown in confluent conditions for up to 12 days. The growth media was changed after every 2 days. HPV18-RlucE2 late amplification was quantified by qPCR analyses and by measuring *Renilla* and Firefly luciferases. Analyses shows that similarly to wt. HPV18 genome, late amplification of HPV18-RlucE2 markergenome occurs in the dense cell culture. (FIG. 9).

A Kit for Detecting Compounds Capable of Inhibiting HPV DNA Replication

A kit was completed by providing HPV marker genomes (SEQ ID NO: 2, 4, or 43) suitable to transfect into human osteosarcoma cell line U2OS deposited with accession number ACC3259, allowing to monitor initial amplification. The cell lines with deposition numbers ACC3258 and ACC3260 were cultivated to confluency. Any library of chemical compounds available or generated by a person skilled in the art can be applied to the transfected, preconfluent and/or confluent cell culture to screen the provided compounds from the library for their anti-HPV activity at initial amplification, stable maintenance and/or amplificational stage of viral DNA replication. The *Renilla* luciferase reporter gene works as a means for quantitative assessment of replicated extrachromosomal DNA, as the amount of the light produced of the inserted gene is readily detectable for a person skilled in the art quantitatively by measuring the luminescence. The Firefly luciferase reporter gene works as a means for quantitative assessment of cellular viability, as the amount of the light produced of the inserted gene is readily detectable for a person skilled in the art quantitatively by measuring the luminescence.

REFERENCES

1. Bernard H U, Burk R D, Chen Z, van Doorslaer K, zur Hausen H, et al. (2010) Classification of papillomaviruses (PVs) based on 189 P V types and proposal of taxonomic amendments. Virology 401: 70-79.
2. Munoz N, Bosch F X, de Sanjose S, Herrero R, Castellsague X, et al. (2003) Epidemiologic classification of human papillomavirus types associated with cervical cancer. N Engl J Med 348: 518-527.
3. Munoz N, Castellsague X, de Gonzalez A B, Gissmann L (2006) Chapter 1: HPV in the etiology of human cancer. Vaccine 24 Suppl 3: S3/1-10.
4. Bouvard V, Baan R, Straif K, Grosse Y, Secretan B, et al. (2009) A review of human carcinogens—Part B: biological agents. Lancet Oncol 10: 321-322.
5. Ferlay J, Shin H R, Bray F, Forman D, Mathers C, et al. (2010) Estimates of worldwide burden of cancer in 2008: GLOBOCAN 2008. Int J Cancer 127: 2893-2917.
6. Dunne E F, Unger E R, Sternberg M, McQuillan G, Swan D C, et al. (2007) Prevalence of HPV infection among females in the United States. JAMA 297: 813-819.
7. Roman A, Munger K (2013) The papillomavirus E7 proteins. Virology 445: 138-168.
8. Vande Pol S B, Klingelhutz A J (2013) Papillomavirus E6 oncoproteins. Virology 445: 115-137.

9. Akgul B, Cooke J C, Storey A (2006) HPV-associated skin disease. J Pathol 208: 165-175.
10. Malik H, Khan F H, Ahsan H (2014) Human papillomavirus: current status and issues of vaccination. Arch Virol 159: 199-205.
11. Hebner C M, Laimins L A (2006) Human papillomaviruses: basic mechanisms of pathogenesis and oncogenicity. Rev Med Virol 16: 83-97.
12. Doorbar J, Quint W, Banks L, Bravo I G, Stoler M, et al. (2012) The biology and life-cycle of human papillomaviruses. Vaccine 30 Suppl 5: F55-70.
13. Androphy E J, Lowy D R, Schiller J T (1987) Bovine papillomavirus E2 trans-activating gene product binds to specific sites in papillomavirus DNA. Nature 325: 70-73.
14. Mohr L I, Clark R, Sun S, Androphy E J, MacPherson P, et al. (1990) Targeting the E1 replication protein to the papillomavirus origin of replication by complex formation with the E2 transactivator. Science 250: 1694-1699.
15. Blitz I L, Laimins L A (1991) The 68-kilodalton E1 protein of bovine papillomavirus is a DNA binding phosphoprotein which associates with the E2 transcriptional activator in vitro. J Virol 65: 649-656.
16. Weitzman M D, Lilley C E, Chaurushiya M S (2010) Genomes in conflict: maintaining genome integrity during virus infection. Annu Rev Microbiol 64: 61-81.
17. McFadden K, Luftig M A (2013) Interplay between DNA tumor viruses and the host DNA damage response. Curr Top Microbiol Immunol 371: 229-257.
18. Marechal A, Zou L (2013) DNA damage sensing by the ATM and ATR kinases. Cold Spring Harb Perspect Biol 5.
19. Reinson T, Toots M, Kadaja M, Pipitch R, Allik M, et al. (2013) Engagement of the ATR-dependent DNA damage response at the human papillomavirus 18 replication centers during the initial amplification. J Virol 87: 951-964.
20. Sakakibara N, Mitra R, McBride A A (2011) The papillomavirus E1 helicase activates a cellular DNA damage response in viral replication foci. J Virol 85: 8981-8995.
21. Fradet-Turcotte A, Bergeron-Labrecque F, Moody C A, Lehoux M, Laimins L A, et al. (2011) Nuclear accumulation of the papillomavirus E1 helicase blocks S-phase progression and triggers an ATM-dependent DNA damage response. J Virol 85: 8996-9012.
22. Moody C A, Laimins L A (2009) Human papillomaviruses activate the ATM DNA damage pathway for viral genome amplification upon differentiation. PLoS Pathog 5: e1000605.
23. Orav M, Henno L, Isok-Paas H, Geimanen J, Ustav M, et al. (2013) Recombination-dependent oligomerization of human papillomavirus genomes upon transient DNA replication. J Virol 87: 12051-12068.
24. Gillespie K A, Mehta K P, Laimins L A, Moody C A (2012) Human papillomaviruses recruit cellular DNA repair and homologous recombination factors to viral replication centers. J Virol 86: 9520-9526.
25. Fradet-Turcotte A, Morin G, Lehoux M, Bullock P A, Archambault J (2010) Development of quantitative and high-throughput assays of polyomavirus and papillomavirus DNA replication. Virology 399: 65-76.
26. Lembo D, Donalisio M, De Andrea M, Cornaglia M, Scutera 5, et al. (2006) A cell-based high-throughput assay for screening inhibitors of human papillomavirus-16 long control region activity. FASEB J 20: 148-150.
27. Wang Y, Li X, Song S, Wu J (2014) Development of Basal-Like HaCaT Keratinocytes Containing the Genome of Human Papillomavirus (HPV) Type 11 for Screening of Anti-HPV Effects. J Biomol Screen 19: 1154-1163.
28. Huang H S, Pyeon D, Pearce S M, Lank S M, Griffin L M, et al. (2012) Novel antivirals inhibit early steps in HPV infection. Antiviral Res 93: 280-287.
29. Geimanen J, Isok-Paas H, Pipitch R, Salk K, Laos T, et al. (2011) Development of a cellular assay system to study the genome replication of high- and low-risk mucosal and cutaneous human papillomaviruses. J Virol 85: 3315-3329.
30. Sankovski E, Mannik A, Geimanen J, Ustav E, Ustav M (2014) Mapping of betapapillomavirus human papillomavirus 5 transcription and characterization of viral-genome replication function. J Virol 88: 961-973.
31. Toots M, Mannik A, Kivi G, Ustav M, Jr., Ustav E, et al. (2014) The transcription map of human papillomavirus type 18 during genome replication in U2OS cells. PLoS One 9: e116151.
32. Wang X, Meyers C, Wang H K, Chow L T, Zheng Z M (2011) Construction of a full transcription map of human papillomavirus type 18 during productive viral infection. J Virol 85: 8080-8092.
33. Chow L T, Nasseri M, Wolinsky S M, Broker T R (1987) Human papillomavirus types 6 and 11 mRNAs from genital condylomata *acuminata*. J Virol 61: 2581-2588.
34. Blais J D, Addison C L, Edge R, Falls T, Zhao H, et al. (2006) Perk-dependent translational regulation promotes tumor cell adaptation and angiogenesis in response to hypoxic stress. Mol Cell Biol 26: 9517-9532.
35. Johansson C, Somberg M, Li X, Backstrom Winquist E, Fay J, et al. (2012) HPV-16 E2 contributes to induction of HPV-16 late gene expression by inhibiting early polyadenylation. EMBO J 31: 3212-3227.
36. Kay M A, He C Y, Chen Z Y (2010) A robust system for production of minicircie DNA vectors. Nat Biotechnol 28: 1287-1289.
37. Hirt B (1967) Selective extraction of polyoma DNA from infected mouse cell cultures. J Mol Biol 26: 365-369.

What is claimed is:

1. A genetically modified monoclonal human osteosarcoma cell line expressing firefly luciferase and GPF2 proteins and being capable of supporting all phases of HPV DNA replication, said cell line being transfected with an extrachromosomally maintainable plasmid comprising a marker genome wherein complete or partial coding sequence of a marker gene is inserted into the ORF of E2 protein, whereby the expression of marker gene is regulated by the modulation of viral promoters, wherein the marker gene is *Renilla* luciferase having coding sequence of SEQ ID NO: 30.

2. The cell line of claim 1, wherein the HPV is selected from alpha or beta group of HPV.

3. The cell line of claim 2, wherein the HPV is HPV18 and the E2 ORF is according to SEQ ID NO: 14 or HPV is HPV 16 and the E2 ORF is according to SEQ ID NO: 34.

4. The cell line of claim 1, wherein the HPV is HPV 5 and the E2 ORF is according to SEQ ID NO:15.

5. The cell line of claim 1, wherein the plasmid has nucleic acid sequence SEQ ID NO: 1, SEQ ID NO: 3 or SEQ ID NO:42.

6. A genetically modified monoclonal human osteosarcoma (U2OS) cell line stably expressing firefly luciferase and GFP2 proteins and being deposited with accession number DSM ACC3259, the cell line enabling initial replication, stable maintenance and vegetative amplificational replication of HPV DNA.

7. The genetically modified monoclonal cell line of claim 6, wherein the HPV is HPV 5, HPV18, or HPV 16.

8. The genetically modified monoclonal cell line of claim 6 transfected with marker genome plasmid having nucleotide sequence according to SEQ ID NO:2, SEQ ID NO: 4, or SEQ ID NO:43.

9. The genetically modified monoclonal cell line of claim 6, wherein the cell line has 70 copies of the viral plasmid and has deposit number DSM ACC 3260 or the cell line has 200 copies of the viral plasmid and has deposit number DSM ACC 3258.

* * * * *